(12) United States Patent
Durrant et al.

(10) Patent No.: US 12,139,544 B2
(45) Date of Patent: Nov. 12, 2024

(54) EphA3 DIRECTED CAR-T CELLS FOR TREATMENT OF TUMORS

(71) Applicants: HUMANIGEN, INC., Burlingame, CA (US); MAYO FOUNDATION FOR MEDICAL EDUCATION AND RESEARCH, Rochester, MN (US)

(72) Inventors: Cameron Durrant, Oxford, FL (US); Dale Chappell, Dolores, CO (US); Saad J. Kenderian, Rochester, MN (US)

(73) Assignee: MAYO FOUNDATION FOR MEDICAL EDUCATION AND RESEARCH, Rochester, MN (US)

(*) Notice: Subject to any disclaimer, the term of this patent is extended or adjusted under 35 U.S.C. 154(b) by 433 days.

(21) Appl. No.: 17/093,370

(22) Filed: Nov. 9, 2020

(65) Prior Publication Data

US 2021/0246215 A1     Aug. 12, 2021

Related U.S. Application Data

(60) Provisional application No. 62/933,354, filed on Nov. 8, 2019.

(51) Int. Cl.
| | | |
|---|---|---|
| *C07K 16/28* | (2006.01) | |
| *A61K 35/17* | (2015.01) | |
| *A61P 35/00* | (2006.01) | |
| *C07K 14/705* | (2006.01) | |
| *C07K 14/725* | (2006.01) | |
| *C07K 16/24* | (2006.01) | |
| *C12N 15/86* | (2006.01) | |
| *A61K 38/00* | (2006.01) | |
| *A61K 39/00* | (2006.01) | |

(52) U.S. Cl.
CPC .......... *C07K 16/2866* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 16/243* (2013.01); *C07K 16/2818* (2013.01); *C07K 16/2827* (2013.01); *C12N 15/86* (2013.01); *A61K 38/00* (2013.01); *A61K 2039/507* (2013.01); *A61K 2039/5156* (2013.01); *A61K 2039/5158* (2013.01); *C07K 2317/24* (2013.01); *C07K 2317/53* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2740/15043* (2013.01)

(58) Field of Classification Search
CPC .......... C07K 16/2866; C07K 14/7051; C07K 14/70517; C07K 14/70521; C07K 14/70578; C07K 16/243; C07K 16/2818; C07K 16/2827; C07K 2317/24; C07K 2317/53; C07K 2317/622; C07K 2317/76; C07K 2319/02; C07K 2319/03; C07K 2319/30; C07K 2319/33; A61K 35/17; A61K 38/00; A61K 2039/507; A61K 2039/5156; A61K 2039/5158; A61K 39/3955; A61P 35/00; C12N 15/86; C12N 2740/15043

See application file for complete search history.

(56) References Cited

U.S. PATENT DOCUMENTS

| | | |
|---|---|---|
| 5,994,136 A | 11/1999 | Naldini et al. |
| 8,168,183 B2 | 5/2012 | Bebbington et al. |
| 9,017,674 B2 | 4/2015 | Bebbington et al. |
| 9,394,368 B2 | 7/2016 | Brogdon et al. |
| 11,390,655 B2 | 7/2022 | Sievers et al. |
| 2011/0123549 A1 | 5/2011 | Luehrsen et al. |
| 2011/0243934 A1 | 10/2011 | Palath et al. |
| 2012/0321619 A1 | 12/2012 | Linden et al. |
| 2012/0322073 A1 | 12/2012 | Lopez-Girona et al. |
| 2013/0095123 A1 | 4/2013 | Lerchen et al. |
| 2014/0120114 A1* | 5/2014 | Luehrsen ............. A61P 7/00 530/389.1 |
| 2015/0147278 A1 | 5/2015 | Masuko et al. |
| 2016/0075784 A1* | 3/2016 | Yu ................. C07K 16/3061 435/328 |
| 2017/0283509 A1 | 10/2017 | Logsdson et al. |

(Continued)

FOREIGN PATENT DOCUMENTS

| | | |
|---|---|---|
| JP | WO-2011/158883 | 12/2011 |
| JP | WO-2013/183786 | 12/2013 |

(Continued)

OTHER PUBLICATIONS

Chaudhary VK et al. A recombinant single-chain immunotoxin composed of anti-Tac variable regions and a truncated diphtheria toxin. Proc. Natl. Acad. Sci. 1990 87, 9491-9494. (Year: 1990).*

(Continued)

*Primary Examiner* — Karen A. Canella
*Assistant Examiner* — John J Skoko, III
(74) *Attorney, Agent, or Firm* — Mark S. Cohen; PEARL COHEN ZEDEK LATZER BARATZ LLP

(57) ABSTRACT

This invention provides chimeric antigen receptors (CARs) targeting human EphA3 and dual targeting CARs that bind to human EphA3 and to human mutant epidermal growth factor receptor variant III (EGFRvIII). This invention also relates to CAR-T cells comprising the provided CARs or the dual targeting CARs. Methods for treating a solid tumor cancer by administering the CARs are provided.

21 Claims, 30 Drawing Sheets

Specification includes a Sequence Listing.

(56) References Cited

U.S. PATENT DOCUMENTS

| | | | |
|---|---|---|---|
| 2018/0125892 | A1* | 5/2018 | Brannetti ....... A61K 39/001124 |
| 2018/0170992 | A1 | 6/2018 | Balyasnikova et al. |
| 2018/0346876 | A1* | 12/2018 | Xiao .............. C12Y 207/07049 |
| 2019/0008897 | A1* | 1/2019 | Scatena .......... C12Y 502/01008 |
| 2019/0144515 | A1 | 5/2019 | Sievers et al. |
| 2019/0153471 | A1 | 5/2019 | Paul et al. |
| 2019/0270821 | A1 | 9/2019 | Yarranton |
| 2019/0300616 | A1 | 10/2019 | Balyasnikova et al. |
| 2022/0389449 | A1 | 12/2022 | Paul et al. |
| 2022/0401488 | A1 | 12/2022 | Kenderian et al. |
| 2022/0402998 | A1 | 12/2022 | Liu et al. |

FOREIGN PATENT DOCUMENTS

| | | | |
|---|---|---|---|
| WO | WO-2003/080672 | | 10/2003 |
| WO | WO-2011/070088 | | 6/2011 |
| WO | WO-2016/028896 | | 2/2016 |
| WO | WO-2016033331 | A1 * | 3/2016 ............. A61K 35/17 |
| WO | WO-2017/027291 | | 2/2017 |
| WO | WO-2017189959 | A1 * | 11/2017 ............. C07K 16/00 |
| WO | WO-2018/053032 | A1 | 3/2018 |
| WO | WO-2018/053649 | | 3/2018 |
| WO | WO-2019/157533 | | 8/2019 |
| WO | WO-2019/195586 | A1 | 10/2019 |
| WO | WO-2021/087245 | | 5/2021 |

OTHER PUBLICATIONS

Zhang C et al. Engineering CAR-T cells. Biomark Res 2017 5:22 1-6. (Year: 2017).*

International Search Report dated Mar. 26, 2021 in respect of PCT Int'l Application No. PCT/US20/059675.

International Preliminary Report on Patentability dated May 19, 2022 in respect of PCT Int'l Application No. PCT/US2020/059675.

GenBank Accession No. NM_000734.3, "*Homo sapiens* CD247 molecule (CD247), transcript variant 2, mRNA," dated Jul. 21, 2018, 5 pages.

Anonymous: "Kite and Humanigen Announce Clinical Collaboration to Evaluate Investigational Combination of Yescarta (Axicabtagene Ciloleucel) with Lenzilumab in Relapsed/Refractory Diffuse Large B-Cell Lymphoma", Retrieved from the Internet: URL:https://www.gilead.com/news-and-pressloress-room/press-releases/2019/5/kite-and-humanicen-announce-clinical-collaboration-to-evaluate-investigational-combination-of-yescarta-axicabiagene-ciloleucel-with-lenzilumab-in-r [retrieved on Oct. 27, 2023].

Charmsaz, Sara et al.; "Targeted therapies in hematological malignancies using therapeutic monoclonal antibodies against Eph family receptors", Experimental Hematology 2017; vol. 54: pp. 31-39, XP055946524, US ISSN: 0301-472X, DOI: 10.1016/j.exphen.2017.07.003.

Humanigen: "Enhancing T-Cell Therapies in Oncology", Aug. 20, 2018, XP093095791, Retrieved from the Internet: URL:chrome-extension://efaidnbmnnnlbpcajpcgiclsllndmkai/https://dilo3yog0oux5.cloudiront.net/_271a1b2die61694720cd8f66f9163814/humanicen/db/299/1233/pd/HGEN+Non-confidential+6-20-18.pdf [retrieved on Oct. 27, 2023].

Ruff, Michael et al.; "EXTH-32. Development of Epha3 Directed Chimeric Antigen Receptor T Cell Therapy for the Treatment of Glioblastoma Multiforme", Neuro-oncology 2019, pp. vi88-vi89, XP055817207, Retrieved from the Internet: URL:https://www.nobi.nim.nih.gov/pmc/articles/PMC6847906/pdf/nozl75.364.pdf [retrieved on Jun. 23, 2021].

Sharma, Puja et al.; "Receptor-Targeted Glial Brain Tumor Therapies", Int. J. Mol. Sci. 2018, vol. 19, No. 11, pp. 3326, XP055818538, DOI: 10.3390/ijms19113326.

Extended EP Search Report dated Nov. 7, 2023 in respect of EP Patent Application No. 20885566.8.

* cited by examiner

K84 -GBM PDX line 39 24 hour killing assay

GBM 39 Epha3 - 6.95% RNA expression

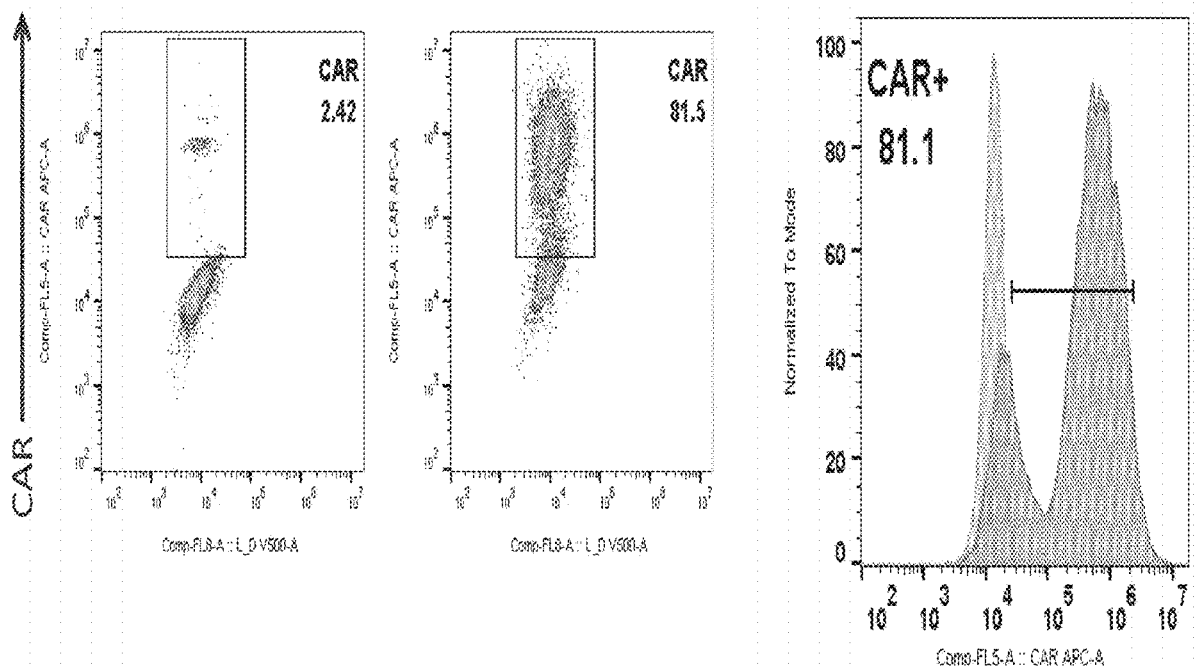
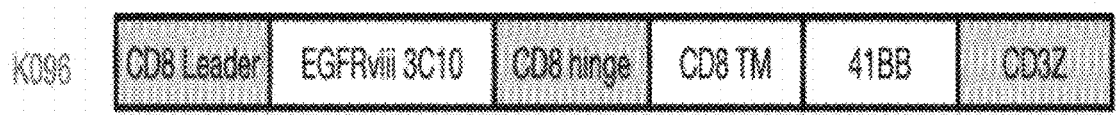
FIGS. 5A-5D

K84 - GBM PDX line 39
48* hour killing assay

GBM 39 Epha3 - 6.95% RNA expression

EGFRviii expression present
Epha3 - 1.52% RNA expression

Kindly Provided by Jessica Hartman
Hartman et al. EMBO Mol Med. 2017 Sep;9(9):1183-1197

SEQUENCE LISTING

```
<160> NUMBER OF SEQ ID NOS: 55

<210> SEQ ID NO 1
<211> LENGTH: 118
<212> TYPE: PRT
<213> ORGANISM: Artificial Sequence
<220> FEATURE:
<223> OTHER INFORMATION: EphA3 scFv heavy chain amino acid sequence

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Tyr Glu Asp Phe Asp Ser Trp Gly Gln Gly Thr
            100                 105                 110

Thr Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: EphA3 scFv light chain amino acid sequence

<400> SEQUENCE: 2

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
```

```
                35                  40                  45
Tyr Ala Ala Ser Ser Leu Gln Ser Gly Val Pro Ser Arg Phe Ser Gly
         50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Gly Gln Tyr Ala Asn Tyr Pro Tyr
                 85                  90                  95
Thr Phe Gly Gln Gly Thr Lys Leu Glu Ile Lys
            100                 105

<210> SEQ ID NO 3
<211> LENGTH: 21
<212> TYPE: PRT
<213> ORGANISM: Artificial Sequence
<220> FEATURE:
<223> OTHER INFORMATION: CD8 leader amino acid sequence

<400> SEQUENCE: 3

Met Ala Leu Pro Val Thr Ala Leu Leu Leu Pro Leu Ala Leu Leu Leu
 1               5                  10                  15
His Ala Ala Arg Pro
            20

<210> SEQ ID NO 4
<211> LENGTH: 15
<212> TYPE: PRT
<213> ORGANISM: Artificial Sequence
<220> FEATURE:
<223> OTHER INFORMATION: Linker amino acid sequence

<400> SEQUENCE: 4

Gly Gly Gly Gly Ser Gly Gly Gly Gly Ser Gly Gly Gly Gly Ser
 1               5                  10                  15

<210> SEQ ID NO 5
<211> LENGTH: 45
<212> TYPE: PRT
<213> ORGANISM: Artificial Sequence
<220> FEATURE:
<223> OTHER INFORMATION: CD8 hinge amino acid sequence

<400> SEQUENCE: 5

Thr Thr Thr Pro Ala Pro Arg Pro Pro Thr Pro Ala Pro Thr Ile Ala
 1               5                  10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
            35                  40                  45

<210> SEQ ID NO 6
<211> LENGTH: 19
<212> TYPE: PRT
<213> ORGANISM: Artificial Sequence
<220> FEATURE:
<223> OTHER INFORMATION: CD28 hinge amino acid sequence

<400> SEQUENCE: 6

Leu Glu Pro Lys Ser Cys Asp Lys Thr His Thr Cys Pro Pro Cys Pro
 1               5                  10                  15
Asp Pro Lys

<210> SEQ ID NO 7
```

```
<211> LENGTH: 24
<212> TYPE: PRT
<213> ORGANISM: Artificial Sequence
<220> FEATURE:
<223> OTHER INFORMATION: CD8 TM amino acid sequence

<400> SEQUENCE: 7

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 8
<211> LENGTH: 27
<212> TYPE: PRT
<213> ORGANISM: Artificial Sequence
<220> FEATURE:
<223> OTHER INFORMATION: CD28 TM amino acid sequence

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 42
<212> TYPE: PRT
<213> ORGANISM: Artificial Sequence
<220> FEATURE:
<223> OTHER INFORMATION: 41BB amino acid sequence

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 10
<211> LENGTH: 41
<212> TYPE: PRT
<213> ORGANISM: Artificial Sequence
<220> FEATURE:
<223> OTHER INFORMATION: CD28 amino acid sequence

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 112
<212> TYPE: PRT
<213> ORGANISM: Artificial Sequence
<220> FEATURE:
<223> OTHER INFORMATION: CD3z amino acid sequence

<400> SEQUENCE: 11

Arg Val Lys Phe Ser Arg Ser Ala Asp Ala Pro Ala Tyr Lys Gln Gly
```

```
            1               5                  10                 15
Gln Asn Gln Leu Tyr Asn Glu Leu Asn Leu Gly Arg Arg Glu Tyr
                20                  25                  30
Asp Val Leu Asp Lys Arg Arg Gly Arg Asp Pro Glu Met Gly Gly Lys
            35                  40                  45
Pro Arg Arg Lys Asn Pro Gln Glu Gly Leu Tyr Asn Glu Leu Gln Lys
        50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 12
<211> LENGTH: 484
<212> TYPE: PRT
<213> ORGANISM: Artificial Sequence
<220> FEATURE:
<223> OTHER INFORMATION: EphA3 CAR K082 (H2L-BBz) amino acid sequence

<400> SEQUENCE: 12

Met Ala Leu Pro Val Thr Ala Leu Leu Leu Pro Leu Ala Leu Leu Leu
1               5                   10                  15
His Ala Ala Arg Pro Gln Val Gln Leu Val Gln Ser Gly Ala Glu Val
                20                  25                  30
Lys Lys Pro Gly Ala Ser Val Lys Val Ser Cys Lys Ala Ser Gly Tyr
            35                  40                  45
Thr Phe Thr Gly Tyr Trp Met Asn Trp Val Arg Gln Ala Pro Gly Gln
        50                  55                  60
Gly Leu Glu Trp Met Gly Asp Ile Tyr Pro Gly Ser Gly Asn Thr Asn
65                  70                  75                  80
Tyr Asp Glu Lys Phe Gln Gly Arg Val Thr Met Thr Arg Asp Thr Ser
                85                  90                  95
Ile Ser Thr Ala Tyr Met Glu Leu Ser Arg Leu Arg Ser Asp Asp Thr
            100                 105                 110
Ala Val Tyr Tyr Cys Ala Arg Gly Gly Tyr Tyr Glu Asp Phe Asp Ser
            115                 120                 125
Trp Gly Gln Gly Thr Thr Val Thr Val Ser Ser Gly Gly Gly Gly Ser
        130                 135                 140
Gly Gly Gly Gly Ser Gly Gly Gly Gly Ser Asp Ile Gln Met Thr Gln
145                 150                 155                 160
Ser Pro Ser Phe Leu Ser Ala Ser Val Gly Asp Arg Val Thr Ile Thr
                165                 170                 175
Cys Arg Ala Ser Gln Gly Ile Ile Ser Tyr Leu Ala Trp Tyr Gln Gln
            180                 185                 190
Lys Pro Glu Lys Ala Pro Lys Arg Leu Ile Tyr Ala Ala Ser Ser Leu
        195                 200                 205
Gln Ser Gly Val Pro Ser Arg Phe Ser Gly Ser Gly Ser Gly Thr Glu
    210                 215                 220
Phe Thr Leu Thr Ile Ser Ser Leu Gln Pro Glu Asp Phe Ala Thr Tyr
225                 230                 235                 240
Tyr Cys Gly Gln Tyr Ala Asn Tyr Pro Tyr Thr Phe Gly Gln Gly Thr
                245                 250                 255
Lys Leu Glu Ile Lys Thr Thr Thr Pro Ala Pro Arg Pro Pro Thr Pro
```

```
                  260                 265                 270
Ala Pro Thr Ile Ala Ser Gln Pro Leu Ser Leu Arg Pro Glu Ala Cys
                275                 280                 285

Arg Pro Ala Ala Gly Gly Ala Val His Thr Arg Gly Leu Asp Phe Ala
            290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
                355                 360                 365

Gly Cys Glu Leu Arg Val Lys Phe Ser Arg Ser Ala Asp Ala Pro Ala
            370                 375                 380

Tyr Lys Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
            450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 13
<211> LENGTH: 460
<212> TYPE: PRT
<213> ORGANISM: Artificial Sequence
<220> FEATURE:
<223> OTHER INFORMATION: EphA3 CAR K083 (H2L-28z) amino acid sequence

<400> SEQUENCE: 13

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Trp Met Asn Trp Val Arg Gln Ala Pro Gly Gln
    50                  55                  60

Gly Leu Glu Trp Met Gly Asp Ile Tyr Pro Gly Ser Gly Asn Thr Asn
65                  70                  75                  80

Tyr Asp Glu Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Gly Gly Tyr Tyr Glu Asp Phe Asp Ser
        115                 120                 125

Trp Gly Gln Gly Thr Thr Val Thr Val Ser Ser Gly Gly Gly Gly Ser
    130                 135                 140
```

Gly Gly Gly Gly Ser Gly Gly Gly Ser Asp Ile Gln Met Thr Gln
145                 150                 155                 160

Ser Pro Ser Phe Leu Ser Ala Ser Val Gly Asp Arg Val Thr Ile Thr
            165                 170                 175

Cys Arg Ala Ser Gln Gly Ile Ile Ser Tyr Leu Ala Trp Tyr Gln Gln
                180                 185                 190

Lys Pro Glu Lys Ala Pro Lys Arg Leu Ile Tyr Ala Ala Ser Ser Leu
            195                 200                 205

Gln Ser Gly Val Pro Ser Arg Phe Ser Gly Ser Gly Ser Gly Thr Glu
    210                 215                 220

Phe Thr Leu Thr Ile Ser Ser Leu Gln Pro Glu Asp Phe Ala Thr Tyr
225                 230                 235                 240

Tyr Cys Gly Gln Tyr Ala Asn Tyr Pro Tyr Thr Phe Gly Gln Gly Thr
                245                 250                 255

Lys Leu Glu Ile Lys Leu Glu Pro Lys Ser Cys Asp Lys Thr His Thr
            260                 265                 270

Cys Pro Pro Cys Pro Asp Pro Lys Phe Trp Val Leu Val Val Val Gly
    275                 280                 285

Gly Val Leu Ala Cys Tyr Ser Leu Leu Val Thr Val Ala Phe Ile Ile
290                 295                 300

Phe Trp Val Arg Ser Lys Arg Ser Arg Leu Leu His Ser Asp Tyr Met
305                 310                 315                 320

Asn Met Thr Pro Arg Arg Pro Gly Pro Thr Arg Lys His Tyr Gln Pro
                325                 330                 335

Tyr Ala Pro Pro Arg Asp Phe Ala Ala Tyr Arg Ser Arg Val Lys Phe
            340                 345                 350

Ser Arg Ser Ala Asp Ala Pro Ala Tyr Lys Gln Gly Gln Asn Gln Leu
    355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
    435                 440                 445

Tyr Asp Ala Leu His Met Gln Ala Leu Pro Pro Arg
450                 455                 460

<210> SEQ ID NO 14
<211> LENGTH: 460
<212> TYPE: PRT
<213> ORGANISM: Artificial Sequence
<220> FEATURE:
<223> OTHER INFORMATION: EphA3 CAR K084 (L2H-28z) amino acid sequence

<400> SEQUENCE: 14

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Phe Leu
            20                  25                  30

Ser Ala Ser Val Gly Asp Arg Val Thr Ile Thr Cys Arg Ala Ser Gln
        35                  40                  45

```
Gly Ile Ile Ser Tyr Leu Ala Trp Tyr Gln Gln Lys Pro Glu Lys Ala
        50                  55                  60

Pro Lys Arg Leu Ile Tyr Ala Ala Ser Ser Leu Gln Ser Gly Val Pro
 65                  70                  75                  80

Ser Arg Phe Ser Gly Ser Gly Ser Gly Thr Glu Phe Thr Leu Thr Ile
                 85                  90                  95

Ser Ser Leu Gln Pro Glu Asp Phe Ala Thr Tyr Tyr Cys Gln Gln Tyr
                100                 105                 110

Ala Asn Tyr Pro Tyr Thr Phe Gly Gln Gly Thr Lys Leu Glu Ile Lys
            115                 120                 125

Gly Gly Gly Gly Ser Gly Gly Gly Ser Gly Gly Gly Gly Ser Gln
        130                 135                 140

Val Gln Leu Val Gln Ser Gly Ala Glu Val Lys Lys Pro Gly Ala Ser
145                 150                 155                 160

Val Lys Val Ser Cys Lys Ala Ser Gly Tyr Thr Phe Thr Gly Tyr Trp
                165                 170                 175

Met Asn Trp Val Arg Gln Ala Pro Gly Gln Gly Leu Glu Trp Met Gly
            180                 185                 190

Asp Ile Tyr Pro Gly Ser Gly Asn Thr Asn Tyr Asp Glu Lys Phe Gln
            195                 200                 205

Gly Arg Val Thr Met Thr Arg Asp Thr Ser Ile Ser Thr Ala Tyr Met
210                 215                 220

Glu Leu Ser Arg Leu Arg Ser Asp Asp Thr Ala Val Tyr Tyr Cys Ala
225                 230                 235                 240

Arg Gly Gly Tyr Tyr Glu Asp Phe Asp Ser Trp Gly Gln Gly Thr Thr
                245                 250                 255

Val Thr Val Ser Ser Leu Glu Pro Lys Ser Cys Asp Lys Thr His Thr
                260                 265                 270

Cys Pro Pro Cys Pro Asp Pro Lys Phe Trp Val Leu Val Val Val Gly
            275                 280                 285

Gly Val Leu Ala Cys Tyr Ser Leu Leu Val Thr Val Ala Phe Ile Ile
        290                 295                 300

Phe Trp Val Arg Ser Lys Arg Ser Arg Leu Leu His Ser Asp Tyr Met
305                 310                 315                 320

Asn Met Thr Pro Arg Arg Pro Gly Pro Thr Arg Lys His Tyr Gln Pro
                325                 330                 335

Tyr Ala Pro Pro Arg Asp Phe Ala Ala Tyr Arg Ser Arg Val Lys Phe
            340                 345                 350

Ser Arg Ser Ala Asp Ala Pro Ala Tyr Lys Gln Gly Gln Asn Gln Leu
            355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
450                 455                 460
```

<210> SEQ ID NO 15
<211> LENGTH: 484
<212> TYPE: PRT
<213> ORGANISM: Artificial Sequence
<220> FEATURE:
<223> OTHER INFORMATION: EphA3 CAR K085 (L2H BBz) amino acid sequence

<400> SEQUENCE: 15

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Phe Leu
            20                  25                  30

Ser Ala Ser Val Gly Asp Arg Val Thr Ile Thr Cys Arg Ala Ser Gln
        35                  40                  45

Gly Ile Ile Ser Tyr Leu Ala Trp Tyr Gln Gln Lys Pro Glu Lys Ala
    50                  55                  60

Pro Lys Arg Leu Ile Tyr Ala Ala Ser Ser Leu Gln Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Tyr
            100                 105                 110

Ala Asn Tyr Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ala Ser
145                 150                 155                 160

Val Lys Val Ser Cys Lys Ala Ser Gly Tyr Thr Phe Thr Gly Tyr Trp
                165                 170                 175

Met Asn Trp Val Arg Gln Ala Pro Gly Gln Gly Leu Glu Trp Met Gly
            180                 185                 190

Asp Ile Tyr Pro Gly Ser Gly Asn Thr Asn Tyr Asp Glu Lys Phe Gln
        195                 200                 205

Gly Arg Val Thr Met Thr Arg Asp Thr Ser Ile Ser Thr Ala Tyr Met
    210                 215                 220

Glu Leu Ser Arg Leu Arg Ser Asp Asp Thr Ala Val Tyr Tyr Cys Ala
225                 230                 235                 240

Arg Gly Gly Tyr Tyr Glu Asp Phe Asp Ser Trp Gly Gln Gly Thr Thr
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365
```

```
Gly Cys Glu Leu Arg Val Lys Phe Ser Arg Ser Ala Asp Ala Pro Ala
370                 375                 380

Tyr Lys Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
                420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg
```

<210> SEQ ID NO 16
<211> LENGTH: 1452
<212> TYPE: DNA
<213> ORGANISM: Artificial Sequence
<220> FEATURE:
<223> OTHER INFORMATION: EphA3 CAR K082 (H2L-BBz)

<400> SEQUENCE: 16

```
atggcttac cagtgaccgc cttgctcctg ccgctggcct tgctgctcca cgccgccagg      60
ccgcaggtgc agctggtgca gtctgggggct gaggtgaaga agcctggggc ctcagtgaag     120
gtttcctgca aggcttctgg atacaccttc acaggctact ggatgaattg ggtgcgccag     180
gcccccgggc aaggcctgga gtggatgggg acatctacc cgggcagtgg taacacaaac     240
tacgatgaga agttccaggg tagagtcacg atgaccaggg acacgtccat cagcacagcc     300
tacatggagc tgagcaggct gagatctgac gacacagccg tgtactactg cgcaagaggt     360
ggatattatg aagattttga tagctggggc caaggtacca ctgtgaccgt gagctccggt     420
ggaggtggtt cggaggtgg aggtagcgga ggtggtggat ctgacatcca gatgacccag     480
tctccatcct cctgtctgc atctgtagga gacagagtca ccatcacttg ccgggccagt     540
cagggcatta tcagttattt agcctggtat cagcaaaaac cagagaaagc ccctaagcgc     600
ctgatctatg ctgcatccag tttgcaaagt ggggtcccat caaggttcag cggcagtgga     660
tctgggacag aattcactct cacaatcagc agcctgcagc ctgaagattt tgcaacttac     720
tactgcgggc agtatgccaa ttatccgtac acctttggcc aaggtacgaa actggaaatt     780
aaaaccacta cccctgcacc gcgaccacca caccggcgc ccaccattgc gtcgcagcct     840
ctgtccctgc gccagaagc atgccgtcca gcagcaggtg gtgcagttca tactcgtggt     900
ctggatttcg cctgtgatat ctacatctgg gcgcccttgg ccgggacttg tggggtcctt     960
ctcctgtcac tggttatcac cctttactgc aaacggggca gaaagaaact cctgtatata    1020
ttcaaacaac catttatgag accagtacaa actactcaag aggaagatgg ctgtagctgc    1080
cgatttccag aagaagaaga aggaggatgt gaactgagag tgaagttcag caggagcgca    1140
gacgcccccg cgtacaagca gggccagaac cagctctata acgagctcaa tctaggacga    1200
agagaggagt acgatgtttt ggacaagaga cgtggccggg accctgagat gggggggaaag    1260 ccgagaagga gaaccctca ggaaggcctg tacaatgaac tgcagaaaga taagatggcg    1320
gaggcctaca gtgagattgg gatgaaaggc gagcgccgga ggggcaaggg gcacgatggc    1380
```

```
ctttaccagg gtctcagtac agccaccaag gacacctacg acgcccttca catgcaggcc    1440
ctgccccctc gc                                                         1452

<210> SEQ ID NO 17
<211> LENGTH: 1380
<212> TYPE: DNA
<213> ORGANISM: Artificial Sequence
<220> FEATURE:
<223> OTHER INFORMATION: EphA3 CAR K083 (H2L-28z)

<400> SEQUENCE: 17
atggccttac cagtgaccgc cttgctcctg ccgctggcct tgctgctcca cgccgccagg      60
ccgcaggtgc agctggtgca gtctggggct gaggtgaaga agcctggggc ctcagtgaag     120
gtttcctgca aggcttctgg atacaccttc acaggctact ggatgaattg ggtgcgccag     180
gcccccgggc aaggcctgga gtggatgggg acatctaccc gggcagtggt aacacaaac     240 tacgatgaga agttccaggg tagagtcacg atgaccaggg acacgtccat cagcacagcc     300
tacatggagc tgagcaggct gagatctgac gacacagccg tgtactactg cgcaagaggt     360
ggatattatg aagattttga tagctggggc caaggtacca ctgtgaccgt gagctccggt     420
ggaggtggtt cggaggtgg aggtagcgga ggtggtggat ctgacatcca gatgacccag     480
tctccatcct cctgtctgc atctgtagga gacagagtca ccatcacttg ccgggccagt     540
cagggcatta tcagttattt agcctggtat cagcaaaaac cagagaaagc ccctaagcgc     600
ctgatctatg ctgcatccag tttgcaaagt ggggtcccat caaggttcag cggcagtgga     660
tctgggacag aattcactct cacaatcagc agcctgcagc ctgaagattt tgcaacttac     720
tactgcgggc agtatgccaa ttatccgtac acctttggcc aaggtacgaa actggaaatt     780
aaactcgagc ccaaatcttg tgacaaaact cacacatgcc caccgtgccc ggatcccaaa     840
ttttgggtgc tggtggtggt tggtggagtc ctggcttgct atagcttgct agtaacagtg     900
gcctttatta ttttctgggt gaggagtaag aggagcaggc tcctgcacag tgactacatg     960
aacatgactc cccgccgccc cgggccccac cgcaagcatt accagcccta tgccccacca    1020
cgcgacttcg cagcctatcg ctccagagtg aagttcagca ggagcgcaga cgcccccgcg    1080
tacaagcagg gccagaacca gctctataac gagctcaatc taggacgaag agaggagtac    1140
gatgttttgg acaagagacg tggccgggac cctgagatgg ggggaaagcc gagaaggaag    1200
aaccctcagg aaggcctgta caatgaactg cagaaagata agatggcgga ggcctacagt    1260
gagattggga tgaaaggcga gcgccggagg ggcaaggggc acgatggcct ttaccagggt    1320
ctcagtacag ccaccaagga cacctacgac gccttcaca tgcaggccct gccccctcgc    1380

<210> SEQ ID NO 18
<211> LENGTH: 1380
<212> TYPE: DNA
<213> ORGANISM: Artificial Sequence
<220> FEATURE:
<223> OTHER INFORMATION: EphA3 CAR K084 (L2H-28z)

<400> SEQUENCE: 18
atggccttac cagtgaccgc cttgctcctg ccgctggcct tgctgctcca cgccgccagg      60
ccggacatcc agatgaccca gtctccatcc ttcctgtctg catctgtagg agacagagtc     120
accatcactt gccgggccag tcagggcatt atcagttatt tagcctggta tcagcaaaaa     180
ccagagaaag cccctaagcg cctgatctat gctgcatcca gtttgcaaag tggggtccca     240
tcaaggttca gcggcagtgg atctgggaca gaattcactc tcacaatcag cagcctgcag     300
```

```
cctgaagatt ttgcaactta ctactgcggg cagtatgcca attatccgta cacctttggc    360
caaggtacga aactggaaat taaaggtgga ggtggttcgg gaggtggagg tagcggaggt    420
ggtggatctc aggtgcagct ggtgcagtct ggggctgagg tgaagaagcc tggggcctca    480
gtgaaggttt cctgcaaggc ttctggatac accttcacag ctactggat gaattgggtg     540 cgccaggccc ccgggcaagg cctggagtgg atggggaca tctacccggg cagtggtaac     600
acaaactacg atgagaagtt ccagggtaga gtcacgatga ccagggacac gtccatcagc    660
acagcctaca tggagctgag caggctgaga tctgacgaca cagccgtgta ctactgcgca    720
agaggtggat attatgaaga ttttgatagc tggggccaag gtaccactgt gaccgtgagc    780
tccctcgagc ccaaatcttg tgacaaaact cacacatgcc caccgtgccc ggatcccaaa    840
ttttgggtgc tggtggtggt tggtggagtc ctggcttgct atagcttgct agtaacagtg    900
gcctttatta ttttctgggt gaggagtaag aggagcaggc tcctgcacag tgactacatg    960
aacatgactc cccgccgccc cgggcccacc cgcaagcatt accagcccta tgccccacca   1020
cgcgacttcg cagcctatcg ctccagagtg aagttcagca ggagcgcaga cgcccccgcg   1080
tacaagcagg gccagaacca gctctataac gagctcaatc taggacgaag agaggagtac   1140
gatgttttgg acaagagacg tggccgggac cctgagatgg ggggaaagcc gagaaggaag   1200
aaccctcagg aaggcctgta caatgaactg cagaaagata gatggcgga ggcctacagt    1260 gagattggga tgaaaggcga gcgccggagg ggcaaggggc acgatggcct ttaccagggt   1320
ctcagtacag ccaccaagga cacctacgac gcccttcaca tgcaggccct gccccctcgc   1380
```

<210> SEQ ID NO 19
<211> LENGTH: 1452
<212> TYPE: DNA
<213> ORGANISM: Artificial Sequence
<220> FEATURE:
<223> OTHER INFORMATION: EphA3 CAR K085 (L2H BBz)

<400> SEQUENCE: 19

```
atggccttac cagtgaccgc cttgctcctg ccgctggcct tgctgctcca cgccgccagg     60
ccggacatcc agatgaccca gtctccatcc ttcctgtctg catctgtagg agacagagtc    120
accatcactt gccgggccag tcagggcatt atcagttatt tagcctggta tcagcaaaaa    180
ccagagaaag cccctaagcg cctgatctat gctgcatcca gtttgcaaag tggggtccca    240
tcaaggttca gcggcagtgg atctgggaca gaattcactc tcacaatcag cagcctgcag    300
cctgaagatt ttgcaactta ctactgcggg cagtatgcca attatccgta cacctttggc    360
caaggtacga aactggaaat taaaggtgga ggtggttcgg gaggtggagg tagcggaggt    420
ggtggatctc aggtgcagct ggtgcagtct ggggctgagg tgaagaagcc tggggcctca    480
gtgaaggttt cctgcaaggc ttctggatac accttcacag ctactggat gaattgggtg     540 cgccaggccc ccgggcaagg cctggagtgg atggggaca tctacccggg cagtggtaac     600
acaaactacg atgagaagtt ccagggtaga gtcacgatga ccagggacac gtccatcagc    660
acagcctaca tggagctgag caggctgaga tctgacgaca cagccgtgta ctactgcgca    720
agaggtggat attatgaaga ttttgatagc tggggccaag gtaccactgt gaccgtgagc    780
tccaccacta cccctgcacc gcgaccacca acaccggcgc caccattgc gtcgcagcct    840 ctgtccctgc gcccagaagc atgccgtcca gcagcaggtg gtgcagttca tactcgtggt    900
ctggatttcg cctgtgatat ctacatctgg gcgcccttgg ccgggacttg tggggtcctt    960
```

```
ctcctgtcac tggttatcac cctttactgc aaacggggca gaaagaaact cctgtatata    1020
ttcaaacaac catttatgag accagtacaa actactcaag aggaagatgg ctgtagctgc    1080
cgatttccag aagaagaaga aggaggatgt gaactgagag tgaagttcag caggagcgca    1140 gacgccccg cgtacaagca gggccagaac cagctctata cgagctcaa tctaggacga    1200 agagaggagt acgatgtttt ggacaagaga cgtggccggg accctgagat gggggggaaag   1260 ccgagaagga agaaccctca ggaaggcctg tacaatgaac tgcagaaaga taagatggcg    1320
gaggcctaca gtgagattgg gatgaaaggc gagcgccgga ggggcaaggg gcacgatggc    1380
ctttaccagg gtctcagtac agccaccaag gacacctacg acgcccttca catgcaggcc    1440
ctgccccctc gc                                                        1452

<210> SEQ ID NO 20
<211> LENGTH: 63
<212> TYPE: DNA
<213> ORGANISM: Artificial Sequence
<220> FEATURE:
<223> OTHER INFORMATION: CD8 leader

<400> SEQUENCE: 20
atggccttac cagtgaccgc cttgctcctg ccgctggcct tgctgctcca cgccgccagg    60
ccg                                                                  63

<210> SEQ ID NO 21
<211> LENGTH: 354
<212> TYPE: DNA
<213> ORGANISM: Artificial Sequence
<220> FEATURE:
<223> OTHER INFORMATION: EphA3 scFv heavy chain

<400> SEQUENCE: 21
caggtgcagc tggtgcagtc tggggctgag gtgaagaagc ctggggcctc agtgaaggtt    60
tcctgcaagg cttctggata caccttcaca ggctactgga tgaattgggt gcgccaggcc   120
cccgggcaag gcctggagtg gatggggac atctacccgg gcagtggtaa cacaaactac   180
gatgagaagt tccagggtag agtcacgatg accaggaca cgtccatcag cacagcctac   240
atggagctga gcaggctgag atctgacgac acagccgtgt actactgcgc aagaggtgga   300
tattatgaag attttgatag ctggggccaa ggtaccactg tgaccgtgag ctcc         354

<210> SEQ ID NO 22
<211> LENGTH: 45
<212> TYPE: DNA
<213> ORGANISM: Artificial Sequence
<220> FEATURE:
<223> OTHER INFORMATION: Linker

<400> SEQUENCE: 22
ggtggaggtg gttcgggagg tggaggtagc ggaggtggtg gatct                    45

<210> SEQ ID NO 23
<211> LENGTH: 321
<212> TYPE: DNA
<213> ORGANISM: Artificial Sequence
<220> FEATURE:
<223> OTHER INFORMATION: EphA3 scFv light chain

<400> SEQUENCE: 23
gacatccaga tgacccagtc tccatccttc ctgtctgcat ctgtaggaga cagagtcacc    60
atcacttgcc gggccagtca gggcattatc agttatttag cctggtatca gcaaaaacca   120
```

-continued

```
gagaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttacta ctgcgggcag tatgccaatt atccgtacac ctttggccaa    300
ggtacgaaac tggaaattaa a                                              321
```

<210> SEQ ID NO 24
<211> LENGTH: 135
<212> TYPE: DNA
<213> ORGANISM: Artificial Sequence
<220> FEATURE:
<223> OTHER INFORMATION: CD8 hinge

<400> SEQUENCE: 24

```
accactaccc ctgcaccgcg accaccaaca ccggcgccca ccattgcgtc gcagcctctg     60
tccctgcgcc cagaagcatg ccgtccagca gcaggtggtg cagttcatac tcgtggtctg    120
gatttcgcct gtgat                                                     135
```

<210> SEQ ID NO 25
<211> LENGTH: 72
<212> TYPE: DNA
<213> ORGANISM: Artificial Sequence
<220> FEATURE:
<223> OTHER INFORMATION: CD8 TM

<400> SEQUENCE: 25

```
atctacatct gggcgccctt ggccgggact tgtggggtcc ttctcctgtc actggttatc     60
accctttact gc                                                         72
```

<210> SEQ ID NO 26
<211> LENGTH: 126
<212> TYPE: DNA
<213> ORGANISM: Artificial Sequence
<220> FEATURE:
<223> OTHER INFORMATION: 41BB

<400> SEQUENCE: 26

```
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126
```

<210> SEQ ID NO 27
<211> LENGTH: 57
<212> TYPE: DNA
<213> ORGANISM: Artificial Sequence
<220> FEATURE:
<223> OTHER INFORMATION: CD28 hinge

<400> SEQUENCE: 27

```
ctcgagccca atcttgtga caaaactcac acatgcccac cgtgcccgga tccaaa          57
```

<210> SEQ ID NO 28
<211> LENGTH: 81
<212> TYPE: DNA
<213> ORGANISM: Artificial Sequence
<220> FEATURE:
<223> OTHER INFORMATION: CD28 TM

<400> SEQUENCE: 28

```
ttttgggtgc tggtggtggt tggtggagtc ctggcttgct atagcttgct agtaacagtg     60
```

```
gcctttatta ttttctgggt g                                             81
```

<210> SEQ ID NO 29
<211> LENGTH: 123
<212> TYPE: DNA
<213> ORGANISM: Artificial Sequence
<220> FEATURE:
<223> OTHER INFORMATION: CD28

<400> SEQUENCE: 29

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 30
<211> LENGTH: 336
<212> TYPE: DNA
<213> ORGANISM: Artificial Sequence
<220> FEATURE:
<223> OTHER INFORMATION: CD3z

<400> SEQUENCE: 30

```
agagtgaagt tcagcaggag cgcagacgcc cccgcgtaca gcagggccca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 31
<211> LENGTH: 5
<212> TYPE: PRT
<213> ORGANISM: Artificial Sequence
<220> FEATURE:
<223> OTHER INFORMATION: humanized anti-EGFRvIII binding domain VH CDR1

<400> SEQUENCE: 31

```
Asp Tyr Tyr Ile His
1               5
```

<210> SEQ ID NO 32
<211> LENGTH: 17
<212> TYPE: PRT
<213> ORGANISM: Artificial Sequence
<220> FEATURE:
<223> OTHER INFORMATION: humanized anti-EGFRvIII binding domain VH CDR2

<400> SEQUENCE: 32

```
Arg Ile Asp Pro Glu Asn Asp Glu Thr Lys Tyr Gly Pro Ile Phe Gln
1               5                   10                  15

Gly
```

<210> SEQ ID NO 33
<211> LENGTH: 5
<212> TYPE: PRT
<213> ORGANISM: Artificial Sequence
<220> FEATURE:
<223> OTHER INFORMATION: humanized anti-EGFRvIII binding domain VH CDR3

<400> SEQUENCE: 33

```
Arg Gly Gly Val Tyr
```

<210> SEQ ID NO 34
<211> LENGTH: 16
<212> TYPE: PRT
<213> ORGANISM: Artificial Sequence
<220> FEATURE:
<223> OTHER INFORMATION: humanized anti-EGFRvIII binding domain VL CDR1

<400> SEQUENCE: 34

Lys Ser Ser Gln Ser Leu Leu Asp Ser Asp Gly Lys Thr Tyr Leu Asn
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: humanized anti-EGFRvIII binding domain VL CDR2

<400> SEQUENCE: 35

Leu Val Ser Lys Leu Asp Ser
1               5

<210> SEQ ID NO 36
<211> LENGTH: 9
<212> TYPE: PRT
<213> ORGANISM: Artificial Sequence
<220> FEATURE:
<223> OTHER INFORMATION: humanized anti-EGFRvIII binding domain VL CDR3

<400> SEQUENCE: 36

Trp Gln Gly Thr His Phe Pro Gly Thr
1               5

<210> SEQ ID NO 37
<211> LENGTH: 246
<212> TYPE: PRT
<213> ORGANISM: Artificial Sequence
<220> FEATURE:
<223> OTHER INFORMATION: humanized anti-EGFRvIII binding domain single
      chain variable fragment of monoclonal antibody clone 3C10

<400> SEQUENCE: 37

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

```
Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
            165                 170                 175

Gln Lys Pro Gly Gln Pro Pro Lys Arg Leu Ile Ser Leu Val Ser Lys
        180                 185                 190

Leu Asp Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
        210                 215                 220

Tyr Tyr Cys Trp Gln Gly Thr His Phe Pro Gly Thr Phe Gly Gly Gly
225                 230                 235                 240

Thr Lys Val Glu Ile Lys
            245

<210> SEQ ID NO 38
<211> LENGTH: 24
<212> TYPE: PRT
<213> ORGANISM: Artificial Sequence
<220> FEATURE:
<223> OTHER INFORMATION: humanized anti-EGFRvIII transmembrane domain

<400> SEQUENCE: 38

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 39
<211> LENGTH: 45
<212> TYPE: PRT
<213> ORGANISM: Artificial Sequence
<220> FEATURE:
<223> OTHER INFORMATION: humanized anti-EGFRvIII hinge region

<400> SEQUENCE: 39

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 40
<211> LENGTH: 56
<212> TYPE: PRT
<213> ORGANISM: Artificial Sequence
<220> FEATURE:
<223> OTHER INFORMATION: CD3 zeta domain

<400> SEQUENCE: 40

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu
    50                  55
```

```
<210> SEQ ID NO 41
<211> LENGTH: 111
<212> TYPE: PRT
<213> ORGANISM: Artificial Sequence
<220> FEATURE:
<223> OTHER INFORMATION: primary signaling domain

<400> SEQUENCE: 41

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Leu Tyr Asn Glu Leu Gln Lys Asp
    50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110

<210> SEQ ID NO 42
<211> LENGTH: 1476
<212> TYPE: DNA
<213> ORGANISM: Artificial Sequence
<220> FEATURE:
<223> OTHER INFORMATION: human EGFRvIII-targeting chimeric antigen
      receptor 3C10-41BBz

<400> SEQUENCE: 42
atggccttac cagttaccgc cttattattg cctttagcct tattgttaca tgccgcccgt     60
ccgggatccg agattcagct gcagcaatct ggggcagaaa ttgtgaagcc aggggcctca    120
gtcaagctgt cctgcacagg ttctggcttc aacattgaag actactatat tcactgggtg    180
aagcagagga ctgaacaggg cctggaatgg attggaagga ttgatcctga gaatgatgaa    240
actaaatatg cccaatatat ccagggcagg gccactaaa cagcagacac atcctccaac    300
acagtctacc tgcaactcag cagcctgaca tctgaggaca ctgccgtcta ttactgtgcc    360
tttcgcggtg gagtctactg ggggccagga accactctca cagtctcctc aggaggtggt    420
ggttccggtg gtggtggttc cggaggtggt ggttcacata tggatgttgt gatgacccag    480
tctccactca ctctatcggt tgccattgga caatcagcct ccatctcttg caagtcaagt    540
cagagcctct tagatagtga tggaaagaca tatttgaatt ggttgttaca gaggccaggc    600
cagtctccaa agcgcctaat ctctctggtg tctaaactgg actctggagt ccctgacagg    660
ttcactggca gtggatcagg acagatttc acactgagaa tcagcagagt ggaggctgag    720
gatttgggaa tttattattg ctggcaaggt acacatttc tgggacgtt cggtggaggg    780 accaagctgg agataaaagc tagcaccact cccctgcac cgcgaccacc aacaccggcg    840
cccaccattg cgtcgcagcc tctgtccctg cgcccagaag catgccgtcc agcagcaggt    900
ggtgcagttc atactcgtgg tctggatttc gcctgtgata tctacatctg gcgcccttg    960 gccgggactt gtgggtcct tctcctgtca ctggttatca ccctttactg caaacggggc   1020
agaaagaaac tcctgtatat attcaaacaa ccatttatga gaccagtaca aactactcaa   1080
gaggaagatg gctgtagctg ccgatttcca gaagaagaag aaggaggatg tgaactgaga   1140
```

```
gtgaagttca gcaggagcgc agacgccccc gcgtacaagc agggccagaa ccagctctat    1200
aacgagctca atctaggacg aagagaggag tacgatgttt tggacaagag acgtggccgg    1260
gaccctgaga tgggggaaa gccgagaagg aagaaccctc aggaaggcct gtacaatgaa    1320
ctgcagaaag ataagatggc ggaggcctac agtgagattg ggatgaaagg cgagcgccgg    1380
aggggcaagg ggcacgatgg cctttaccag ggtctcagta cagccaccaa ggacacctac    1440 gacgccttc acatgcaggc cctgccccct cgctaa                               1476
```

<210> SEQ ID NO 43
<211> LENGTH: 491
<212> TYPE: PRT
<213> ORGANISM: Artificial Sequence
<220> FEATURE:
<223> OTHER INFORMATION: human EGFRvIII-targeting chimeric antigen
      receptor 3C10-41BBz

<400> SEQUENCE: 43

```
Met Ala Leu Pro Val Thr Ala Leu Leu Leu Pro Leu Ala Leu Leu Leu
1               5                   10                  15

His Ala Ala Arg Pro Gly Ser Glu Ile Gln Leu Gln Gln Ser Gly Ala
            20                  25                  30

Glu Leu Val Lys Pro Gly Ala Ser Val Lys Leu Ser Cys Thr Gly Ser
        35                  40                  45

Gly Phe Asn Ile Glu Asp Tyr Tyr Ile His Trp Val Lys Gln Arg Thr
    50                  55                  60

Glu Gln Gly Leu Glu Trp Ile Gly Arg Ile Asp Pro Glu Asn Asp Glu
65                  70                  75                  80

Thr Lys Tyr Gly Pro Ile Phe Gln Gly Arg Ala Thr Ile Thr Ala Asp
                85                  90                  95

Thr Ser Ser Asn Thr Val Tyr Leu Gln Leu Ser Ser Leu Thr Ser Glu
            100                 105                 110

Asp Thr Ala Val Tyr Tyr Cys Ala Phe Arg Gly Gly Val Tyr Trp Gly
        115                 120                 125

Pro Gly Thr Thr Leu Thr Val Ser Ser Gly Gly Gly Ser Gly Gly
    130                 135                 140

Gly Gly Ser Gly Gly Gly Ser His Met Asp Val Val Met Thr Gln
145                 150                 155                 160

Ser Pro Leu Thr Leu Ser Val Ala Ile Gly Gln Ser Ala Ser Ile Ser
                165                 170                 175

Cys Lys Ser Ser Gln Ser Leu Leu Asp Ser Asp Gly Lys Thr Tyr Leu
            180                 185                 190

Asn Trp Leu Leu Gln Arg Pro Gly Gln Ser Pro Lys Arg Leu Ile Ser
        195                 200                 205

Leu Val Ser Lys Leu Asp Ser Gly Val Pro Asp Arg Phe Thr Gly Ser
    210                 215                 220

Gly Ser Gly Thr Asp Phe Thr Leu Arg Ile Ser Arg Val Glu Ala Glu
225                 230                 235                 240

Asp Leu Gly Ile Tyr Tyr Cys Trp Gln Gly Thr His Phe Pro Gly Thr
                245                 250                 255

Phe Gly Gly Gly Thr Lys Leu Glu Ile Lys Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300
```

```
Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 44
<211> LENGTH: 9
<212> TYPE: PRT
<213> ORGANISM: Artificial Sequence
<220> FEATURE:
<223> OTHER INFORMATION: human EphA3 single chain variable fragment VH
      CDR3

<400> SEQUENCE: 44

Gly Gly Tyr Tyr Glu Asp Phe Asp Ser
1               5

<210> SEQ ID NO 45
<211> LENGTH: 9
<212> TYPE: PRT
<213> ORGANISM: Artificial Sequence
<220> FEATURE:
<223> OTHER INFORMATION: human EphA3 single chain variable fragment VL
      CDR3

<400> SEQUENCE: 45

Gly Gln Tyr Ala Asn Tyr Pro Tyr Thr
1               5

<210> SEQ ID NO 46
<211> LENGTH: 118
<212> TYPE: PRT
<213> ORGANISM: Artificial Sequence
<220> FEATURE:
<223> OTHER INFORMATION: extracellular anti-human EphA3 binding domain
      VH

<400> SEQUENCE: 46

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Tyr Glu Asp Phe Asp Ser Trp Gly Gln Gly Thr
                100                 105                 110

Thr Val Thr Val Ser Ser
            115
```

<210> SEQ ID NO 47
<211> LENGTH: 107
<212> TYPE: PRT
<213> ORGANISM: Artificial Sequence
<220> FEATURE:
<223> OTHER INFORMATION: extracellular anti-human EphA3 binding domain
      VL

<400> SEQUENCE: 47

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gly Gln Tyr Ala Asn Tyr Pro Tyr
                85                  90                  95

Thr Phe Gly Gln Gly Thr Lys Leu Glu Ile Lys
                100                 105
```

<210> SEQ ID NO 48
<211> LENGTH: 5
<212> TYPE: PRT
<213> ORGANISM: Artificial Sequence
<220> FEATURE:
<223> OTHER INFORMATION: extracellular anti-human EphA3 binding domain
      VH CDR1

<400> SEQUENCE: 48

```
Ser Tyr Trp Ile Asn
1               5
```

<210> SEQ ID NO 49
<211> LENGTH: 17
<212> TYPE: PRT
<213> ORGANISM: Artificial Sequence
<220> FEATURE:
<223> OTHER INFORMATION: extracellular anti-human EphA3 binding domain
      VH CDR2

<400> SEQUENCE: 49

```
Asp Ile Tyr Pro Gly Ser Gly Asn Thr Asn Tyr Asp Glu Lys Phe Lys
```

```
1               5                   10                  15
Arg

<210> SEQ ID NO 50
<211> LENGTH: 9
<212> TYPE: PRT
<213> ORGANISM: Artificial Sequence
<220> FEATURE:
<223> OTHER INFORMATION: extracellular anti-human EphA3 binding domain
      VH CDR3

<400> SEQUENCE: 50

Ser Gly Tyr Tyr Glu Asp Phe Asp Ser
1               5

<210> SEQ ID NO 51
<211> LENGTH: 11
<212> TYPE: PRT
<213> ORGANISM: Artificial Sequence
<220> FEATURE:
<223> OTHER INFORMATION: extracellular anti-human EphA3 binding domain
      VL CDR1

<400> SEQUENCE: 51

Arg Ala Ser Gln Glu Ile Ser Gly Tyr Leu Gly
1               5                   10

<210> SEQ ID NO 52
<211> LENGTH: 7
<212> TYPE: PRT
<213> ORGANISM: Artificial Sequence
<220> FEATURE:
<223> OTHER INFORMATION: extracellular anti-human EphA3 binding domain
      VL CDR2

<400> SEQUENCE: 52

Ala Ala Ser Thr Leu Asp Ser
1               5

<210> SEQ ID NO 53
<211> LENGTH: 9
<212> TYPE: PRT
<213> ORGANISM: Artificial Sequence
<220> FEATURE:
<223> OTHER INFORMATION: extracellular anti-human EphA3 binding domain
      VL CDR3

<400> SEQUENCE: 53

Val Gln Tyr Ala Asn Tyr Pro Tyr Thr
1               5

<210> SEQ ID NO 54
<211> LENGTH: 1183
<212> TYPE: DNA
<213> ORGANISM: Artificial Sequence
<220> FEATURE:
<223> OTHER INFORMATION: EF1 alpha promoter

<400> SEQUENCE: 54
gtgaggctcc ggtgcccgtc agtgggcaga gcgcacatcg cccacagtcc ccgagaagtt     60
ggggggaggg gtcggcaatt gaaccggtgc ctagagaagg tggcgcgggg taaactggga    120
aagtgatgtc gtgtactggc tccgcctttt tcccgagggt gggggagaac cgtatataag    180
tgcagtagtc gccgtgaacg ttctttttcg caacgggttt gccgccagaa cacaggtaag    240
tgccgtgtgt ggttcccgcg ggcctggcct ctttacgggt tatggccctt gcgtgccttg    300
```

```
aattacttcc acctggctgc agtacgtgat tcttgatccc gagcttcggg ttggaagtgg      360
gtgggagagt tcgaggcctt gcgcttaagg agccccttcg cctcgtgctt gagttgaggc      420
ctggcctggg cgctggggcc gccgcgtgcg aatctggtgg caccttcgcg cctgtctcgc      480
tgctttcgat aagtctctag ccatttaaaa ttttgatga cctgctgcga cgcttttttt      540
ctggcaagat agtcttgtaa atgcgggcca agatctgcac actggtattt cggttttgg      600 ggccgcgggc ggcgacgggg cccgtgcgtc cagcgcaca tgttcggcga ggcggggcct      660
gcgagcgcgg ccaccgagaa tcggacgggg gtagtctcaa gctggccggc ctgctctggt      720
gcctggcctc gcgccgccgt gtatcgcccc gccctgggcg gcaaggctgg cccggtcggc      780
accagttgcg tgagcggaaa gatggccgct tcccggccct gctgcaggga gctcaaaatg      840
gaggacgcgg cgctcgggag agcgggcggg tgagtcaccc acacaaagga aaagggcctt      900
tccgtcctca gccgtcgctt catgtgactc cacggagtac cgggcgccgt ccaggcacct      960
cgattagttc tcgagctttt ggagtacgtc gtctttaggt tggggggagg ggttttatgc     1020
gatggagttt ccccacactg agtgggtgga gactgaagtt aggccagctt ggcacttgat     1080
gtaattctcc ttggaatttg ccctttttga gtttggatct tggttcattc tcaagcctca     1140
gacagtggtt caaagttttt ttcttccatt tcaggtgtcg tga                       1183
```

<210> SEQ ID NO 55
<211> LENGTH: 1401
<212> TYPE: DNA
<213> ORGANISM: Artificial Sequence
<220> FEATURE:
<223> OTHER INFORMATION: CD8 leader, single chain variable fragment
      (scFv) of anti-human EphA3 monoclonal antibody ifabotuzumab (Ifab
      scFv) and CD8 hinge

<400> SEQUENCE: 55

```
gctagctcta gaatggcctt accagtgacc gccttgctcc tgccgctggc cttgctgctc       60
cacgccgcca ggccggacat ccagatgacc cagtctccat ccttcctgtc tgcatctgta      120
ggagacagag tcaccatcac ttgccggggcc agtcagggca ttatcagtta tttagcctgg      180
tatcagcaaa accagagaa agcccctaag cgcctgatct atgctgcatc cagtttgcaa      240
agtggggtcc catcaaggtt cagcggcagt ggatctggga cagaattcac tctcacaatc      300
agcagcctgc agcctgaaga ttttgcaact tactactgcg gcagtatgc caattatccg      360 tacacctttg gccaaggtac gaaactggaa attaaaggtg gaggtggttc gggaggtgga      420
ggtagcggag gtggtggatc tcaggtgcag ctggtgcagt ctggggctga ggtgaagaag      480
cctggggcct cagtgaaggt ttcctgcaag gcttctggat acaccttcac aggctactgg      540
atgaattggg tgcgccaggc ccccgggcaa ggcctggagt ggatggggga catctacccg      600
ggcagtggta acacaaacta cgatgagaag ttccagggta gagtcacgat gaccagggac      660
acgtccatca gcacagccta catggagctg agcaggctga gatctgacga cacagccgtg      720
tactactgcg caagaggtgg atattatgaa gattttgata gctgggccca aggtaccact      780
gtgaccgtga gctccctcga gcccaaatct tgtgacaaaa ctcacacatg cccaccgtgc      840
ccggatccca aatttggggt gctggtggtg ttggtggag tcctggcttg ctatagcttg      900
ctagtaacag tggcctttat tattttctgg gtgaggagta agaggagcag gctcctgcac      960
agtgactaca tgaacatgac tccccgccgc cccgggccca cccgcaagca ttaccagccc     1020
tatgccccac cacgcgactt cgcagcctat cgctccagag tgaagttcag caggagcgca     1080
```

```
gacgccccg  cgtacaagca  gggccagaac  cagctctata  acgagctcaa  tctaggacga    1140
agagaggagt  acgatgtttt  ggacaagaga  cgtggccggg  accctgagat  gggggggaaag   1200 ccgagaagga  agaaccctca  ggaaggcctg  tacaatgaac  tgcagaaaga  taagatggcg    1260
gaggcctaca  gtgagattgg  gatgaaaggc  gagcgccgga  ggggcaaggg  gcacgatggc    1320
ctttaccagg  gtctcagtac  agccaccaag  gacacctacg  acgcccttca  catgcaggcc    1380
ctgccccctc  gctaagtcga  c                                                1401
```

EphA3 DIRECTED CAR-T CELLS FOR TREATMENT OF TUMORS

CROSS-REFERENCE TO RELATED APPLICATIONS

This application claims priority to U.S. Provisional Application No. 62/933,354, filed Nov. 8, 2019, which is hereby incorporated by reference.

SEQUENCE LISTING INCORPORATION

The ".txt" Sequence Listing filed with this application by EFS and which is entitled P-589366-US-SQL_ST25-08NOV20.txt, is 33 kilobytes in size and which was created on Nov. 8, 2020, is hereby incorporated by reference.

FIELD OF THE INVENTION

This invention relates to chimeric antigen receptors (CARs) targeting human EphA3 and binding thereto and to dual targeting CARs that bind to human EphA3 and to human mutant epidermal growth factor receptor variant III (EGFRvIII). This invention also relates to CAR-T cells comprising the CARs targeting human EphA3 and binding thereto and to CAR-T cells comprising the dual targeting CARs that bind to human EphA3 and to human EGFRVIII. This invention further relates to methods for treating a solid tumor cancer, the methods comprising administering to a subject in need thereof a pharmaceutical composition comprising the CAR-T cells comprising the CARs targeting human EphA3 and binding thereto or the CAR-T cells comprising the dual targeting CARs that bind to human EphA3 and to human EGFRvIII.

BACKGROUND OF THE INVENTION

Efficacy of chimeric antigen receptor T cell (CART) therapy remains limited in solid tumors. Given the heterogeneity of surface receptor expression and immunosuppressive stromal microenvironment, strategies to target and disrupt tumor neovasculature and tumor stroma are needed to help overcome CART inhibition in solid tumors including glioblastoma multiforme (GBM). Eph receptors are the largest family of receptor tyrosine kinases and are integral to cell adhesion, migration, and axon guidance during development and homeostasis. EphA3 is a receptor tyrosine kinase which is poorly expressed in adult tissues but is highly expressed in tumor neovasculature and tumor stromal cells in GBM and other solid tumors. EphA3 is overexpressed in up to 40% of GBM samples and is overexpressed in the tumor stroma and tumor vasculature of other solid tumors including pancreatic, prostate, breast, colon, melanoma, myeloma, bladder, kidney and liver tumors, lung cancer, e.g., small cell lung cancer (SCLC) or non-small cell lung cancer (NSCLC).

Surgical removal of solid GBM tumors, temozolomide chemotherapy and radiation prolong survival by up to five years in about 7% of patients. Current therapies for GBM are not curative. In light of the inadequacies of surgery and current drugs and therapies for GBM and other solid tumors, there exists a critical need for improved compositions and therapeutically effective methods to treat solid tumor cancers, to reduce solid tumor cancer relapse rate or prevent occurrence of solid tumor cancer relapse in patients having or who have had a solid tumor cancer. The present invention provides CART cells directed against EphA3 to use in targeting tumor neovasculature and tumor stromal cells in solid tumors including GBM, pancreatic, prostate, breast, colon, melanoma, myeloma, lung, bladder, kidney and liver tumors.

SUMMARY OF THE INVENTION

In one aspect, the present invention provides a chimeric antigen receptor (CAR) that binds to human Eph receptor A3 (EphA3), the CAR comprising an extracellular anti-human EphA3 binding domain comprising a single chain variable fragment (scFv) of anti-human EphA3 monoclonal antibody ifabotuzumab, wherein the human EphA3 scFv comprises a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2.

In another aspect, the present invention provides a CAR construct that binds to human EphA3 comprising: (a) a single chain variable fragment (scFv) of monoclonal antibody ifabotuzumab that binds to human EphA3, the scFv comprising a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2; wherein the $V_H$ and the $V_L$ are attached by a linker peptide comprising an amino acid sequence of SEQ ID NO: 4; (b) a hinge region comprising a CD8 hinge region comprises an amino acid sequence of SEQ ID NO: 5 or a CD28 hinge region comprises an amino acid sequence of SEQ ID NO: 6. (c) a transmembrane domain, and (d) an intracellular signaling domain comprising a costimulatory domain and an activation domain.

In an aspect, the present invention provides a method for producing a human EphA3-targeting CAR T-cell, the method comprising transducing a T-cell with the herein provided EphA3 CAR expression cassette.

In another aspect, the present invention provides methods for treating a solid tumor cancer, the methods comprising administering to a subject in need thereof a pharmaceutical composition comprising the herein provided human EphA3-targeting CAR-T cells.

In one aspect, the present invention provides a dual targeting CAR-T cell that binds to human EphA3 and to human mutant epidermal growth factor receptor variant III (EGFRvIII), the CAR-T cell comprising: a first CAR construct that binds to human Eph receptor A3 (EphA3), the CAR comprising an extracellular anti-human EphA3 binding domain comprising a human EphA3 single chain variable fragment (scFv) of anti-EphA3 monoclonal antibody ifabotuzumab, wherein the human EphA3 scFv comprises a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2, wherein the scFv of monoclonal antibody ifabotuzumab that binds to human EphA3, is fused in tandem to a hinge region, a transmembrane domain; and an intracellular signaling domain comprising a costimulatory domain and a activation domain; and a second CAR construct that binds to human mutant epidermal growth factor receptor variant III (EGFRvIII) comprising a humanized anti-EGFRvIII binding domain, wherein the humanized anti-EGFRvIII binding domain comprises: (a) a heavy chain immunoglobulin variable region comprising: (i) a CDR1 comprising amino acid sequence DYYIH (SEQ ID NO: 31); (ii) a CDR2 comprising amino acid sequence RIDPENDETKYGPIFQG (SEQ ID NO: 32); and (iii) a CDR3 comprising amino acid sequence RGGVY (SEQ ID NO: 33); and (b) a light chain immunoglobulin variable region comprising: (i) a CDR1 comprising amino acid sequence KSSQSLLDSDGKTYLN (SEQ ID NO: 34); (ii) a CDR2 comprising the sequence LVSKLDS (SEQ ID NO: 35); and (iii) a CDR3 comprising amino acid sequence WQGTHFPGT (SEQ ID NO: 36).

In another aspect, the present invention provides a method for producing a dual targeting CAR-T cell that binds to human EphA3 and human EGFRvIII, the method comprising: (a) transducing a T-cell with an EphA3-targeting CAR expression cassette comprising a CAR that binds to human EphA3 and is encoded by an isolated nucleic acid sequence of SEQ ID NO: 16, SEQ ID NO: 17, SEQ ID NO: 18 or SEQ ID NO: 19 to produce a human EphA3-targeting CAR T-cell; and (b) transducing the human EphA3-targeting CAR T-cell produced in step (a) with an expression cassette comprising a human EGFRvIII-targeting CAR that binds to human EGFRvIII and the human EGFRvIII-targeting CAR is encoded by a nucleic acid sequence of SEQ ID NO: 42:

ATGGCCTTACCAGTTACCGCCTTATTATTGCCTTTAGCCTTATTGTTAC

ATGCCGCCCGTCCGGGATCCGAGATTCAGCTGCAGCAATCTGGGGCAGA

ACTTGTGAAGCCAGGGGCCTCAGTCAAGCTGTCCTGCACAGGTTCTGGC

TTCAACATTGAAGACTACTATATTCACTGGGTGAAGCAGAGGACTGAAC

AGGGCCTGGAATGGATTGGAAGGATTGATCCTGAGAATGATGAAACTAA

ATATGGCCCAATATTCCAGGGCAGGGCCACTATAACAGCAGACACATCC

TCCAACACAGTCTACCTGCAACTCAGCAGCCTGACATCTGAGGACACTG

CCGTCTATTACTGTGCCTTTCGCGGTGGAGTCTACTGGGGGCCAGGAAC

CACTCTCACAGTCTCCTCAGGAGGTGGTGGTTCCGGTGGTGGTGGTTCC

GGAGGTGGTGGTTCACATATGGATGTTGTGATGACCCAGTCTCCACTCA

CTCTATCGGTTGCCATTGGACAATCAGCCTCCATCTCTTGCAAGTCAAG

TCAGAGCCTCTTAGATAGTGATGGAAAGACATATTTGAATTGGTTGTTA

CAGAGGCCAGGCCAGTCTCCAAAGCGCCTAATCTCTCTGGTGTCTAAAC

TGGACTCTGGAGTCCCTGACAGGTTCACTGGCAGTGGATCAGGGACAGA

TTTCACACTGAGAATCAGCAGAGTGGAGGCTGAGGATTTGGGAATTTAT

TATTGCTGGCAAGGTACACATTTTCCTGGGACGTTCGGTGGAGGGACCA

AGCTGGAGATAAAAGCTAGCACCACTACCCCTGCACCGCGACCACCAAC

ACCGGCGCCCACCATTGCGTCGCAGCCTCTGTCCCTGCGCCCAGAAGCA

TGCCGTCCAGCAGCAGGTGGTGCAGTTCATACTCGTGGTCTGGATTTCG

CCTGTGATATCTACATCTGGGCGCCCTTGGCCGGGACTTGTGGGGTCCT

TCTCCTGTCACTGGTTATCACCCTTTACTGCAAACGGGGCAGAAAGAAA

CTCCTGTATATATTCAAACAACCATTTATGAGACCAGTACAAACTACTC

AAGAGGAAGATGGCTGTAGCTGCCGATTTCCAGAAGAAGAAGAAGGAGG

ATGTGAACTGAGAGTGAAGTTCAGCAGGAGCGCAGACGCCCCCGCGTAC

AAGCAGGGCCAGAACCAGCTCTATAACGAGCTCAATCTAGGACGAAGAG

AGGAGTACGATGTTTTGGACAAGAGACGTGGCCGGGACCCTGAGATGGG

GGGAAAGCCGAGAAGGAAGAACCCTCAGGAAGGCCTGTACAATGAACTG

CAGAAAGATAAGATGGCGGAGGCCTACAGTGAGATTGGGATGAAAGGCG

AGCGCCGGAGGGGCAAGGGGCACGATGGCCTTTACCAGGGTCTCAGTAC

AGCCACCAAGGACACCTACGACGCCCTTCACATGCAGGCCCTGCCCCCT

CGCTAA to produce a human EphA3-targeting- and a human EGFRvIII-targeting-CAR T-cell, wherein the human EphA3-targeting- and human EGFRvIII-targeting-CAR T-cell expresses the human EphA3-targeting CAR and the human EGFRvIII-targeting CAR on a cell surface thereof.

In additional aspects, the present invention provides a pharmaceutical composition comprising the herein provided dual targeting CAR-T cell that binds to human EphA3 and to human mutant EGFRvIII and a pharmaceutically acceptable carrier.

In additional aspects, the present invention provides a pharmaceutical composition comprising a CAR-T cell that binds to human EphA3 and a pharmaceutical composition comprising CAR-T cell that binds to human mutant EGFRvIII, wherein each pharmaceutical composition is administered to a subject in need thereof together (concurrently) or sequentially.

In other aspects, the present invention provides a chimeric antigen receptor (CAR) construct that binds to human Eph receptor A3 (EphA3), the CAR comprising an extracellular anti-human EphA3 binding domain comprising a human EphA3 single chain variable fragment (scFv) of anti-EphA3 monoclonal antibody, wherein the human EphA3 scFv comprises CDR3 of the $V_H$ region comprises GGYYEDFDS (SEQ ID NO:44) and the CDR3 of the $V_L$ region comprises GQYANYPYT (SEQ ID NO:45).

In another aspect, the present invention provides a CAR construct that binds to human Eph receptor A3 (EphA3), the CAR construct comprising an extracellular anti-human EphA3 binding domain comprising: a $V_H$ region comprising amino acid sequence (SEQ ID NO: 46)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS and a $V_L$ region comprising amino acid sequence (SEQ ID NO: 47)
DIQMTQSPSFLSASVGDRVTITCRASQGIISYLAWYQQKPEKAPKRLIY

AASSLQSGVPSRFSGSGSGTEFTLTISSLQPEDFATYYCGQYANYPYTF

GQGTKLEIK.

In one aspect, the present invention provides a CAR construct that binds to human Eph receptor A3 (EphA3), the CAR construct comprising an extracellular anti-human EphA3 binding domain comprising: a $V_H$ region CDR1 having a sequence SYWIN (SEQ ID NO:48), a $V_H$ region CDR2 having a sequence DIYPGSGNTNYDEKFKR (SEQ ID NO:49), a $V_H$ region CDR3 having a sequence SGYYEDFDS (SEQ ID NO:50), and a $V_L$ region CDR1 having a sequence RASQEISGYLG (SEQ ID NO:51), a $V_L$ region CDR2 having a sequence AASTLDS (SEQ ID NO:52), and a $V_L$ region CDR3 having a sequence VQYANYPYT (SEQ ID NO:53).

Other features and advantages of the present invention will become apparent from the following detailed description, examples and figures. It should be understood, however, that the detailed description and the specific examples while indicating certain embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIGS. 5A-5D show CAR-T cell production of the EGFRviii targeting CAR (termed K96 or K096) on the surface of donor T-cells via flow cytometry (FIGS. 5A-5C) and a map of the EGFRviii targeting CAR construct termed K96 (FIG. 5D).

Figure 24:
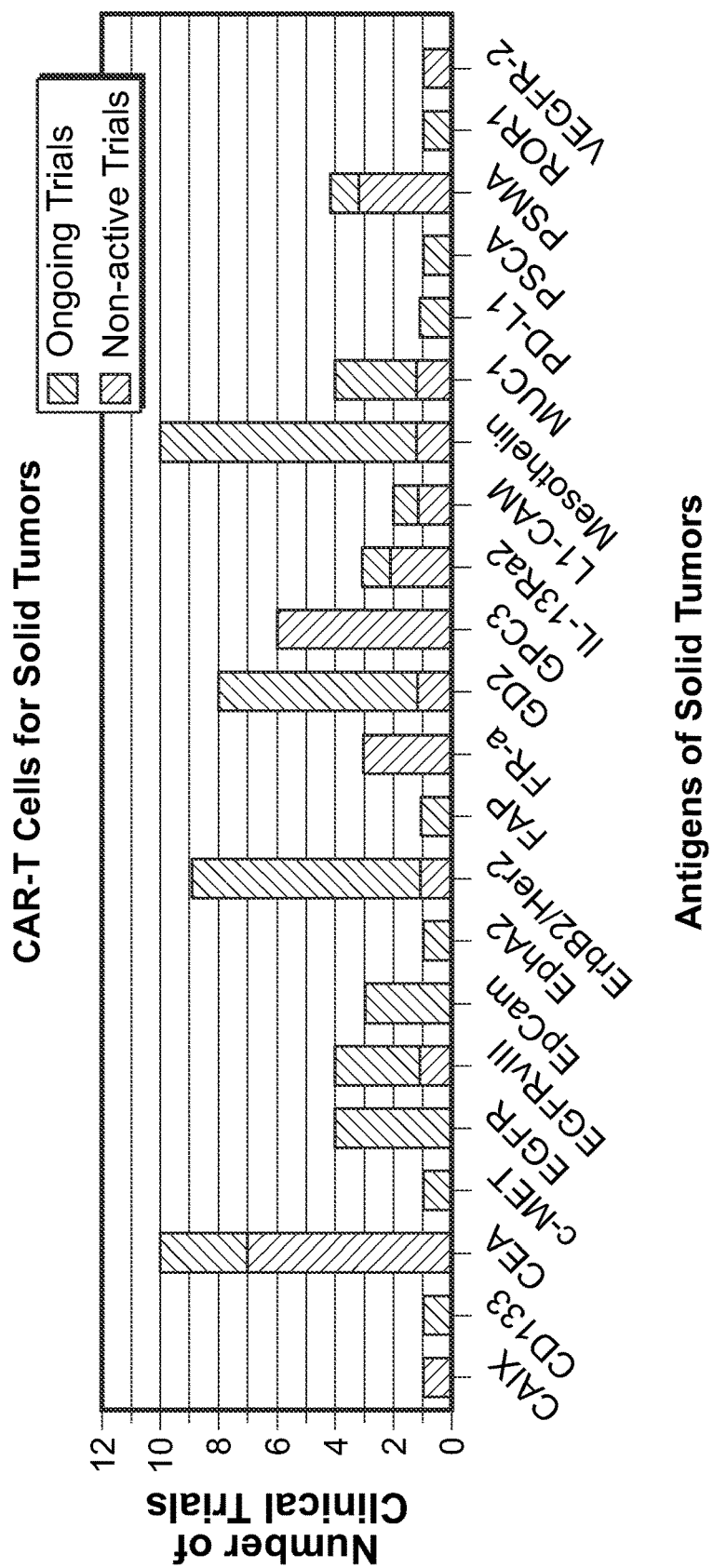
FIG. 24 shows the CAR-T cells for solid tumors in ongoing trials or non-active trials adapted from Hartman et al. EMBO Mol Med. 2017 September; 9(9):1183-1197.

The human EphA3-targeting CAR-T cells described herein are administered (via a pharmaceutical composition comprising the human EphA3-targeting CAR-T cells) as either an adjuvant or in combination with two or more pharmaceutical compositions comprising the CAR-T cells for solid tumors in FIG. 24.

Figure 25:
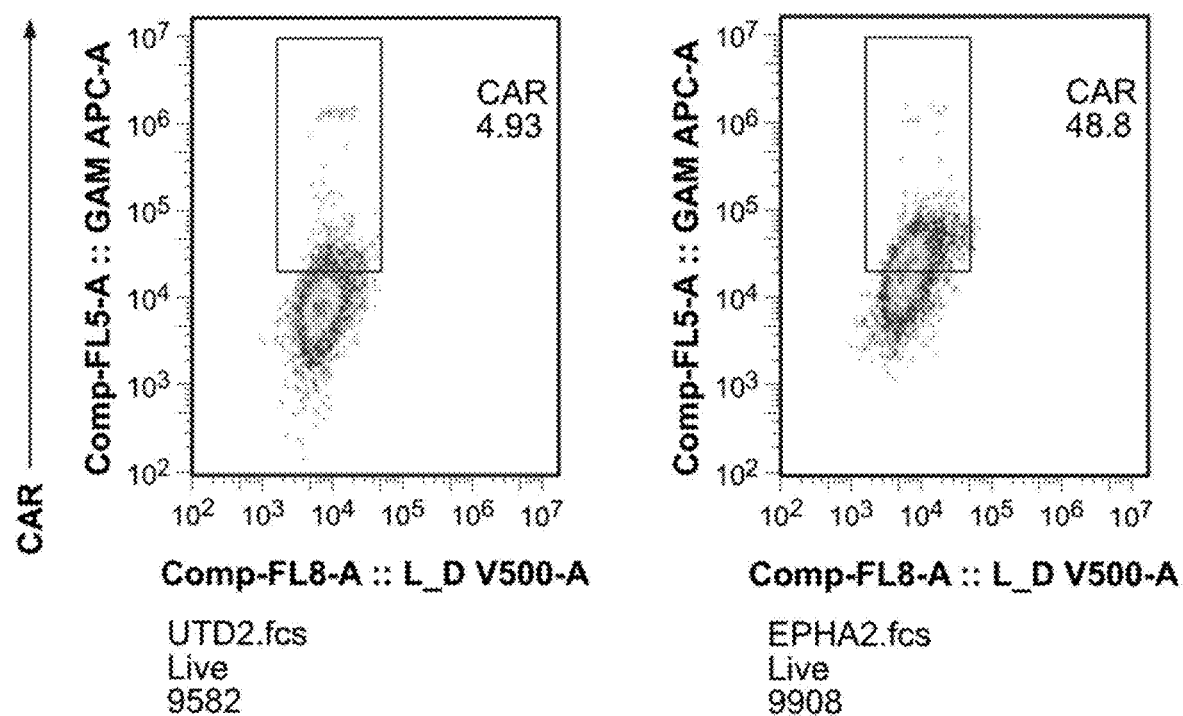

FIG. 25 shows EphA3 CAR expression on transduced T-cells (right) compared to untransduced T-cells (Left). Construct map (bottom).

Figure 26A:
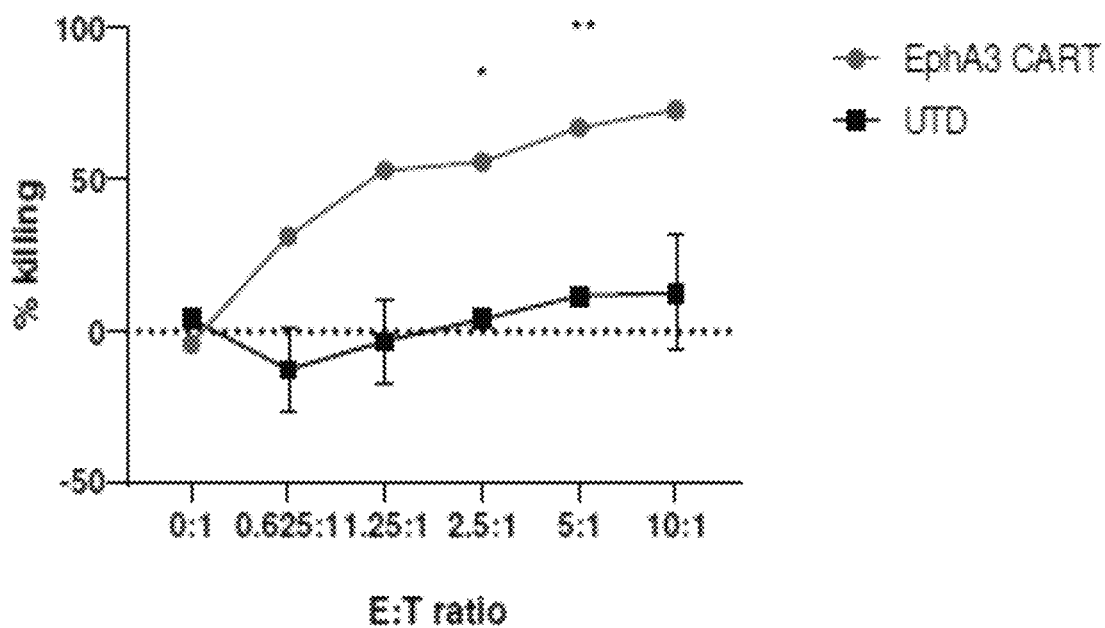
Figure 26B:
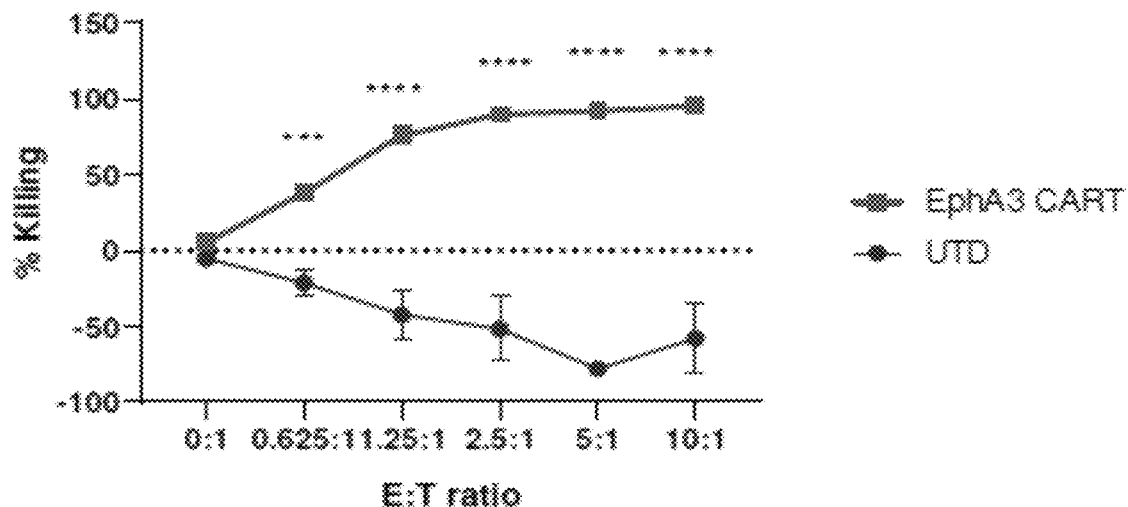
Figure 26C:
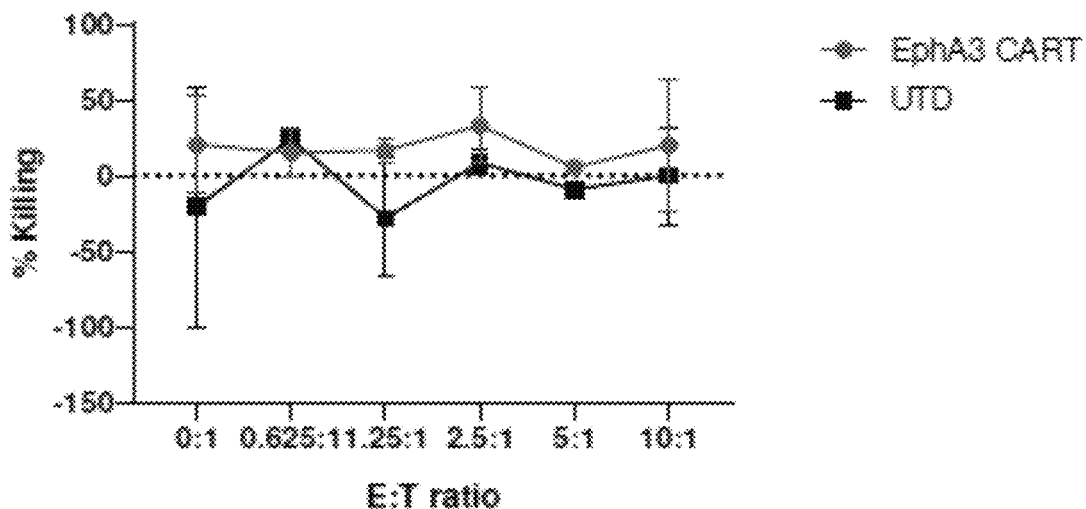

FIGS. 26A-26C show EphA3 CAR bioluminescence killing assay at 24 hour incubation versus GBM 76, GBM 6 and GBM 39.

Figure 27A:
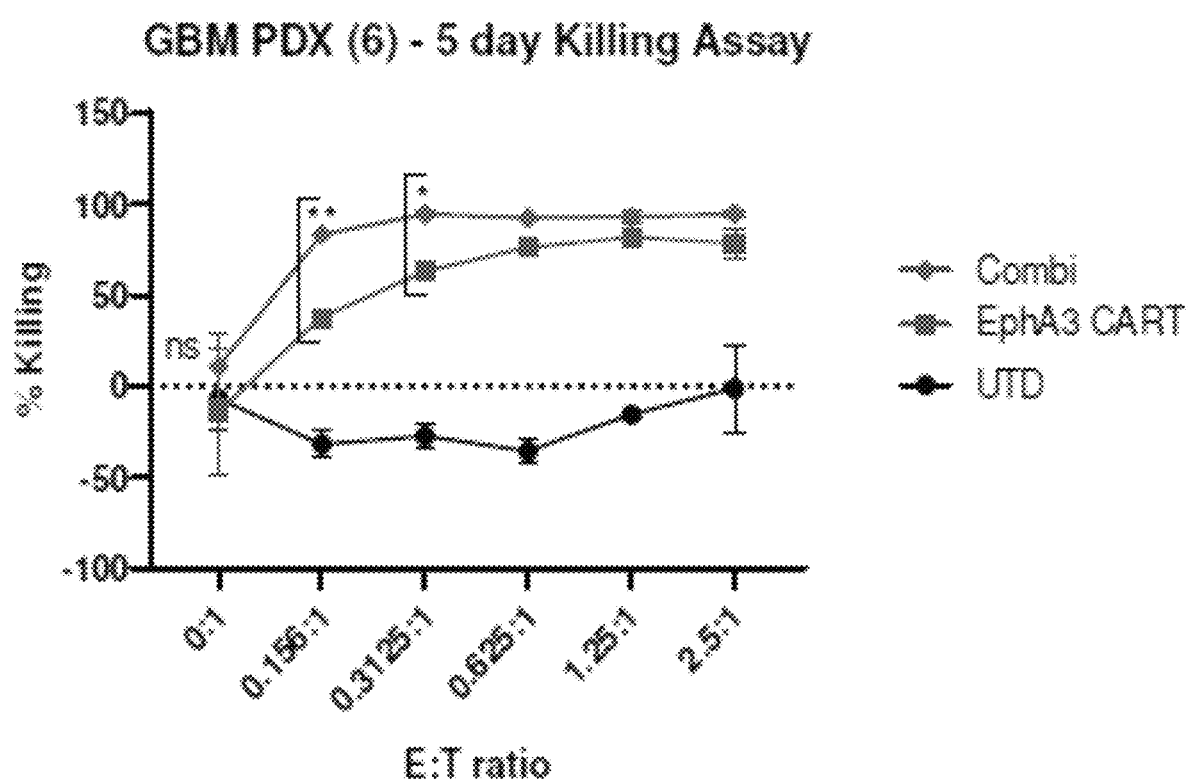
Figure 27B:
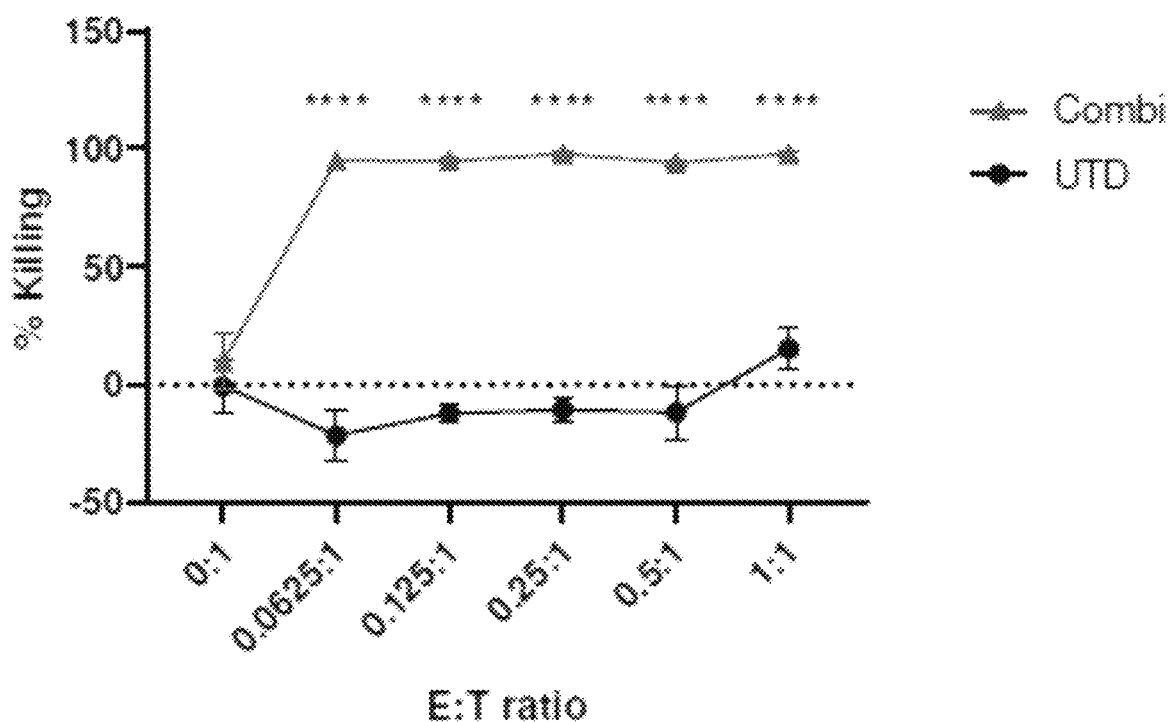

FIGS. 27A-27B show dual EphA3/EGFRvIII targeting CART cells exhibit potent antitumor killing against patient derived GBM.

Figure 28:
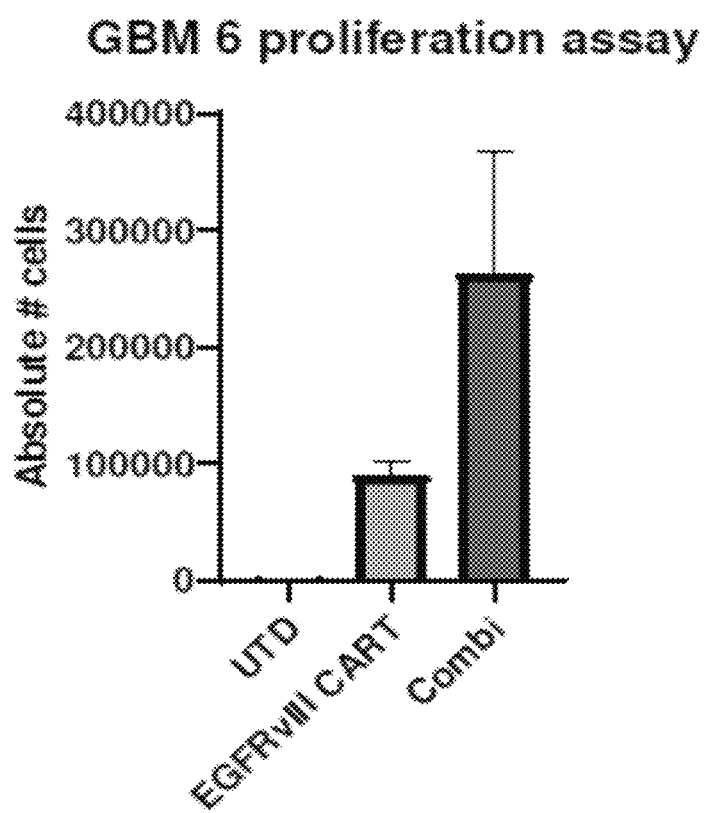

FIG. 28 shows combinatorial EGFRvIII and EphA3 CARs demonstrate increased proliferation when exposed to target antigen.

DETAILED DESCRIPTION OF THE INVENTION

The present invention may be understood more readily by reference to the following detailed description which forms a part of this disclosure. It is to be understood that this invention is not limited to the specific methods, products, conditions or parameters described and/or shown herein, and that the terminology used herein is for the purpose of describing particular embodiments by way of example only and is not intended to be limiting of the claimed invention.

GBM is the most aggressive adult brain cancer. It is characterized by highly infiltrative and heterogeneous cells. Despite surgical removal of a GBM tumor, most patients with GBM develop recurrent tumors near the original tumor site or at distant locations in the brain.

Studies have implicated overexpression of the receptor tyrosine kinase Eph receptor A3 (EphA3) in glioblastoma (GBM). EphA3 also has been shown to be elevated in various hematological cancers and solid tumors. It has been reported that EphA3 has oncogenic functions in GBM. In particular, EphA3 has been found to be predominantly expressed on glioma stem cells (GSCs), while it is expressed in low levels in normal brain tissue.

The present invention is directed to the treatment of GBM and other solid tumors overexpressing EphA3 by administration of a chimeric antigen receptor that binds to human EphA3 on tumor neovasculature and tumor stromal cells.

Unless otherwise defined herein, scientific, and technical terms used in connection with this application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In this disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality," as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

In one aspect, the present invention provides a chimeric antigen receptor (CAR) that binds to human Eph receptor A3 (EphA3), the CAR comprising an extracellular anti-human EphA3 binding domain comprising a single chain variable fragment (scFv) of anti-human EphA3 monoclonal antibody ifabotuzumab, wherein the human EphA3 scFv comprises a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2. In an embodiment, the $V_H$ and the $V_L$ are attached by a linker peptide. In another embodiment, the linker peptide comprises an amino acid sequence of SEQ ID NO: 4. In an embodiment, the extracellular anti-human EphA3 binding domain is connected to a transmembrane domain by a hinge region. In some embodiments, the hinge region comprises a CD8 hinge region or a CD28 hinge region. In another embodiment, the CD8 hinge region comprises an amino acid sequence of SEQ ID NO: 5. In some embodiments, the CD28 hinge region comprises an amino acid sequence of SEQ ID NO: 6. In an embodiment, when the hinge region comprises a CD8 hinge region the transmembrane domain comprises a CD8 transmembrane domain. In another embodiment, when the hinge region comprises a CD28 hinge region the transmembrane domain comprises a CD28 transmembrane domain. In an embodiment, the CD8 transmembrane domain comprises an amino acid sequence of SEQ ID NO: 7. In another embodiment, the CD28 transmembrane domain comprises an amino acid sequence of SEQ ID NO: 8. In an embodiment of the herein provided CAR, the CAR further comprises a leader sequence. In some embodiments, the leader sequence comprises an amino acid sequence of SEQ ID NO: 3. In an embodiment, the CAR further comprises an intracellular signaling domain. In another embodiment, the intracellular signaling domain comprises a costimulatory domain and an activation domain. In some embodiments of the provided CAR, the costimulatory domain comprises a 4-1BB costimulatory domain or a CD28 costimulatory domain. In another embodiment, the activation domain is a CD3 zeta (CD3z or CD3ζ) activation domain. In an embodiment, the 4-1BB costimulatory domain costimulatory domain comprises an amino acid sequence of SEQ ID NO: 9. In a particular embodiment, the CD28 costimulatory domain comprises an amino acid sequence of SEQ ID NO: 10. In another embodiment, the CD3z activation domain comprises an amino acid sequence of SEQ ID NO: 11.

In another aspect, the present invention provides a CAR construct that binds to human EphA3 comprising: (a) a single chain variable fragment (scFv) of monoclonal antibody ifabotuzumab that binds to human EphA3, the scFv comprising a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2; wherein the $V_H$ and the $V_L$ are attached by a linker peptide comprising an amino acid sequence of SEQ ID NO: 4; (b) a hinge region comprising a CD8 hinge region comprises an amino acid sequence of SEQ ID NO: 5 or a CD28 hinge region comprises an amino acid sequence of SEQ ID NO: 6. (c) a transmembrane domain, and (d) an intracellular signaling domain comprising a costimulatory domain and an activation domain.

In an embodiment of the CAR construct that binds to human EphA3, the hinge region comprises the CD8 hinge region, the CD8 hinge region comprises an amino acid sequence of SEQ ID NO: 5. In another embodiment, wherein when the hinge region comprises a CD28 hinge region, the CD28 hinge region comprises an amino acid sequence of SEQ ID NO: 6. In some embodiments, the CAR construct further comprises a CD8 transmembrane domain comprising an amino acid sequence of SEQ ID NO: 7. In an embodiment, the CAR construct further comprises a CD28 transmembrane domain comprising an amino acid sequence of SEQ ID NO: 8. In a particular embodiment, the costimulatory domain comprises a 4-1BB costimulatory domain or a CD28 costimulatory domain. In another embodiment, the activation domain is a CD3z activation domain. In some embodiments, the 4-1BB costimulatory domain costimulatory domain comprises an amino acid sequence of SEQ ID NO: 9. In an embodiment, the CD28 costimulatory domain comprises an amino acid sequence of SEQ ID NO: 10. In some embodiments, the CD3% activation domain comprises an amino acid sequence of SEQ ID NO: 11. In a particular embodiment, the scFv of monoclonal antibody ifabotuzumab that binds to human EphA3, the hinge region, the transmembrane domain, and the intracellular signaling domain are fused in tandem.

In an embodiment, the human EphA3-targeting CAR expression cassette comprising the second generation CAR is cloned into a lentivirus backbone under control of a promoter, as described herein. In another embodiment of the human EphA3-targeting CAR expression cassette of claim 32, the promoter is human elongation factor-1 alpha (EF-1α). In an embodiment, the EF1 alpha promoter has a nucleic acid of (SEQ ID NO: 54):

```
GTGAGGCTCCGGTGCCCGTCAGTGGGCAGAGCGCACATCGCCCACAGTCC
CCGAGAAGTTGGGGGGAGGGGTCGGCAATTGAACCGGTGCCTAGAGAAGG
TGGCGCGGGGTAAACTGGGAAAGTGATGTCGTGTACTGGCTCCGCCTTTT
TCCCGAGGGTGGGGAGAACCGTATATAAGTGCAGTAGTCGCCGTGAACG
```

-continued
```
TTCTTTTTCGCAACGGGTTTGCCGCCAGAACACAGGTAAGTGCCGTGTGT
GGTTCCCGCGGGCCTGGCCTCTTTACGGGTTATGGCCCTTGCGTGCCTTG
AATTACTTCCACCTGGCTGCAGTACGTGATTCTTGATCCCGAGCTTCGGG
TTGGAAGTGGGTGGGAGAGTTCGAGGCCTTGCGCTTAAGGAGCCCCTTCG
CCTCGTGCTTGAGTTGAGGCCTGGCCTGGGCGCTGGGGCCGCCGCGTGCG
AATCTGGTGGCACCTTCGCGCCTGTCTCGCTGCTTTCGATAAGTCTCTAG
CCATTTAAAATTTTTGATGACCTGCTGCGACGCTTTTTTTCTGGCAAGAT
AGTCTTGTAAATGCGGGCCAAGATCTGCACACTGGTATTTCGGTTTTTGG
GGCCGCGGGCGGCGACGGGGCCCGTGCGTCCCAGCGCACATGTTCGGCGA
GGCGGGGCCTGCGAGCGCGGCCACCGAGAATCGGACGGGGGTAGTCTCAA
GCTGGCCGGCCTGCTCTGGTGCCTGGCCTCGCGCCGCCGTGTATCGCCCC
GCCCTGGGCGGCAAGGCTGGCCCGGTCGGCACCAGTTGCGTGAGCGGAAA
GATGGCCGCTTCCCGGCCCTGCTGCAGGGAGCTCAAAATGGAGGACGCGG
CGCTCGGGAGAGCGGGCGGGTGAGTCACCCACACAAAGGAAAAGGGCCTT
TCCGTCCTCAGCCGTCGCTTCATGTGACTCCACGGAGTACCGGGCGCCGT
CCAGGCACCTCGATTAGTTCTCGAGCTTTTGGAGTACGTCGTCTTTAGGT
TGGGGGGAGGGGTTTTATGCGATGGAGTTTCCCCACACTGAGTGGGTGGA
GACTGAAGTTAGGCCAGCTTGGCACTTGATGTAATTCTCCTTGGAATTTG
CCCTTTTTGAGTTTGGATCTTGGTTCATTCTCAAGCCTCAGACAGTGGTT
CAAAGTTTTTTCTTCCATTTCAGGTGTCGTGA.
```

In some embodiments of the human EphA3-targeting CAR expression cassette, the lentivirus backbone is a third generation wherein the lentivirus backbone. In an embodiment, the human EphA3-targeting CAR T-cell comprising the herein provided EphA3-targeting CAR expression cassette, wherein the CAR-T cell expresses the CAR on a cell surface thereof, as described herein. In another embodiment, the EphA3-targeting CAR T-cell is an autologous EphA3-targeting CAR T-cell.

In an embodiment, provided herein is a pharmaceutical composition comprising the human EphA3-targeting CAR-T cell, as described herein, and a pharmaceutically acceptable carrier. In some embodiments of the pharmaceutical composition, the human EphA3-targeting CAR-T cell is autologous.

In an embodiment, provided herein is a method for producing a human EphA3-targeting CAR T-cell, the method comprising transducing a T-cell with the EphA3 CAR expression cassette, as described herein.

In a further embodiment, provided herein is a method for treating a solid tumor cancer, the method comprising administering to a subject in need thereof the pharmaceutical compositions described herein. In a particular embodiment, the solid tumor cancer is a brain cancer. In a specific embodiment, the brain cancer is glioblastoma multiforme (GBM). In an embodiment, the solid tumor cancer is a colon, kidney, bladder, breast, liver, pancreatic, prostate tumor, a melanoma, myeloma, or a lung cancer, e.g., small cell lung cancer (SCLC) or non-small cell lung cancer (NSCLC). In another embodiment, the solid tumor cancer expresses EphA3 on a surface of tumor cells, tumor-associated vasculature and/or tumor stroma. In an embodiment, the tumor stroma cells comprise myeloid derived suppressor cells. In an embodiment, the tumor cells comprise tumor stem cells. In particular embodiments, the tumor-associated vasculature comprises neo-vasculature.

In an embodiment, the method further comprises administering a human GM-CSF (hGM-CSF) antagonist selected from the group consisting of an anti-human GM-CSF antibody, an anti-hGM-CSF antibody fragment, a soluble hGM-CSF receptor alpha, an anti-hGM-CSF receptor (GM-CSFr) antibody and an anti-hGM-CSFr antibody fragment. In a specific embodiment, the anti-human GM-CSF antibody is hGM-CSF neutralizing antibody lenzilumab. In a specific embodiment the anti-human GM-CSF antibody is Namilumab, Otilimab, Gimsilumab, and TJM2 (TJ003234). In a further embodiment, the GM-CSF antagonist is anti-GM-CSF receptor antibody Mavrilimumab.

An anti-human GM-CSF antibody administered according to the invention may comprise any of the $V_H$ regions VH #1, VH #2, VH #3, VH #4, or VH #5 as shown in FIG. 1 of U.S. Pat. Nos. 8,168,183 and 9,017,674, each of which is incorporated herein by reference in its entirety. In a particular embodiment, the anti-human GM-CSF antibody comprises VH #5 and VLK #2, as shown in FIG. 1 of U.S. Pat. Nos. 8,168,183 and 9,017,674, each of which is incorporated herein by reference in its entirety.

In some embodiments, an anti-human GM-CSF antibody of the invention may comprise any of the $V_L$ regions VK #1, VK #2, VK #3, or VK #4 as shown in FIG. 1. In some embodiments, the anti-human GM-CSF antibody has a $V_H$ region VH #1, VH #2, VH #3, VH #4, or VH #5 as shown in FIG. 1 of U.S. Pat. Nos. 8,168,183 and 9,017,674, each of which is incorporated herein by reference in its entirety; and a $V_L$ region VK #1, VK #2, VK #3, or VK #4 as shown in FIG. 1, as described, e.g., in U.S. Pat. Nos. 8,168,183 and 9,017,674, each of which is incorporated herein by reference in its entirety.

In an embodiment, administration of lenzilumab reduces relapse rate or prevents occurrence of solid tumor relapse. In another embodiment, administration of lenzilumab prevents or reduces incidence of immunotherapy-related toxicity in the subject. In some embodiments, the immunotherapy-related toxicity is EphA3-targeting CAR-T cell related toxicity. In an embodiment, the EphA3-targeting CAR-T cell related toxicity is cytokine release syndrome, neurotoxicity and/or neuro-inflammation. In another embodiment, the method further comprises administering GM-CSF silenced EphA3-targeting CAR-T cells or gene knockout (GM-CSF$^{k/o}$) EphA3-targeting CAR-T cells, wherein administration of GM-CSF silenced EphA3-targeting CAR-T cells or GM-CSF$^{k/o}$ EphA3-targeting CAR-T cells prevents or reduces incidence of immunotherapy-related toxicity in the subject. In an embodiment, administration of the GM-CSF silenced EphA3-targeting CAR-T cells or GM-CSF$^{k/o}$ EphA3-targeting CAR-T cells reduces relapse rate or prevents occurrence of solid tumor relapse. In another embodiment, the method further comprises administering at least one immune checkpoint inhibitor selected from the group consisting of an anti-programmed cell death-1 (PD-1) antibody, an anti-programmed death-ligand 1 (PD-L1) antibody, and an anti-cytotoxic T-lymphocyte associated protein 4 (CTLA-4) antibody. In an embodiment, the method further comprises administering at least one immune checkpoint inhibitor selected from the group consisting of an anti-programmed cell death-1 (PD-1) antibody, an anti-programmed death-ligand 1 (PD-L1) antibody, and an anti-cytotoxic T-lymphocyte associated protein 4 (CTLA-4) antibody.

In a specific embodiment, the anti-programmed cell death-1 antibody is Pembrolizumab. In another embodiment the anti-programmed death-ligand antibody is avelumab. In another embodiment the anti-cytotoxic T-lymphocyte associated protein 4 (CTLA-4) antibody is Ipilimumab.

In another embodiment, the present invention provides a method for reducing solid tumor cancer relapse rate or preventing occurrence of solid tumor cancer relapse in a subject in need thereof, the method comprising administering to a subject a pharmaceutical composition, as described herein. In one embodiment, the solid tumor cancer is a brain cancer. In another embodiment, the brain cancer is glioblastoma multiforme (GBM). In an embodiment, the solid tumor cancer is a colon, kidney, bladder, breast, liver, pancreatic, prostate, melanoma, myeloma, lung, including non-small cell lung cancer (NSCLC) or a small cell lung cancer (SCLC). In another embodiment, the solid tumor cancer expresses EphA3 on a surface of tumor cells, tumor-associated vasculature and/or tumor stroma. In an embodiment, the tumor stroma cells comprise myeloid derived suppressor cells. In one embodiment, the tumor cells comprise tumor stem cells. In another embodiment, the tumor-associated vasculature comprises neo-vasculature. In still another embodiment, the method further comprises administering a human GM-CSF (hGM-CSF) antagonist selected from the group consisting of an anti-human GM-CSF antibody, an anti-hGM-CSF antibody fragment, a soluble hGM-CSF receptor alpha, an anti-hGM-CSF receptor (GM-CSFr) antibody and an anti-hGM-CSFr antibody fragment. In an embodiment, the anti-human GM-CSF antibody is hGM-CSF neutralizing antibody lenzilumab. In a specific embodiment the anti-human GM-CSF antibody is Namilumab, Otilimab, Gimsilumab, and TJM2 (TJ003234). In a further embodiment, the GM-CSF antagonist is anti-GM-CSF receptor antibody Mavrilimumab. In another embodiment, administration of lenzilumab reduces relapse rate or prevents occurrence of solid tumor relapse. In some embodiments, administration of lenzilumab prevents or reduces incidence of immunotherapy-related toxicity in the subject. In an embodiment, the immunotherapy-related toxicity is EphA3-targeting CAR-T cell related toxicity. In another embodiment, the EphA3-targeting CAR-T cell related toxicity is cytokine release syndrome, neurotoxicity and/or neuro-inflammation. In an embodiment, the method further comprises administering GM-CSF silenced EphA3-targeting CAR-T cells or gene knockout (GM-CSF$^{k/o}$) EphA3-targeting CAR-T cells, wherein administration of GM-CSF silenced EphA3-targeting CAR-T cells or GM-CSF$^{k/o}$ EphA3-targeting CAR-T cells prevents or reduces the incidence of immunotherapy-related toxicity in the subject. In an embodiment, the method further comprises administering at least one immune checkpoint inhibitor selected from the group consisting of an anti-programmed cell death-1 (PD-1) antibody, an anti-programmed death-ligand 1 (PD-L1) antibody, and an anti-cytotoxic T-lymphocyte associated protein 4 (CTLA-4) antibody. In a specific embodiment, the anti-programmed cell death-1 antibody is Pembrolizumab. In another embodiment the anti-programmed death-ligand antibody is avelumab. In another embodiment the anti-cytotoxic T-lymphocyte associated protein 4 (CTLA-4) antibody is Ipilimumab In one aspect, the present invention provides a dual targeting CAR-T cell that binds to human EphA3 and to human mutant epidermal growth factor receptor variant III (EGFRvIII), the CAR-T cell comprising:

a first CAR construct that binds to human Eph receptor A3 (EphA3), the CAR comprising an extracellular anti-human EphA3 binding domain comprising a human EphA3 single chain variable fragment (scFv) of anti-EphA3 monoclonal antibody ifabotuzumab, wherein the human EphA3 scFv comprises a heavy chain immunoglobulin variable region (V$_H$) comprising an amino acid sequence of SEQ ID NO: 1 and a light chain immunoglobulin variable region (V$_L$) comprising an amino acid sequence of SEQ ID NO: 2.
  wherein the scFv of monoclonal antibody ifabotuzumab that binds to human EphA3, is fused in tandem to a hinge region, a transmembrane domain; and an intracellular signaling domain comprising a costimulatory domain and an activation domain;
  and
a second CAR construct that binds to human mutant epidermal growth factor receptor variant III (EGFRvIII) comprising a humanized anti-EGFRvIII binding domain, wherein the humanized anti-EGFRvIII binding domain comprises:
  (a) a heavy chain immunoglobulin variable region comprising:
    (i) a CDR1 comprising amino acid sequence DYYIH (SEQ ID NO: 31);
    (ii) a CDR2 comprising amino acid sequence RIDPENDETKYGPIFQG (SEQ ID NO: 32); and
    (iii) a CDR3 comprising amino acid sequence RGGVY (SEQ ID NO: 33); and
  (b) a light chain immunoglobulin variable region comprising:
    (i) a CDR1 comprising amino acid sequence KSSQSLLDSDGKTYLN (SEQ ID NO: 34);
    (ii) a CDR2 comprising the sequence LVSKLDS (SEQ ID NO: 35); and
    (iii) a CDR3 comprising amino acid sequence WQGTHFPGT (SEQ ID NO: 36).
In an embodiment of the dual targeting CAR-T cell, the humanized anti-EGFRvIII binding domain is a humanized single chain variable fragment (scFv) of monoclonal antibody clone 3C10, the humanized scFV having amino acid sequence:

```
                                      (SEQ ID NO: 37)
EIQLVQSGAEVKKPGESLRISCKGSGFNIEDYYIHWVRQMPGKGLEWMG

RIDPENDETKYGPIFQGHVTISADTSINTVYLQWSSLKASDTAMYYCAF

RGGVYWGQGTTVTVSSGGGGSGGGGSGGGGSGGGGSDVVMTQSPDSLAV

SLGERATINCKSSQSLLDSDGKTYLNWLQQKPGQPPKRLISLVSKLDSG

VPDRFSGSGSGTDFTLTISSLQAEDVAVYYCWWQGTHFPGTFGGGTKVE

IK
```

In another embodiment, the second CAR further comprises:
  (c) a transmembrane domain comprising amino acid sequence

```
                           (SEQ ID NO: 38)
IYIWAPLAGTCGVLLLSLVITLYC;
```

(d) a hinge region comprising amino acid sequence

```
                                      (SEQ ID NO: 39)
TTTPAPRPPTPAPTIASQPLSLRPEACRPAAGGAVHTRGLDFACD;
```

(e) an intracellular signaling domain comprising a costimulatory domain and a primary signaling domain, wherein the costimulatory domain comprises a 4-1BB costimulatory domain comprising amino acid sequence of SEQ ID NO: 9.

In another embodiment of the dual targeting CAR-T cell, the primary signaling domain comprises a CD3 zeta domain having amino acid sequence:

```
                                      (SEQ ID NO: 40)
RVKFSRSADAPAYKQGQNQLYNELNLGRREEYDVLDKRRGRDPEMGGKP
RRKNPQE.
```

In another embodiment, the primary signaling domain comprises amino acid sequence NCBI Reference Sequence NM_000734.3:

```
                                      (SEQ ID NO: 41)
RVKFSRSADAPAYKQGQNQLYNELNLGRREEYDVLDKRRGRDPEMGGKP

RRKNPQELYNELQKDKMAEAYSEIGMKGERRRGKGHDGLYQGLSTATKD

TYDALHMQALPPR.
```

In another embodiment, a pharmaceutical composition comprises the dual targeting CAR-T cell that binds to human EphA3 and to human mutant EGFRvIII provided herein and a pharmaceutically acceptable carrier.

In another aspect, the present invention provides a method for producing a dual targeting CAR-T cell that binds to human EphA3 and human EGFRVIII, the method comprising: (a) transducing a T-cell with an EphA3-targeting CAR expression cassette comprising a CAR that binds to human EphA3 and is encoded by an isolated nucleic acid sequence of SEQ ID NO: 16, SEQ ID NO: 17, SEQ ID NO: 18 or SEQ ID NO: 19 to produce a human EphA3-targeting CAR T-cell; and (b) transducing the human EphA3-targeting CAR T-cell produced in step (a) with an expression cassette comprising a human EGFRvIII-targeting CAR that binds to human EGFRvIII and the human EGFRvIII-targeting CAR is encoded by a nucleic acid sequence of SEQ ID NO: 42:

```
ATGGCCTTACCAGTTACCGCCTTATTATTGCCTTTAGCCTTATTGTTAC

ATGCCGCCCGTCCGGGATCCGAGATTCAGCTGCAGCAATCTGGGGCAGA

ACTTGTGAAGCCAGGGGCCTCAGTCAAGCTGTCCTGCACAGGTTCTGGC

TTCAACATTGAAGACTACTATATTCACTGGGTGAAGCAGAGGACTGAAC

AGGGCCTGGAATGGATTGGAAGGATTGATCCTGAGAATGATGAAACTAA

ATATGCCCAATATTCCAGGGCAGGGCCACTATAACAGCAGACACATCC

TCCAACACAGTCTACCTGCAACTCAGCAGCCTGACATCTGAGGACACTG

CCGTCTATTACTGTGCCTTTCGCGGTGGAGTCTACTGGGGGCCAGGAAC

CACTCTCACAGTCTCCTCAGGAGGTGGTGGTTCCGGTGGTGGTGGTTCC

GGAGGTGGTGGTTCACATATGGATGTTGTGATGACCCAGTCTCCACTCA

CTCTATCGGTTGCCATTGGACAATCAGCCTCCATCTCTTGCAAGTCAAG

TCAGAGCCTCTTAGATAGTGATGGAAAGACATATTTGAATTGGTTGTTA

CAGAGGCCAGGCCAGTCTCCAAAGCGCCTAATCTCTCTGGTGTCTAAAC

TGGACTCTGGAGTCCCTGACAGGTTCACTGGCAGTGGATCAGGGACAGA

TTTCACACTGAGAATCAGCAGAGTGGAGGCTGAGGATTTGGGAATTTAT

TATTGCTGGCAAGGTACACATTTTCCTGGGACGTTCGGTGGAGGGACCA

AGCTGGAGATAAAAGCTAGCACCACTACCCCTGCACCGCGACCACCAAC

ACCGGCGCCCACCATTGCGTCGCAGCCTCTGTCCCTGCGCCCAGAAGCA
```

```
TGCCGTCCAGCAGCAGGTGGTGCAGTTCATACTCGTGGTCTGGATTTCG

CCTGTGATATCTACATCTGGGCGCCCTTGGCCGGGACTTGTGGGGTCCT

TCTCCTGTCACTGGTTATCACCCTTTACTGCAAACGGGGCAGAAAGAAA

CTCCTGTATATATTCAAACAACCATTTATGAGACCAGTACAAACTACTC

AAGAGGAAGATGGCTGTAGCTGCCGATTTCCAGAAGAAGAAGAAGGAGG

ATGTGAACTGAGAGTGAAGTTCAGCAGGAGCGCAGACGCCCCCGCGTAC

AAGCAGGGCCAGAACCAGCTCTATAACGAGCTCAATCTAGGACGAAGAG

AGGAGTACGATGTTTTGGACAAGAGACGTGGCCGGGACCCTGAGATGGG

GGGAAAGCCGAGAAGGAAGAACCCTCAGGAAGGCCTGTACAATGAACTG

CAGAAAGATAAGATGGCGGAGGCCTACAGTGAGATTGGGATGAAAGGCG

AGCGCCGGAGGGGCAAGGGGCACGATGGCCTTTACCAGGGTCTCAGTAC

AGCCACCAAGGACACCTACGACGCCCTTCACATGCAGGCCCTGCCCCCT

CGCTAA
``` to produce a human EphA3-targeting- and a human EGFRvIII-targeting-CAR T-cell, wherein the human EphA3-targeting- and human EGFRvIII-targeting-CAR T-cell expresses the human EphA3-targeting CAR and the human EGPRvIII-targeting CAR on a cell surface thereof.

In an embodiment of the method, the encoded human EGFRvIII-targeting CAR comprises an amino acid sequence of SEQ ID NO: 43:

```
MALPVTALLLPLALLLHAARPGSEIQLQQSGAELVKPGASVKLSCTGSG

FNIEDYYIHWVKQRTEQGLEWIGRIDPENDETKYGPIFQGRATITADTS

SNTVYLQLSSLTSEDTAVYYCAFRGGVYWGPGTTLTVSSGGGGSGGGGS

GGGGSHMDVVMTQSPLTLSVAIGQSASISCKSSQSLLDSDGKTYLNWLL

QRPGQSPKRLISLVSKLDSGVPDRFTGSGSGTDFTLRISRVEAEDLGIY

YCWQGTHFPGTFGGGTKLEIKASTTTPAPRPPTPAPTIASQPLSLRPEA

CRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPP

R.
```

In another embodiment, provided is a method for treating a solid tumor cancer, the method comprising administering to a subject in need thereof the pharmaceutical composition, as described herein.

In a particular embodiment, the solid tumor cancer is a brain cancer. In a specific embodiment, the brain cancer is glioblastoma multiforme (GBM). In an embodiment, the solid tumor cancer is a colon, kidney, bladder, breast, liver, pancreatic, prostate tumor, a melanoma, myeloma or lung cancer, e.g., a non-small cell lung cancer (NSCLC) or a small cell lung cancer (SCLC). In another embodiment, the solid tumor cancer expresses EphA3 on a surface of tumor cells, tumor-associated vasculature and/or tumor stroma. In an embodiment, tumor stroma cells comprise myeloid derived suppressor cells. In an embodiment, the tumor cells comprise tumor stem cells. In particular embodiments, the tumor-associated vasculature comprises neo-vasculature.

In an embodiment, the method further comprises administering a human GM-CSF (hGM-CSF) antagonist selected from the group consisting of an anti-human GM-CSF antibody, an anti-hGM-CSF antibody fragment, a soluble hGM-CSF receptor alpha, an anti-hGM-CSF receptor (GM-CSFr) antibody and an anti-hGM-CSFr antibody fragment. In a specific embodiment, the anti-human GM-CSF antibody is hGM-CSF neutralizing antibody lenzilumab. In a specific embodiment the anti-human GM-CSF antibody is Namilumab, Otilimab, Gimsilumab, and TJM2 (TJ003234). In a further embodiment, the GM-CSF antagonist is anti-GM-CSF receptor antibody Mavrilimumab. In an embodiment, administration of lenzilumab reduces relapse rate or prevents occurrence of solid tumor relapse. In another embodiment, administration of lenzilumab prevents or reduces incidence of immunotherapy-related toxicity in the subject. In some embodiments, the immunotherapy-related toxicity is EphA3-targeting CAR-T cell related toxicity. In an embodiment, the EphA3-targeting CAR-T cell related toxicity is cytokine release syndrome, neurotoxicity and/or neuro-inflammation. In another embodiment, the method further comprises administering GM-CSF silenced EphA3-targeting CAR-T cells or gene knockout (GM-CSF$^{k/o}$) EphA3-targeting CAR-T cells, wherein administration of GM-CSF silenced EphA3-targeting CAR-T cells or GM-CSF$^{k/o}$ EphA3-targeting CAR-T cells prevents or reduces incidence of immunotherapy-related toxicity in the subject. In an embodiment, administration of the GM-CSF silenced EphA3-targeting CAR-T cells or GM-CSF$^{k/o}$ EphA3-targeting CAR-T cells reduces relapse rate or prevents occurrence of solid tumor relapse. In another embodiment, the method further comprises administering at least one immune checkpoint inhibitor selected from the group consisting of an anti-programmed cell death-1 (PD-1) antibody, an anti-programmed death-ligand 1 (PD-L1) antibody, and an anti-cytotoxic T-lymphocyte associated protein 4 (CTLA-4) antibody. In an embodiment, the method further comprises administering at least one immune checkpoint inhibitor selected from the group consisting of an anti-programmed cell death-1 (PD-1) antibody, an anti-programmed death-ligand 1 (PD-L1) antibody, and an anti-cytotoxic T-lymphocyte associated protein 4 (CTLA-4) antibody. In a specific embodiment the anti-programmed cell death-1 antibody is Pembrolizumab. In another embodiment the anti-programmed death-ligand antibody is avelumab. In another embodiment the anti-cytotoxic T-lymphocyte associated protein 4 (CTLA-4) antibody is Ipilimumab In another embodiment, the immunotherapy-related toxicity is EphA3-targeting CAR-T cell related toxicity and/or human EGFRvIII targeting CAR-T cell related toxicity. In an embodiment, the EphA3-targeting CAR-T cell related toxicity and/or human EGFRvIII targeting CAR-T cell related toxicity is cytokine release syndrome, neurotoxicity and/or neuro-inflammation.

In an embodiment, the CAR that binds to human Eph receptor A3 (EphA3) comprises amino acid sequence:

```
                                    (SEQ ID NO: 12)
MALPVTALLLPLALLLHAARPQVQLVQSGAEVKKPGASVKVSCKASGYT

FTGYWMNWVRQAPGQGLEWMGDIYPGSGNTNYDEKFQGRVTMTRDTSIS

TAYMELSRLRSDDTAVYYCARGGYYEDFDSWGQGTTVTVSSGGGGSGGG

GSGGGGSDIQMTQSPSFLSASVGDRVTITCRASQGIISYLAWYQQKPEK

APKRLIYAASSLQSGVPSRESGSGSGTEFTLTISSLQPEDFATYYCGQY
```

```
ANYPYTFGQGTKLEIKTTTPAPRPPTPAPTIASQPLSLRPEACRPAAGG

AVHTRGLDFACDIYIWAPLAGTCGVLLLSLVITLYCKRGRKKLLYIFKQ

PFMRPVQTTQEEDGCSCRFPEEEEGGCELRVKFSRSADAPAYKQGQNQL

YNELNLGRREEYDVLDKRRGRDPEMGGKPRRKNPQEGLYNELQKDKMAE

AYSEIGMKGERRRGKGHDGLYQGLSTATKDTYDALHMQALPPR.
```

In another embodiment, the CAR that binds to human Eph receptor A3 (EphA3) comprises amino acid sequence:

```
                                        (SEQ ID NO: 13)
MALPVTALLLPLALLLHAARPQVQLVQSGAEVKKPGASVKVSCKASGYT

FTGYWMNWVRQAPGQGLEWMGDIYPGSGNTNYDEKFQGRVTMTRDTSIS

TAYMELSRLRSDDTAVYYCARGGYYEDFDSWGQGTTVTVSSGGGGSGGG

GSGGGGSDIQMTQSPSFLSASVGDRVTITCRASQGIISYLAWYQQKPEK

APKRLIYAASSLQSGVPSRFSGSGSGTEFTLTISSLQPEDFATYYCGQY

ANYPYTFGQGTKLEIKLEPKSCDKTHTCPPCPDPKFWVLVVVGGVLACY

SLLVTVAFIIFWVRSKRSRLLHSDYMNMTPRRPGPTRKHYQPYAPPRDF

AAYRSRVKFSRSADAPAYKQGQNQLYNELNLGRREEYDVLDKRRGRDPE

MGGKPRRKNPQEGLYNELQKDKMAEAYSEIGMKGERRRGKGHDGLYQGL

STATKDTYDALHMQALPPR.
```

In an embodiment, the CAR that binds to human Eph receptor A3 (EphA3) comprises amino acid sequence:

```
                                        (SEQ ID NO: 14)
MALPVTALLLPLALLLHAARPDIQMTQSPSFLSASVGDRVTITCRASQG

IISYLAWYQQKPEKAPKRLIYAASSLQSGVPSRFSGSGSGTEFTLTISS

LQPEDFATYYCGQYANYPYTFGQGTKLEIKGGGGSGGGGSGGGGSQVQL

VQSGAEVKKPGASVKVSCKASGYTFTGYWMNWVRQAPGQGLEWMGDIYP

GSGNTNYDEKFQGRVTMTRDTSISTAYMELSRLRSDDTAVYYCARGGYY

EDFDSWGQGTTVTVSSLEPKSCDKTHTCPPCPDPKFWVLVVVGGVLACY

SLLVTVAFIIFWVRSKRSRLLHSDYMNMTPRRPGPTRKHYQPYAPPRDF

AAYRSRVKFSRSADAPAYKQGQNQLYNELNLGRREEYDVLDKRRGRDPE

MGGKPRRKNPQEGLYNELQKDKMAEAYSEIGMKGERRRGKGHDGLYQGL

STATKDTYDALHMQALPPR.
```

In an embodiment, the CAR that binds to human Eph receptor A3 (EphA3) comprises amino acid sequence:

```
                                        (SEQ ID NO: 15)
MALPVTALLLPLALLLHAARPDIQMTQSPSFLSASVGDRVTITCRASQG

IISYLAWYQQKPEKAPKRLIYAASSLQSGVPSRFSGSGSGTEFTLTISS

LQPEDFATYYCGQYANYPYTFGQGTKLEIKGGGGSGGGGSGGGGSQVQL

VQSGAEVKKPGASVKVSCKASGYTFTGYWMNWVRQAPGQGLEWMGDIYP

GSGNTNYDEKFQGRVTMTRDTSISTAYMELSRLRSDDTAVYYCARGGYY

EDFDSWGQGTTVTVSSTTTPAPRPPTPAPTIASQPLSLRPEACRPAAGG

AVHTRGLDFACDIYIWAPLAGTCGVLLLSLVITLYCKRGRKKLLYIFKQ

PFMRPVQTTQEEDGCSCRFPEEEEGGCELRVKFSRSADAPAYKQGQNQL

YNELNLGRREEYDVLDKRRGRDPEMGGKPRRKNPQEGLYNELQKDKMAE

AYSEIGMKGERRRGKGHDGLYQGLSTATKDTYDALHMQALPPR.
```

In another aspect, the present invention provides a chimeric antigen receptor (CAR) construct that binds to human Eph receptor A3 (EphA3), the CAR comprising an extracellular anti-human EphA3 binding domain comprising a human EphA3 single chain variable fragment (scFv) of anti-EphA3 monoclonal antibody, wherein the human EphA3 scFv comprises CDR3 of the $V_H$ region comprises GGYYEDFDS (SEQ ID NO: 44) and the CDR3 of the $V_L$ region comprises GQYANYPYT (SEQ ID NO:45).

In one aspect, the present invention provides a chimeric antigen receptor (CAR) construct that binds to human Eph receptor A3 (EphA3), the CAR construct comprising an extracellular anti-human EphA3 binding domain comprising:

a $V_H$ region comprising amino acid sequence

```
                                        (SEQ ID NO: 46)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS and
``` a $V_L$ region comprising amino acid sequence

```
                                        (SEQ ID NO: 47)
DIQMTQSPSFLSASVGDRVTITCRASQGIISYLAWYQQKPEKAPKRLIY

AASSLQSGVPSRFSGSGSGTEFTLTISSLQPEDFATYYCGQYANYPYTF

GQGTKLEIK.
```

In another aspect, the present invention provides a chimeric antigen receptor (CAR) construct that binds to human Eph receptor A3 (EphA3), the CAR construct comprising an extracellular anti-human EphA3 binding domain comprising:
- a $V_H$ region CDR1 having a sequence SYWIN (SEQ ID NO:48), a $V_H$ region CDR2 having a sequence DIYPGSGNTNYDEKFKR (SEQ ID NO:49), a $V_H$ region CDR3 having a sequence SGYYEDFDS (SEQ ID NO:50), and
- a $V_L$ region CDR1 having a sequence RASQEISGYLG (SEQ ID NO:51), a $V_L$ region CDR2 having a sequence AASTLDS (SEQ ID NO:52), and a $V_L$ region CDR3 having a sequence VQYANYPYT (SEQ ID NO:53).

In an embodiment of the herein provided human EphA3-targeting CAR T-cells comprising the above-described EphA3-targeting CAR constructs, the CAR-T cell expresses the CAR on a cell surface thereof. In another embodiment of the human EphA3-targeting CAR T-cell, the human EphA3-targeting CAR T-cell is an autologous EphA3-targeting CAR T-cell. In a further embodiment a pharmaceutical composition comprises the herein provided human EphA3-targeting CAR-T cells and a pharmaceutically acceptable carrier.

In an embodiment, provided herein is a method for treating a solid tumor cancer, the method comprising administering to a subject in need thereof any of the pharmaceutical compositions described herein.

Pharmaceutical Compositions

Described herein are pharmaceutical compositions comprising compounds or therapeutic agent of the invention and one or more pharmaceutically acceptable carriers and methods of administering them. "Pharmaceutically acceptable carriers" include any excipient which is nontoxic to the cell or mammal being exposed thereto at the dosages and concentrations employed. The pharmaceutical composition may include one or more therapeutic agents. In an embodiment, the pharmaceutical composition comprises a therapeutic agent, which is an EphA3 CART cell comprising an EphA-3 CART construct described herein in Examples 1, 2A, 2B and 3-5. In specific embodiments, the therapeutic agent comprises EphA3 CART cell comprising any one of EphA-3 CART constructs EphA3 CAR K082 (H2L-BBz), EphA3 CAR K083 (H2L-28z), EphA3 CAR K084 (L2H-28z), or EphA3 CAR K085 (L2H BBz) and combinations thereof. In an embodiment, the EphA3 CART cells comprise an EphA-3 CART construct comprising EphA3 scFv heavy chain comprising the nucleic acid sequence of SEQ ID NO: 21 and the nucleic acid sequence of SEQ ID NO: 23.

In a particular embodiment, the pharmaceutical composition comprises a therapeutic agent, wherein the therapeutic agent comprises EphA3 CART cells comprising an EphA-3 CART construct, the EphA-3 CART construct comprising EphA3 scFv heavy chain amino acid sequence

```
                                              (SEQ ID NO: 1)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS
``` and EphA3 scFv light chain amino acid sequence

```
                                              (SEQ ID NO: 2)
DIQMTQSPSFLSASVGDRVTITCRASQGIISYLAWYQQKPEKAPKRLIY

AASSLQSGVPSRFSGSGSGTEFTLTISSLQPEDFATYYCGQYANYPYTF

GQGTKLEIK.
```

In a particular embodiment, the pharmaceutical composition comprises a therapeutic agent, which is an EphA-3 CART construct comprising the nucleic acid sequence of SEQ ID NO: 55, wherein the nucleic acid sequence comprises a CD8 leader, a single chain variable fragment (scFv) of anti-human EphA3 monoclonal antibody ifabotuzumab (Ifab scFv) and a CD8 hinge.

In some embodiments, the pharmaceutical composition comprises as the therapeutic agent EphA3 CART cells comprising a chimeric antigen receptor (CAR) construct that binds to human Eph receptor A3 (EphA3) using a human EphA3 single chain variable fragment (scFv) of anti-EphA3 monoclonal antibody, wherein the human EphA3 scFv comprises CDR3 of the $V_H$ region comprises GGYYEDFDS (SEQ ID NO:44) and the CDR3 of the $V_L$ region comprises GQYANYPYT (SEQ ID NO:45).

In certain embodiments, the pharmaceutical composition comprises as the therapeutic agent EphA3 CART cells comprising a chimeric antigen receptor (CAR) construct that binds to human Eph receptor A3 (EphA3), wherein the CAR construct comprises an extracellular anti-human EphA3 binding domain comprising:

a $V_H$ region comprising amino acid sequence:

```
                                              (SEQ ID NO: 46)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS and
``` a $V_L$ region comprising amino acid sequence:

```
DIQMTQSPSFLSASVGDRVTITCRASQGIISYLAWYQQKPEKAPKRLIY

AASSLQSGVPSRFSGSGSGTEFTLTISSLQPEDFATYYCGQYANYPYTF

GQ
```

GTKLEIK (SEQ ID NO:47). In an embodiment, the pharmaceutical composition comprises as the therapeutic agent EphA3 CART cells, the EphA3 CART cells comprising a chimeric antigen receptor (CAR) construct that binds to human Eph receptor A3 (EphA3), an extracellular anti-human EphA3 binding domain comprising a $V_H$ region CDR1 having a sequence SYWIN (SEQ ID NO:48), a $V_H$ region CDR2 having a sequence DIYPGSGNTNYDEKFKR (SEQ ID NO:49), a $V_H$ region CDR3 having a sequence SGYYEDFDS (SEQ ID NO:50), and a $V_L$ region CDR1 having a sequence RASQEISGYLG (SEQ ID NO:51), a $V_L$ region CDR2 having a sequence AASTLDS (SEQ ID NO:52), and a $V_L$ region CDR3 having a sequence VQYANYPYT (SEQ ID NO:53).

In an embodiment, the therapeutic agent comprises an EGFRViii CART (3C10-41BBz) comprising the nucleic acid sequence of SEQ ID NO: 42.

Thus, as used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In an embodiment, pharmaceutical compositions containing the therapeutic agent or agents described herein, can be, in one embodiment, administered to a subject by any method known to a person skilled in the art, such as, without limitation, orally, parenterally, transnasally, transmucosally, subcutaneously, transdermally, intramuscularly, intravenously, intraarterially, intra-dermally, intra-peritoneally, intra-ventricularly, intra-cranially, or intra-vaginally.

Carriers may be any of those conventionally used, as described above, and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. In one embodiment, water, preferably bacteriostatic water, is the carrier when the pharmaceutical composition is administered intravenously or intratumorally. Saline solutions and aqueous dextrose and glycerol solutions can also be employed as liquid carriers, particularly for injectable solutions.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include, without limitation, physiological saline, bacteriostatic water, Cremophor EL™ (BASF, Parsippany, N.J.) or phosphate buffered saline (PBS). The composition should be sterile and should be fluid to the extent that easy syringeability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as appropriate, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The compositions and formulations as described herein may be administered alone or with other biologically active agents. Administration can be systemic or local, e.g. through portal vein delivery to the liver. In addition, it may be advantageous to administer the composition into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant.

Moreover, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable" also includes those carriers approved by a regulatory agency of the Federal or a state government or listed in the U.S. Pharmacopeia or other generally recognized pharmacopeia for use in animals and, more particularly, in humans.

Effective Doses

Effective doses of the pharmaceutical compositions of the present invention, for treatment of conditions or diseases vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy. The pharmaceutical compositions of the invention thus may include a "therapeutically effective amount." A "therapeutically effective amount" refers to an amount effective, at dosages and for periods of time necessary, to achieve the desired therapeutic result. A therapeutically effective amount of a molecule or therapeutic agent may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

Furthermore, a skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of a compound of the invention that will be effective in the treatment of a particular disorder or condition, including retinal inflammation and neuron death secondary to ocular hypertension, also will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. In one embodiment, the dosage of the EphA3 CART cells comprising an EphA-3 CART construct as described herein—or combinations thereof, will be within the range of about 0.01 to—about 1000 mg/kg of body weight. In another embodiment, the dosage will be within the range of about 0.1 mg/kg to about 100 mg/kg. In another embodiment, the dosage will be within the range of about 1 mg/kg to about 10 mg/kg. In an embodiment, the dosage is about 10 mg/kg. In another embodiment, the dosage is 10 mg/kg.

The compound or composition or therapeutic agent of the invention, including the EphA3 CART cells comprising an EphA-3 CART construct as described herein- or combinations thereof, may be administered only once, or it may be administered multiple times. For multiple dosages, the composition may be, for example, administered three times a day, twice a day, once a day, once every two days, twice a week, weekly, once every two weeks, or monthly.

In an embodiment, the dosage is administered once. In an embodiment, the CAR-T cells according to the invention are administered once after lymphodepleting chemotherapy with Cyclophosphamide (CY) and Fludarabine (FLU). In an embodiment, the dosage is between $1 \times 10^4$ cell/kg to $2 \times 10^6$ cells/kg and is once. Moreover, effective doses may be extrapolated from dose-response curves derived from in vitro or animal model test bioassays or systems.

In an embodiment, the pharmaceutical composition comprising the human EphA3-targeting CAR-T cell is administered in combination with two or more pharmaceutical compositions, wherein each pharmaceutical composition comprises an antigen targeting CAR T cell, the antigen targeting CAR T cell comprising an antigen targeting CAR, wherein the antigen targeted by the CAR is selected from the group consisting of CAIX, CD133, CEA, c-MET, EGFR, EGFRVIII, EpCam, EphA2, ErB2/Her2, FAP, folate receptor alpha (FR-a), GD2, GPC3, IL-13Ra2, L1-CAM, Mesothelin, MUCI, PD-L1, PSCA, PSMA, ROR1, VEGFR-2, and HER2, or wherein each pharmaceutical composition comprises a liquid cancer CART selected from the group consisting of CART19, CART22, CART123, CART33, CART-CLL1, CART BCMA, CART38, CART138, and CS1-CART.

In an embodiment, the pharmaceutical composition comprising the human EphA3-targeting CAR-T cell is administered in combination with two or more pharmaceutical compositions, wherein each pharmaceutical composition comprises an antigen targeting CAR T cell, the antigen targeting CAR T cell comprising an antigen targeting CAR, wherein the antigen targeted is selected from the group consisting of CAIX, CD133, CEA, c-MET, EGFR, EGFRvIII, EpCam, EphA2, ErB2/Her2, FAP, folate receptor alpha (FR-a), GD2, GPC3, IL-13Ra2, L1-CAM, Mesothelin, MUCI, PD-L1, PSCA, PSMA, ROR1, VEGFR-2, and HER2, or wherein each pharmaceutical composition comprises a liquid cancer CART selected from the group consisting of CART19, CART22, CART123, CART33, CART-CLL1, CART BCMA, CART38, CART138, and CS1-CART.

In still another embodiment, the pharmaceutical composition comprising the human EphA3-targeting CAR-T cell is administered in combination with two or more pharmaceutical compositions, wherein each pharmaceutical composition comprises an antigen targeting CAR T cell, the antigen targeting CAR T cell comprising an antigen targeting CAR, wherein the antigen targeted is selected from the group consisting of CAIX, CD133, CEA, c-MET, EGFR, EGFRvIII, EpCam, EphA2, ErB2/Her2, FAP, folate receptor alpha (FR-a), GD2, GPC3, IL-13Ra2, L1-CAM, Mesothelin, MUCI, PD-L1, PSCA, PSMA, ROR1, VEGFR-2, and HER2, or wherein each pharmaceutical composition comprises a liquid cancer CART selected from the group consisting of CART19, CART22, CART123, CART33, CART-CLL1, CART BCMA, CART38, CART138, and CS1-CART. In various embodiments of the herein provided methods, the pharmaceutical composition comprising the human EphA3-targeting CAR-T cell is administered together or sequentially with the two or more pharmaceutical compositions. In an embodiment, administration of the pharmaceutical composition comprising the human EphA3-targeting CAR-T cell and the two or more pharmaceutical compositions improves objective response rates of the subject. In another embodiment, administration of the pharmaceutical composition comprising the human EphA3-targeting CAR-T cell and the two or more pharmaceutical compositions improves progression free survival of the subject. In yet another embodiment, administration of the pharmaceutical composition comprising the human EphA3-targeting CAR-T cell and the two or more pharmaceutical compositions improves overall survival of the subject. In an embodiment of the dual targeting CAR-T cell that binds to human EphA3 and to human mutant EGFRvIII as described herein, the dual targeting CAR-T cell is an autologous EphA3-targeting CAR T-cell. In an embodiment the herein provided pharmaceutical compositions comprise the dual targeting CAR-T cells that binds to human EphA3 and to human mutant EGFRVIII, as provided and described herein and a pharmaceutically acceptable carrier. In another embodiment of the herein provided and described methods for treating a solid tumor cancer, the method comprises administering to a subject in need thereof any one of the pharmaceutical compositions provided herein.

All patents and literature references cited in the present specification are hereby incorporated by reference in their entirety.

The following examples are presented in order to illustrate certain embodiments of the invention more fully. The examples should in no way be construed, however, as limiting the broad scope of the invention.

EXAMPLES

Example 1

Construction of CARs Binding to EphA3 and to Binding to EGFRViii

We constructed four chimeric antigen receptors (CARs) targeting EphA3 using the following nucleic acid sequences of a leader sequence, EphA3 scFv heavy chain, a linker sequence, EphA3 scFv light chain, hinge regions, transmembrane (TM) domains, intracellular signaling domains comprising a 4-1BB costimulatory domain or a CD28 costimulatory domain and aCD3 zeta activation domain. We constructed a CAR targeting EGFR Viii as described in U.S. Pat. No. 9,394,368, which is incorporated herein in its entirety. The following nucleic acid sequence (SEQ ID NO: 42) was used, which encoded the EGFR Viii of SEQ ID NO: 43.

CD8 Leader:

(SEQ ID NO: 20)
ATGGCCTTACCAGTGACCGCCTTGCTCCTGCCGCTGGCCTTGCTGCTCC
ACGCCGCCAGGCCG

EphA3 scFv Heavy Chain:

(SEQ ID NO: 21)
CAGGTGCAGCTGGTGCAGTCTGGGGCTGAGGTGAAGAAGCCTGGGGCCT

CAGTGAAGGTTTCCTGCAAGGCTTCTGGATACACCTTCACAGGCTACTG

GATGAATTGGGTGCGCCAGGCCCCCGGGCAAGGCCTGGAGTGGATGGGG

GACATCTACCCGGGCAGTGGTAACACAAACTACGATGAGAAGTTCCAGG

GTAGAGTCACGATGACCAGGGACACGTCCATCAGCACAGCCTACATGGA

GCTGAGCAGGCTGAGATCTGACGACACAGCCGTGTACTACTGCGCAAGA

GGTGGATATTATGAAGATTTTGATAGCTGGGGCCAAGGTACCACTGTGA

CCGTGAGCTCC

Linker (SEQ ID NO: 22)
GGTGGAGGTGGTTCGGGAGGTGGAGGTAGCGGAGGTGGTGGATCT

EphA3 scFv Light Chain (SEQ ID NO: 23)
GACATCCAGATGACCCAGTCTCCATCCTTCCTGTCTGCATCTGTAGGAG

ACAGAGTCACCATCACTTGCCGGGCCAGTCAGGGCATTATCAGTTATTT

AGCCTGGTATCAGCAAAAACCAGAGAAAGCCCCTAAGCGCCTGATCTAT

GCTGCATCCAGTTTGCAAAGTGGGGTCCCATCAAGGTTCAGCGGCAGTG

GATCTGGGACAGAATTCACTCTCACAATCAGCAGCCTGCAGCCTGAAGA

TTTTGCAACTTACTACTGCGGGCAGTATGCCAATTATCCGTACACCTTT

GGCCAAGGTACGAAACTGGAAATTAAA

CD8 Hinge

SEQ ID NO: 24)
ACCACTACCCCTGCACCGCGACCACCAACACCGGCGCCCACCATTGCGT

CGCAGCCTCTGTCCCTGCGCCCAGAAGCATGCCGTCCAGCAGCAGGTGG

TGCAGTTCATACTCGTGGTCTGGATTTCGCCTGTGAT

CD8 TM

SEQ ID NO: 25)
ATCTACATCTGGGCGCCCTTGGCCGGGACTTGTGGGGTCCTTCTCCTGT
CACTGGTTATCACCCTTTACTGC

41BB (SEQ ID NO: 26)
AAACGGGGCAGAAAGAAACTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG

CD28 hinge

SEQ ID NO: 27)
CTCGAGCCCAAATCTTGTGACAAAACTCACACATGCCCACCGTGCCCGG

ATCCCAAA

CD28 TM (SEQ ID NO: 28)
TTTTGGGTGCTGGTGGTGGTTGGTGGAGTCCTGGCTTGCTATAGCTTGC
TAGTAACAGTGGCCTTTATTATTTTCTGGGTG

CD28

(SEQ ID NO: 29)
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC

CD3z (SEQ ID NO: 30)
AGAGTGAAGTTCAGCAGGAGCGCAGACGCCCCCGCGTACAAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCTTCACATGCAGGCCCTGCCCCCTCGC

The above-provided isolated nucleic acid sequences encoded the following amino acid sequences for the herein described CARs:

CD8 Leader Amino Acid Sequence (SEQ ID NO: 3)
MALPVTALLLPLALLLHAARP

EphA3 scFv Heavy Chain Amino Acid Sequence (SEQ ID NO: 1)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS

Linker Amino Acid Sequence (SEQ ID NO: 4)
GGGGSGGGGSGGGGS

EphA3 scFv Light Chain Amino Acid Sequence (SEQ ID NO: 2)
DIQMTQSPSFLSASVGDRVTITCRASQGIISYLAWYQQKPEKAPKRLIY
AASSLQSGVPSRFSGSGSGTEFTLTISSLQPEDFATYYCGQYANYPYTF
GQGTKLEIK CD8 Hinge Amino Acid Sequence (SEQ ID NO: 5)
TTTPAPRPPTPAPTIASQPLSLRPEACRPAAGGAVHTRGLDFACD CD8 TM Amino Acid Sequence (SEQ ID NO: 7)
IYIWAPLAGTCGVLLLSLVITLYC 41BB Amino Acid Sequence (SEQ ID NO: 9)
KRGRKKLLYIFKQPFMRPVQTTQEEDGCSCRFPEEEEGGCEL CD28 Hinge Amino Acid Sequence (SEQ ID NO: 6)
LEPKSCDKTHTCPPCPDPK CD28 TM Amino Acid Sequence (SEQ ID NO: 8)
FWVLVVVGGVLACYSLLVTVAFIIFWV CD28 Amino Acid Sequence (SEQ ID NO: 10)
RSKRSRLLHSDYMNMTPRRPGPTRKHYQPYAPPRDFAAYRS CD3z Amino Acid Sequence (SEQ ID NO: 11)
RVKFSRSADAPAYKQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR The following isolated nucleic acid sequence encoded the herein described EphA3-targeting CARs:
EphA3 CAR K082 (H2L-BBz)

(SEQ ID NO: 16)
ATGGCCTTACCAGTGACCGCCTTGCTCCTGCCGCTGGCCTTGCTGCTCC
ACGCCGCCAGGCCGCAGGTGCAGCTGGTGCAGTCTGGGGCTGAGGTGAA
GAAGCCTGGGGCCTCAGTGAAGGTTTCCTGCAAGGCTTCTGGATACACC
TTCACAGGCTACTGGATGAATTGGGTGCGCCAGGCCCCCGGGCAAGGCC
TGGAGTGGATGGGGGACATCTACCCGGGCAGTGGTAACACAAACTACGA
TGAGAAGTTCCAGGGTAGAGTCACGATGACCAGGGACACGTCCATCAGC
ACAGCCTACATGGAGCTGAGCAGGCTGAGATCTGACGACACAGCCGTGT
ACTACTGCGCAAGAGGTGGATATTATGAAGATTTTGATAGCTGGGGCCA
AGGTACCACTGTGACCGTGAGCTCCGGTGGAGGTGGTTCGGAGGTGGA
GGTAGCGGAGGTGGTGGATCTGACATCCAGATGACCCAGTCTCCATCCT
TCCTGTCTGCATCTGTAGGAGACAGAGTCACCATCACTTGCCGGGCCAG
TCAGGGCATTATCAGTTATTTAGCCTGGTATCAGCAAAAACCAGAGAAA
GCCCCTAAGCGCCTGATCTATGCTGCATCCAGTTTGCAAAGTGGGGTCC
CATCAAGGTTCAGCGGCAGTGGATCTGGGACAGAATTCACTCTCACAAT
CAGCAGCCTGCAGCCTGAAGATTTTGCAACTTACTACTGCGGGCAGTAT
GCCAATTATCCGTACACCTTTGGCCAAGGTACGAAACTGGAAATTAAAA
CCACTACCCCTGCACCGCGACCACCAACACCGGCGCCCACCATTGCGTC
GCAGCCTCTGTCCCTGCGCCCAGAAGCATGCCGTCCAGCAGCAGGTGGT
GCAGTTCATACTCGTGGTCTGGATTTCGCCTGTGATATCTACATCTGGG
CGCCCTTGGCCGGGACTTGTGGGGTCCTTCTCCTGTCACTGGTTATCAC
CCTTTACTGCAAACGGGGCAGAAAGAAACTCCTGTATATATTCAAACAA
CCATTTATGAGACCAGTACAAACTACTCAAGAGGAAGATGGCTGTAGCT
GCCGATTTCCAGAAGAAGAAGAAGGAGGATGTGAACTGAGAGTGAAGTT
CAGCAGGAGCGCAGACGCCCCCGCGTACAAGCAGGGCCAGAACCAGCTC
TATAACAGCTCAATCTAGGACGAAGAGAGGAGTACGATGTTTTGGACA
AGAGACGTGGCCGGGACCCTGAGATGGGGGGAAAGCCGAGAAGGAAGAA
CCCTCAGGAAGGCCTGTACAATGAACTGCAGAAAGATAAGATGGCGGAG
GCCTACAGTGAGATTGGGATGAAAGGCGAGCGCCGGAGGGGCAAGGGGC
ACGATGGCCTTTACCAGGGTCTCAGTACAGCCACCAAGGACACCTACGA
CGCCCTTCACATGCAGGCCCTGCCCCCTCGC

EphA3 CAR K083 (H2L-28z)

(SEQ ID NO: 17)
ATGGCCTTACCAGTGACCGCCTTGCTCCTGCCGCTGGCCTTGCTGCTCC
ACGCCGCCAGGCCGCAGGTGCAGCTGGTGCAGTCTGGGGCTGAGGTGAA
GAAGCCTGGGGCCTCAGTGAAGGTTTCCTGCAAGGCTTCTGGATACACC
TTCACAGGCTACTGGATGAATTGGGTGCGCCAGGCCCCCGGGCAAGGCC
TGGAGTGGATGGGGGACATCTACCCGGGCAGTGGTAACACAAACTACGA
TGAGAAGTTCCAGGGTAGAGTCACGATGACCAGGGACACGTCCATCAGC
ACAGCCTACATGGAGCTGAGCAGGCTGAGATCTGACGACACAGCCGTGT
ACTACTGCGCAAGAGGTGGATATTATGAAGATTTTGATAGCTGGGGCCA
AGGTACCACTGTGACCGTGAGCTCCGGTGGAGGTGGTTCGGAGGTGGA
GGTAGCGGAGGTGGTGGATCTGACATCCAGATGACCCAGTCTCCATCCT
TCCTGTCTGCATCTGTAGGAGACAGAGTCACCATCACTTGCCGGGCCAG
TCAGGGCATTATCAGTTATTTAGCCTGGTATCAGCAAAAACCAGAGAAA
GCCCCTAAGCGCCTGATCTATGCTGCATCCAGTTTGCAAAGTGGGGTCC

-continued

```
CATCAAGGTTCAGCGGCAGTGGATCTGGGACAGAATTCACTCTCACAAT
CAGCAGCCTGCAGCCTGAAGATTTTGCAACTTACTACTGCGGGCAGTAT
GCCAATTATCCGTACACCTTTGGCCAAGGTACGAAACTGGAAATTAAAC
TCGAGCCCAAATCTTGTGACAAAACTCACACATGCCCACCGTGCCCGGA
TCCCAAATTTTGGGTGCTGGTGGTGGTTGGTGGAGTCCTGGCTTGCTAT
AGCTTGCTAGTAACAGTGGCCTTTATTATTTTCTGGGTGAGGAGTAAGA
GGAGCAGGCTCCTGCACAGTGACTACATGAACATGACTCCCCGCCGCCC
CGGGCCCACCCGCAAGCATTACCAGCCCTATGCCCCACCACGCGACTTC
```

```
GCAGCCTATCGCTCCAGAGTGAAGTTCAGCAGGAGCGCAGACGCCCCCG
CGTACAAGCAGGGCCAGAACCAGCTCTATAACGAGCTCAATCTAGGACG
AAGAGAGGAGTACGATGTTTTGGACAAGAGACGTGGCCGGGACCCTGAG
ATGGGGGGAAAGCCGAGAAGGAAGAACCCTCAGGAAGGCCTGTACAATG
AACTGCAGAAAGATAAGATGGCGGAGGCCTACAGTGAGATTGGGATGAA
AGGCGAGCGCCGGAGGGGCAAGGGGCACGATGGCCTTTACCAGGGTCTC
AGTACAGCCACCAAGGACACCTACGACGCCCTTCACATGCAGGCCCTGC
CCCCTCGC
```

EphA3 CAR K084 (L2H-28z)

(SEQ ID NO: 18)
```
ATGGCCTTACCAGTGACCGCCTTGCTCCTGCCGCTGGCCTTGCTGCTCCACGCCG
CCAGGCCGGACATCCAGATGACCCAGTCTCCATCCTTCCTGTCTGCATCTGTAGG
AGACAGAGTCACCATCACTTGCCGGGCCAGTCAGGGCATTATCAGTTATTTAGCC
TGGTATCAGCAAAAACCAGAGAAAGCCCCTAAGCGCCTGATCTATGCTGCATCC
AGTTTGCAAAGTGGGGTCCCATCAAGGTTCAGCGGCAGTGGATCTGGGACAGAA
TTCACTCTCACAATCAGCAGCCTGCAGCCTGAAGATTTTGCAACTTACTACTGCG
GGCAGTATGCCAATTATCCGTACACCTTTGGCCAAGGTACGAAACTGGAAATTA
AAGGTGGAGGTGGTTCGGGAGGTGGAGGTAGCGGAGGTGGTGGATCTCAGGTGC
AGCTGGTGCAGTCTGGGGCTGAGGTGAAGAAGCCTGGGGCCTCAGTGAAGGTTT
CCTGCAAGGCTTCTGGATACACCTTCACAGGCTACTGGATGAATTGGGTGCGCCA
GGCCCCCGGGCAAGGCCTGGAGTGGATGGGGGACATCTACCCGGGCAGTGGTAA
CACAAACTACGATGAGAAGTTCCAGGGTAGAGTCACGATGACCAGGGACACGTC
CATCAGCACAGCCTACATGGAGCTGAGCAGGCTGAGATCTGACGACACAGCCGT
GTACTACTGCGCAAGAGGTGGATATTATGAAGATTTTGATAGCTGGGGCCAAGG
TACCACTGTGACCGTGAGCTCCCTCGAGCCCAAATCTTGTGACAAAACTCACACA
TGCCCACCGTGCCCGGATCCCAAATTTTGGGTGCTGGTGGTGGTTGGTGGAGTCC
TGGCTTGCTATAGCTTGCTAGTAACAGTGGCCTTTATTATTTTCTGGGTGAGGAGT
AAGAGGAGCAGGCTCCTGCACAGTGACTACATGAACATGACTCCCCGCCGCCCC
GGGCCCACCCGCAAGCATTACCAGCCCTATGCCCCACCACGCGACTTCGCAGCCT
ATCGCTCCAGAGTGAAGTTCAGCAGGAGCGCAGACGCCCCCGCGTACAAGCAGG
GCCAGAACCAGCTCTATAACGAGCTCAATCTAGGACGAAGAGAGGAGTACGATG
TTTTGGACAAGAGACGTGGCCGGGACCCTGAGATGGGGGGAAAGCCGAGAAGG
AAGAACCCTCAGGAAGGCCTGTACAATGAACTGCAGAAAGATAAGATGGCGGA
GGCCTACAGTGAGATTGGGATGAAAGGCGAGCGCCGGAGGGGCAAGGGGCACG
ATGGCCTTTACCAGGGTCTCAGTACAGCCACCAAGGACACCTACGACGCCCTTCA
CATGCAGGCCCTGCCCCCTCGC
```

EphA3 CAR K085 (L2H BBz)

(SEQ ID NO: 19)
```
ATGGCCTTACCAGTGACCGCCTTGCTCCTGCCGCTGGCCTTGCTGCTCCACGCCG
CCAGGCCGGACATCCAGATGACCCAGTCTCCATCCTTCCTGTCTGCATCTGTAGG
AGACAGAGTCACCATCACTTGCCGGGCCAGTCAGGGCATTATCAGTTATTTAGCC
TGGTATCAGCAAAAACCAGAGAAAGCCCCTAAGCGCCTGATCTATGCTGCATCC
AGTTTGCAAAGTGGGGTCCCATCAAGGTTCAGCGGCAGTGGATCTGGGACAGAA
TTCACTCTCACAATCAGCAGCCTGCAGCCTGAAGATTTTGCAACTTACTACTGCG
GGCAGTATGCCAATTATCCGTACACCTTTGGCCAAGGTACGAAACTGGAAATTA
AAGGTGGAGGTGGTTCGGGAGGTGGAGGTAGCGGAGGTGGTGGATCTCAGGTGC
AGCTGGTGCAGTCTGGGGCTGAGGTGAAGAAGCCTGGGGCCTCAGTGAAGGTTT
CCTGCAAGGCTTCTGGATACACCTTCACAGGCTACTGGATGAATTGGGTGCGCCA
GGCCCCCGGGCAAGGCTGGAGTGGATGGGGGACATCTACCCGGGCAGTGGTAA
CACAAACTACGATGAGAAGTTCCAGGGTAGAGTCACGATGACCAGGGACACGTC
CATCAGCACAGCCTACATGGAGCTGAGCAGGCTGAGATCTGACGACACAGCCGT
GTACTACTGCGCAAGAGGTGGATATTATGAAGATTTTGATAGCTGGGGCCAAGG
TACCACTGTGACCGTGAGCTCCACCACTACCCCTGCACCGCGACCACCAACACCG
GCGCCCACCATTGCGTCGCAGCCTCTGTCCCTGCGCCCAGAAGCATGCCGTCCAG
CAGCAGGTGGTGCAGTTCATACTCGTGGTCTGGATTTCGCCTGTGATATCTACAT
CTGGGCGCCCTTGGCCGGGACTTGTGGGGTCCTTCTCCTGTCACTGGTTATCACC
CTTTACTGCAAACGGGGCAGAAAGAAACTCCTGTATATATTCAAACAACCATTTA
TGAGACCAGTACAAACTACTCAAGAGGAAGATGGCTGTAGCTGCCGATTTCCAG
AAGAAGAAGAAGGAGGATGTGAACTGAGAGTGAAGTTCAGCAGGAGCGCAGAC
GCCCCCGCGTACAAGCAGGGCCAGAACCAGCTCTATAACGAGCTCAATCTAGGA
CGAAGAGAGGAGTACGATGTTTTGGACAAGAGACGTGGCCGGGACCCTGAGATG
GGGGGAAAGCCGAGAAGGAAGAACCCTCAGGAAGGCCTGTACAATGAACTGCA
GAAAGATAAGATGGCGGAGGCCTACAGTGAGATTGGGATGAAAGGCGAGCGCC
GGAGGGGCAAGGGGCACGATGGCCTTTACCAGGGTCTCAGTACAGCCACCAAGG
ACACCTACGACGCCCTTCACATGCAGGCCCTGCCCCCTCGC
```

The above-described nucleic acid sequences encode chimeric CARs comprising the following amino acid sequences:

EphA3 CAR K082 (H2L-BBz) Amino Acid Sequence (SEQ ID NO: 12)
```
MALPVTALLLPLALLLHAARPQVQLVQSGAEVKKPGASVKVSCKASGYTFTGYWM

NWVRQAPGQGLEWMGDIYPGSGNTNYDEKFQGRVTMTRDTSISTAYMELSRLRSD

DTAVYYCARGGYYEDFDSWGQGTTVTVSSGGGGSGGGGSGGGGSDIQMTQSPSFLS

ASVGDRVTITCRASQGIISYLAWYQQKPEKAPKRLIYAASSLQSGVPSRFSGSGSGTE

FTLTISSLQPEDFATYYCGQYANYPYTFGQGTKLEIKTTTPAPRPPTPAPTIASQPLSLR

PEACRPAAGGAVHTRGLDFACDIYIWAPLAGTCGVLLLSLVITLYCKRGRKKLLYIF
```

```
KQPFMRPVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIGMKGER

RRGKGHDGLYQGLSTATKDTYDALHMQALPPR
```

EphA3 CAR K083 (H2L-28z) Amino Acid Sequence

```
                                                    (SEQ ID NO: 13)
MALPVTALLLPLALLLHAARPQVQLVQSGAEVKKPGASVKVSCKASGYTFTGYWM

NWVRQAPGQGLEWMGDIYPGSGNTNYDEKFQGRVTMTRDTSISTAYMELSRLRSD

DTAVYYCARGGYYEDFDSWGQGTTVTVSSGGGGSGGGGSGGGGSDIQMTQSPSFLS

ASVGDRVTITCRASQGIISYLAWYQQKPEKAPKRLIYAASSLQSGVPSRFSGSGSGTE

FTLTISSLQPEDFATYYCGQYANYPYTFGQGTKLEIKLEPKSCDKTHTCPPCPDPKFW

VLVVVGGVLACYSLLVTVAFIIFWVRSKRSRLLHSDYMNMTPRRPGPTRKHYQPYA

PPRDFAAYRSRVKFSRSADAPAYKQGQNQLYNELNLGRREEYDVLDKRRGRDPEM

GGKPRRKNPQEGLYNELQKDKMAEAYSEIGMKGERRRGKGHDGLYQGLSTATKDT

YDALHMQALPPR
```

EphA3 CAR K084 (L2H-28z) Amino Acid Sequence

```
                                                    (SEQ ID NO: 14)
MALPVTALLLPLALLLHAARPDIQMTQSPSFLSASVGDRVTITCRASQGIISYLAWYQ

QKPEKAPKRLIYAASSLQSGVPSRFSGSGSGTEFTLTISSLQPEDFATYYCGQYANYP

YTFGQGTKLEIKGGGGSGGGGSGGGGSQVQLVQSGAEVKKPGASVKVSCKASGYTF

TGYWMNWVRQAPGQGLEWMGDIYPGSGNTNYDEKFQGRVTMTRDTSISTAYMEL

SRLRSDDTAVYYCARGGYYEDFDSWGQGTTVTVSSLEPKSCDKTHTCPPCPDPKFW

VLVVVGGVLACYSLLVTVAFIIFWVRSKRSRLLHSDYMNMTPRRPGPTRKHYQPYA

PPRDFAAYRSRVKFSRSADAPAYKQGQNQLYNELNLGRREEYDVLDKRRGRDPEM

GGKPRRKNPQEGLYNELQKDKMAEAYSEIGMKGERRRGKGHDGLYQGLSTATKDT

YDALHMQALPPR
```

EphA3 CAR K085 (L2H BBz) Amino Acid Sequence

```
                                                    (SEQ ID NO: 15)
MALPVTALLLPLALLLHAARPDIQMTQSPSFLSASVGDRVTITCRASQGIISYLAWYQ

QKPEKAPKRLIYAASSLQSGVPSRFSGSGSGTEFTLTISSLQPEDFATYYCGQYANYP

YTFGQGTKLEIKGGGGSGGGGSGGGGSQVQLVQSGAEVKKPGASVKVSCKASGYTF

TGYWMNWVRQAPGQGLEWMGDIYPGSGNTNYDEKFQGRVTMTRDTSISTAYMEL

SRLRSDDTAVYYCARGGYYEDFDSWGQGTTVTVSSTTTPAPRPPTPAPTIASQPLSLR

PEACRPAAGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIGMKGER

RRGKGHDGLYQGLSTATKDTYDALHMQALPPR
```

A CAR that binds to human EphA3 and to human mutant epidermal growth factor receptor variant III (EGFRvIII) was constructed.

We constructed a chimeric antigen receptor that binds to human mutant epidermal growth factor receptor variant III (EGFRvIII) using the following nucleic acid sequence, wherein the intracellular signaling domain comprises a 4-1BB costimulatory domain:
EGFRViii CART (3C10-41BBz)

(SEQ ID NO: 42)
ATGGCCTTACCAGTTACCGCCTTATTATTGCCTTTAGCCTTATTGTTACATGCCGC

CCGTCCGGGATCCGAGATTCAGCTGCAGCAATCTGGGGCAGAACTTGTGAAGCC

AGGGGCCTCAGTCAAGCTGTCCTGCACAGGTTCTGGCTTCAACATTGAAGACTAC

TATATTCACTGGGTGAAGCAGAGGACTGAACAGGGCCTGGAATGGATTGGAAGG

ATTGATCCTGAGAATGATGAAACTAAATATGGCCCAATATTCCAGGGCAGGGCC

ACTATAACAGCAGACACATCCTCCAACACAGTCTACCTGCAACTCAGCAGCCTG

ACATCTGAGGACACTGCCGTCTATTACTGTGCCTTTCGCGGTGGAGTCTACTGGG

GGCCAGGAACCACTCTCACAGTCTCCTCAGGAGGTGGTGGTTCCGGTGGTGGTG

GTTCCGGAGGTGGTGGTTCACATATGGATGTTGTGATGACCCAGTCTCCACTCAC

TCTATCGGTTGCCATTGGACAATCAGCCTCCATCTCTTGCAAGTCAAGTCAGAGC

CTCTTAGATAGTGATGGAAAGACATATTTGAATTGGTTGTTACAGAGGCCAGGCC

AGTCTCCAAAGCGCCTAATCTCTCTGGTGTCTAAACTGGACTCTGGAGTCCCTGA

CAGGTTCACTGGCAGTGGATCAGGGACAGATTTCACACTGAGAATCAGCAGAGT

GGAGGCTGAGGATTTGGGAATTTATTATTGCTGGCAAGGTACACATTTTCCTGGG

ACGTTCGGTGGAGGGACCAAGCTGGAGATAAAAGCTAGCACCACTACCCCTGCA

CCGCGACCACCAACACCGGCGCCCACCATTGCGTCGCAGCCTCTGTCCCTGCGCC

CAGAAGCATGCCGTCCAGCAGCAGGTGGTGCAGTTCATACTCGTGGTCTGGATTT

CGCCTGTGATATCTACATCTGGGCGCCCTTGGCCGGGACTTGTGGGGTCCTTCTC

CTGTCACTGGTTATCACCCTTTACTGCAAACGGGGCAGAAAGAAACTCCTGTATA

TATTCAAACAACCATTTATGAGACCAGTACAAACTACTCAAGAGGAAGATGGCT

GTAGCTGCCGATTTCCAGAAGAAGAAGAAGGAGGATGTGAACTGAGAGTGAAGT

TCAGCAGGAGCGCAGACGCCCCCGCGTACAAGCAGGGCCAGAACCAGCTCTATA

ACGAGCTCAATCTAGGACGAAGAGAGGAGTACGATGTTTTGGACAAGAGACGTG

GCCGGGACCCTGAGATGGGGGAAAGCCGAGAAGGAAGAACCCTCAGGAAGGC

CTGTACAATGAACTGCAGAAAGATAAGATGGCGGAGGCCTACAGTGAGATTGGG

ATGAAAGGCGAGCGCCGGAGGGGCAAGGGGCACGATGGCCTTTACCAGGGTCTC

AGTACAGCCACCAAGGACACCTACGACGCCCTTCACATGCAGGCCCTGCCCCCTC

GCTAA.

The encoded chimeric antigen receptor (CAR) that binds to human mutant epidermal growth factor receptor variant III (EGFRvIII) comprises the following amino acid sequence:
EGFRViii CART (3C10-41BBz) Amino Acid Sequence (SEQ ID NO: 43)
MALPVTALLLPLALLLHAARPGSEIQLQQSGAELVKPGASVKLSCTGSGFNIEDYYIH

WVKQRTEQGLEWIGRIDPENDETKYGPIFQGRATITADTSSNTVYLQLSSLTSEDTAV

YYCAFRGGVYWGPGTTLTVSSGGGGSGGGGSGGGGSHMDVVMTQSPLTLSVAIGQ

SASISCKSSQSLLDSDGKTYLNWLLQRPGQSPKRLISLVSKLDSGVPDRFTGSGSGTD

FTLRISRVEAEDLGIYYCWQGTHFPGTFGGGTKLEIKASTTTPAPRPPTPAPTIASQPLS

-continued

LRPEACRPAAGGAVHTRGLDFACDIYIWAPLAGTCGVLLLSLVITLYCKRGRKKLLY

IFKQPFMRPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEIGMKGE

RRRGKGHDGLYQGLSTATKDTYDALHMQALPPR.

EXAMPLES

Example 2A

Methods

We developed a second generation CD28 co-stimulated CAR constructs in a third generation lentivirus backbone to generate EphA3 CART cells using the single chain variable fragment of ifabotuzumab, a monoclonal antibody directed against EphA3. Patient derived GBM xenograft cell lines were used in these experiments. The EphA3 CART construct was designed and then synthesized de novo using a commercially available protein synthesis vendor using the following DNA sequences, as were three additional EphA-3 CART constructs, respectively:

EphA3 CAR K082 (H2L-BBz)

(SEQ ID NO: 16)
```
ATGGCCTTACCAGTGACCGCCTTGCTCCTGCCGCTGGCCTTGCTGCTCCACGCCG

CCAGGCCGCAGGTGCAGCTGGTGCAGTCTGGGGCTGAGGTGAAGAAGCCTGGGG

CCTCAGTGAAGGTTTCCTGCAAGGCTTCTGGATACACCTTCACAGGCTACTGGAT

GAATTGGGTGCGCCAGGCCCCCGGGCAAGGCCTGGAGTGGATGGGGGACATCTA

CCCGGGCAGTGGTAACACAAACTACGATGAGAAGTTCCAGGGTAGAGTCACGAT

GACCAGGGACACGTCCATCAGCACAGCCTACATGGAGCTGAGCAGGCTGAGATC

TGACGACACAGCCGTGTACTACTGCGCAAGAGGTGGATATTATGAAGATTTTGAT

AGCTGGGGCCAAGGTACCACTGTGACCGTGAGCTCCGGTGGAGGTGGTTCGGGA

GGTGGAGGTAGCGGAGGTGGTGGATCTGACATCCAGATGACCCAGTCTCCATCC

TTCCTGTCTGCATCTGTAGGAGACAGAGTCACCATCACTTGCCGGGCCAGTCAGG

GCATTATCAGTTATTTAGCCTGGTATCAGCAAAAACCAGAGAAAGCCCCTAAGC

GCCTGATCTATGCTGCATCCAGTTTGCAAAGTGGGGTCCCATCAAGGTTCAGCGG

CAGTGGATCTGGGACAGAATTCACTCTCACAATCAGCAGCCTGCAGCCTGAAGA

TTTTGCAACTTACTACTGCGGGCAGTATGCCAATTATCCGTACACCTTTGGCCAA

GGTACGAAACTGGAAATTAAAACCACTACCCCTGCACCGCGACCACCAACACCG

GCGCCCACCATTGCGTCGCAGCCTCTGTCCCTGCGCCCAGAAGCATGCCGTCCAG

CAGCAGGTGGTGCAGTTCATACTCGTGGTCTGGATTTCGCCTGTGATATCTACAT

CTGGGCGCCCTTGGCCGGGACTTGTGGGGTCCTTCTCCTGTCACTGGTTATCACC

CTTTACTGCAAACGGGGCAGAAAGAAACTCCTGTATATATTCAAACAACCATTTA

TGAGACCAGTACAAACTACTCAAGAGGAAGATGGCTGTAGCTGCCGATTTCCAG

AAGAAGAAGAAGGAGGATGTGAACTGAGAGTGAAGTTCAGCAGGAGCGCAGAC

GCCCCCGCGTACAAGCAGGGCCAGAACCAGCTCTATAACGAGCTCAATCTAGGA

CGAAGAGAGGAGTACGATGTTTTGGACAAGAGACGTGGCCGGGACCCTGAGATG

GGGGGAAAGCCGAGAAGGAAGAACCCTCAGGAAGGCCTGTACAATGAACTGCA

GAAAGATAAGATGGCGGAGGCCTACAGTGAGATTGGGATGAAAGGCGAGCGCC

GGAGGGGCAAGGGGCACGATGGCCTTTACCAGGGTCTCAGTACAGCCACCAAGG

ACACCTACGACGCCCTTCACATGCAGGCCCTGCCCCCTCGC
```

EPHA3 CAR K083 (H2L-28z)

(SEQ ID NO: 17)
```
ATGGCCTTACCAGTGACCGCCTTGCTCCTGCCGCTGGCCTTGCTGCTCCACGCCG
CCAGGCCGCAGGTGCAGCTGGTGCAGTCTGGGGCTGAGGTGAAGAAGCCTGGGG
CCTCAGTGAAGGTTTCCTGCAAGGCTTCTGGATACACCTTCACAGGCTACTGGAT
GAATTGGGTGCGCCAGGCCCCCGGGCAAGGCTGGAGTGGATGGGGGACATCTA
CCCGGGCAGTGGTAACACAAACTACGATGAGAAGTTCCAGGGTAGAGTCACGAT
GACCAGGGACACGTCCATCAGCACAGCCTACATGGAGCTGAGCAGGCTGAGATC
TGACGACACAGCCGTGTACTACTGCGCAAGAGGTGGATATTATGAAGATTTTGAT
AGCTGGGGCCAAGGTACCACTGTGACCGTGAGCTCCGGTGGAGGTGGTTCGGGA
GGTGGAGGTAGCGGAGGTGGTGGATCTGACATCCAGATGACCCAGTCTCCATCC
TTCCTGTCTGCATCTGTAGGAGACAGAGTCACCATCACTTGCCGGGCCAGTCAGG
GCATTATCAGTTATTTAGCCTGGTATCAGCAAAAACCAGAGAAAGCCCCTAAGC
GCCTGATCTATGCTGCATCCAGTTTGCAAAGTGGGGTCCCATCAAGGTTCAGCGG
CAGTGGATCTGGGACAGAATTCACTCTCACAATCAGCAGCCTGCAGCCTGAAGA
TTTTGCAACTTACTACTGCGGGCAGTATGCCAATTATCCGTACACCTTTGGCCAA
GGTACGAAACTGGAAATTAAACTCGAGCCCAAATCTTGTGACAAAACTCACACA
TGCCCACCGTGCCCGGATCCCAAATTTTGGGTGCTGGTGGTGGTTGGTGGAGTCC
TGGCTTGCTATAGCTTGCTAGTAACAGTGGCCTTTATTATTTTCTGGGTGAGGAGT
AAGAGGAGCAGGCTCCTGCACAGTGACTACATGAACATGACTCCCCGCCGCCCC
GGGCCCACCCGCAAGCATTACCAGCCCTATGCCCCACCACGCGACTTCGCAGCCT
ATCGCTCCAGAGTGAAGTTCAGCAGGAGCGCAGACGCCCCCGCGTACAAGCAGG
GCCAGAACCAGCTCTATAACGAGCTCAATCTAGGACGAAGAGAGGAGTACGATG
TTTTGGACAAGAGACGTGGCCGGGACCCTGAGATGGGGGGAAAGCCGAGAAGG
AAGAACCCTCAGGAAGGCCTGTACAATGAACTGCAGAAAGATAAGATGGCGGA
GGCCTACAGTGAGATTGGGATGAAAGGCGAGCGCCGGAGGGGCAAGGGCACG
ATGGCCTTTACCAGGGTCTCAGTACAGCCACCAAGGACACCTACGACGCCCTTCA
CATGCAGGCCCTGCCCCCTCGC
```

EPHA3 CAR K084 (L2H-28z)

(SEQ ID NO: 18)
```
ATGGCCTTACCAGTGACCGCCTTGCTCCTGCCGCTGGCCTTGCTGCTCCACGCCG
CCAGGCCGGACATCCAGATGACCCAGTCTCCATCCTTCCTGTCTGCATCTGTAGG
AGACAGAGTCACCATCACTTGCCGGGCCAGTCAGGGCATTATCAGTTATTTAGCC
TGGTATCAGCAAAAACCAGAGAAAGCCCCTAAGCGCCTGATCTATGCTGCATCC
AGTTTGCAAAGTGGGGTCCCATCAAGGTTCAGCGGCAGTGGATCTGGGACAGAA
TTCACTCTCACAATCAGCAGCCTGCAGCCTGAAGATTTTGCAACTTACTACTGCG
GGCAGTATGCCAATTATCCGTACACCTTTGGCCAAGGTACGAAACTGGAAATTA
AAGGTGGAGGTGGTTCGGGAGGTGGAGGTAGCGGAGGTGGTGGATCTCAGGTGC
AGCTGGTGCAGTCTGGGGCTGAGGTGAAGAAGCCTGGGGCCTCAGTGAAGGTTT
CCTGCAAGGCTTCTGGATACACCTTCACAGGCTACTGGATGAATTGGGTGCGCCA
GGCCCCCGGGCAAGGCTGGAGTGGATGGGGGACATCTACCCGGGCAGTGGTAA
```

-continued

```
CACAAACTACGATGAGAAGTTCCAGGGTAGAGTCACGATGACCAGGGACACGTC

CATCAGCACAGCCTACATGGAGCTGAGCAGGCTGAGATCTGACGACACAGCCGT

GTACTACTGCGCAAGAGGTGGATATTATGAAGATTTTGATAGCTGGGGCCAAGG

TACCACTGTGACCGTGAGCTCCCTCGAGCCCAAATCTTGTGACAAAACTCACACA

TGCCCACCGTGCCCGGATCCCAAATTTTGGGTGCTGGTGGTGGTTGGTGGAGTCC

TGGCTTGCTATAGCTTGCTAGTAACAGTGGCCTTTATTATTTTCTGGGTGAGGAGT

AAGAGGAGCAGGCTCCTGCACAGTGACTACATGAACATGACTCCCCGCCGCCCC

GGGCCCACCCGCAAGCATTACCAGCCCTATGCCCCACCACGCGACTTCGCAGCCT

ATCGCTCCAGAGTGAAGTTCAGCAGGAGCGCAGACGCCCCCGCGTACAAGCAGG

GCCAGAACCAGCTCTATAACGAGCTCAATCTAGGACGAAGAGAGGAGTACGATG

TTTTGGACAAGAGACGTGGCCGGGACCCTGAGATGGGGGGAAAGCCGAGAAGG

AAGAACCCTCAGGAAGGCCTGTACAATGAACTGCAGAAAGATAAGATGGCGGA

GGCCTACAGTGAGATTGGGATGAAAGGCGAGCGCCGGAGGGGCAAGGGGCACG

ATGGCCTTTACCAGGGTCTCAGTACAGCCACCAAGGACACCTACGACGCCCTTCA

CATGCAGGCCCTGCCCCCTCGC
```

EPHA3 CAR K085 (L2H BBz)

(SEQ ID NO: 19)

```
ATGGCCTTACCAGTGACCGCCTTGCTCCTGCCGCTGGCCTTGCTGCTCCACGCCG

CCAGGCCGGACATCCAGATGACCCAGTCTCCATCCTTCCTGTCTGCATCTGTAGG

AGACAGAGTCACCATCACTTGCCGGGCCAGTCAGGGCATTATCAGTTATTTAGCC

TGGTATCAGCAAAAACCAGAGAAAGCCCCTAAGCGCCTGATCTATGCTGCATCC

AGTTTGCAAAGTGGGGTCCCATCAAGGTTCAGCGGCAGTGGATCTGGGACAGAA

TTCACTCTCACAATCAGCAGCCTGCAGCCTGAAGATTTTGCAACTTACTACTGCG

GGCAGTATGCCAATTATCCGTACACCTTTGGCCAAGGTACGAAACTGGAAATTA

AAGGTGGAGGTGGTTCGGGAGGTGGAGGTAGCGGAGGTGGTGGATCTCAGGTGC

AGCTGGTGCAGTCTGGGGCTGAGGTGAAGAAGCCTGGGGCCTCAGTGAAGGTTT

CCTGCAAGGCTTCTGGATACACCTTCACAGGCTACTGGATGAATTGGGTGCGCCA

GGCCCCCGGGCAAGGCCTGGAGTGGATGGGGGACATCTACCCGGGCAGTGGTAA

CACAAACTACGATGAGAAGTTCCAGGGTAGAGTCACGATGACCAGGGACACGTC

CATCAGCACAGCCTACATGGAGCTGAGCAGGCTGAGATCTGACGACACAGCCGT

GTACTACTGCGCAAGAGGTGGATATTATGAAGATTTTGATAGCTGGGGCCAAGG

TACCACTGTGACCGTGAGCTCCACCACTACCCCTGCACCGCGACCACCAACACCG

GCGCCCACCATTGCGTCGCAGCCTCTGTCCCTGCGCCCAGAAGCATGCCGTCCAG

CAGCAGGTGGTGCAGTTCATACTCGTGGTCTGGATTTCGCCTGTGATATCTACAT

CTGGGCGCCCTTGGCCGGGACTTGTGGGGTCCTTCTCCTGTCACTGGTTATCACC

CTTTACTGCAAACGGGGCAGAAAGAAACTCCTGTATATATTCAAACAACCATTTA

TGAGACCAGTACAAACTACTCAAGAGGAAGATGGCTGTAGCTGCCGATTTCCAG

AAGAAGAAGAAGGAGGATGTGAACTGAGAGTGAAGTTCAGCAGGAGCGCAGAC

GCCCCCGCGTACAAGCAGGGCCAGAACCAGCTCTATAACGAGCTCAATCTAGGA

CGAAGAGAGGAGTACGATGTTTTGGACAAGAGACGTGGCCGGGACCCTGAGATG
```

```
GGGGGAAAGCCGAGAAGGAAGAACCCTCAGGAAGGCCTGTACAATGAACTGCA

GAAAGATAAGATGGCGGAGGCCTACAGTGAGATTGGGATGAAAGGCGAGCGCC

GGAGGGGCAAGGGGCACGATGGCCTTTACCAGGGTCTCAGTACAGCCACCAAGG

ACACCTACGACGCCCTTCACATGCAGGCCCTGCCCCCTCGC
```

The EphA3 CAR construct was subsequently cloned into a third generation lentivirus under control of an EF-1α promoter. The single chain variable region fragment is a proprietary sequence produced by Humanigen. The EphA3 construct possesses a second generation CD28 costimulatory domain and CD3ζ stimulation.

We performed lentiviral production using 293T cells at 70-90% confluency after allowing for incubation for 30 min at room temperature of transfection reagents including 15 μg of the EphaA3 lentiviral plasmid, 18 μg of a gag/pol/tat/rev packaging vector, 7 μg of a VSV-G envelope vector, 111 μL of the pre-complexing reagent, 129 μL of the transfection reagent, and 9.0 mL of the transfection medium before adding to the 293T cells. Then culture the transfected cells at 37° C., 5% CO2. We then harvested the cell media supernatant and concentrated by ultracentrifugation at 112, 700×g for 2 h.

Human T-cells were isolated via a negative selection magnetic bead kit from peripheral blood mononuclear cells (PBMCs) from de-identified normal donor blood cones collected during apheresis. The isolated T cells were then stimulated with magnetic CD3/CD28 beads at a ratio of 3:1 beads:T cells and incubated for 24 hours.

We transduced stimulated T cells with harvested virus at a multiplicity of infection (MOI) of 3.0. CAR-T cells were then expanded by incubation at 37° C., 5% CO2, counted and fed at days 3 and 5 post lentiviral transduction and maintained at a CAR-T cell concentration of 1×10$^6$/mL. Six days after transduction cell surface expression of the CAR was assessed by flow cytometry. 100,000 T cells from the culture were washed with flow buffer prepared with Dulbecco's phosphate-buffered saline, 2% fetal bovine serum, and 1% sodium azide and subsequently stained with anti-CAR antibody (goat anti-mouse was used) and washed twice. The cells were stained with live/dead stain and CD3 monoclonal antibody. The cells were washed and resuspend in flow buffer and subsequently analyzed by flow cytometry to determine transduction efficiency. For killing assays, patient derived GBM xenograft cell lines (gift from Jann Sarkaria's lab) with varying expression of the target antigen by RNA-seq analysis were incubated at the indicated ratios with effector T cells for 24 hours. Killing was calculated by bioluminescence imaging on a Xenogen IVIS-200 Spectrum camera as a measure of residual live cells. Samples were treated with 1 ul D-luciferin (30 μg/mL) per 100 ul sample volume for 10 minutes prior to imaging.

Figures 1A, 1B, 1C:
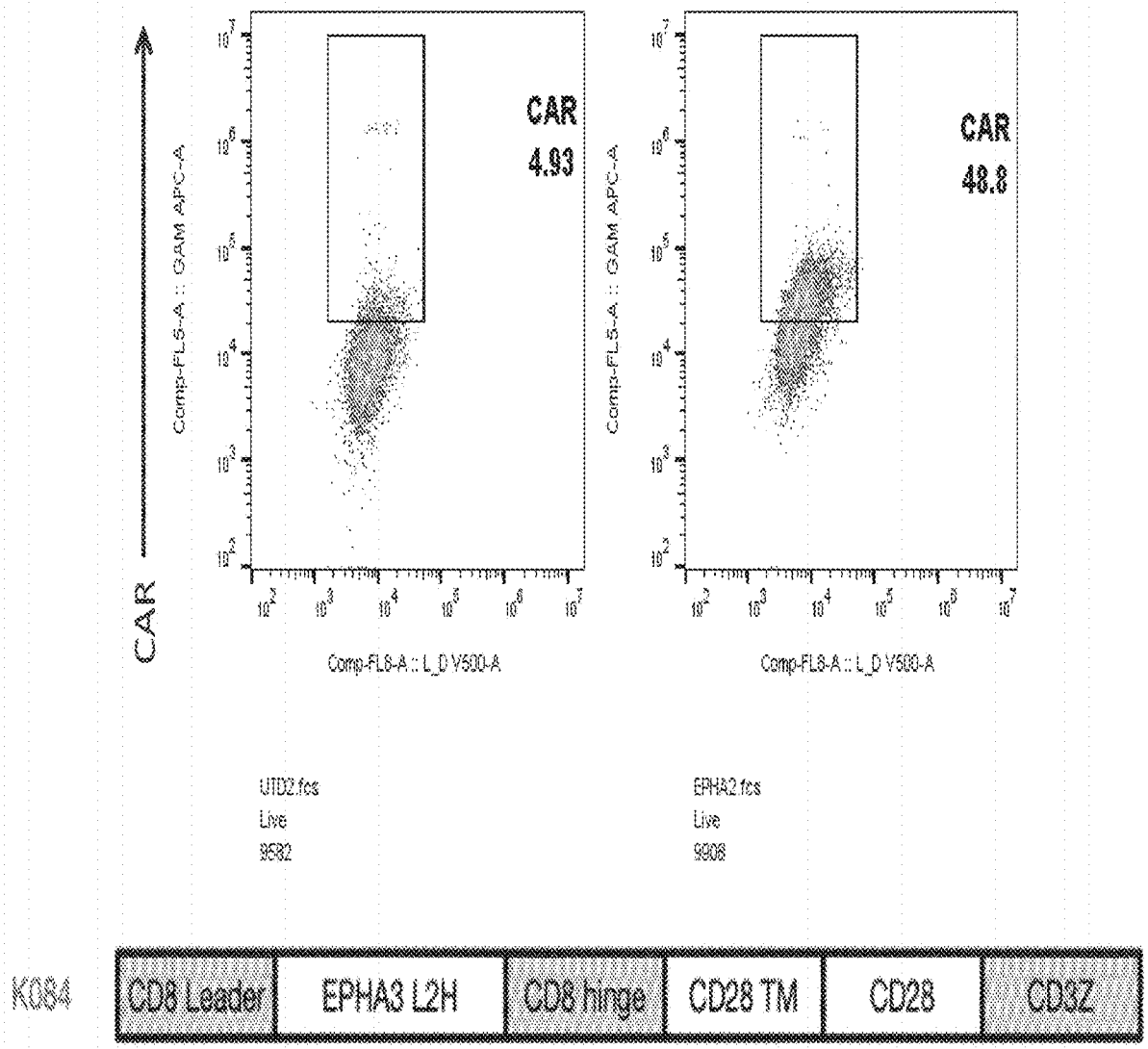
FIGS. 1A-1C show CAR-T cell production of the Epha-3 targeting CAR (termed K84) on the surface of donor T-cells by flow cytometry (FIGS. 1A-1B) and a map of the EphA-3 targeting CAR construct termed K84 (FIG. 1C).
Figures 2A, 2B:
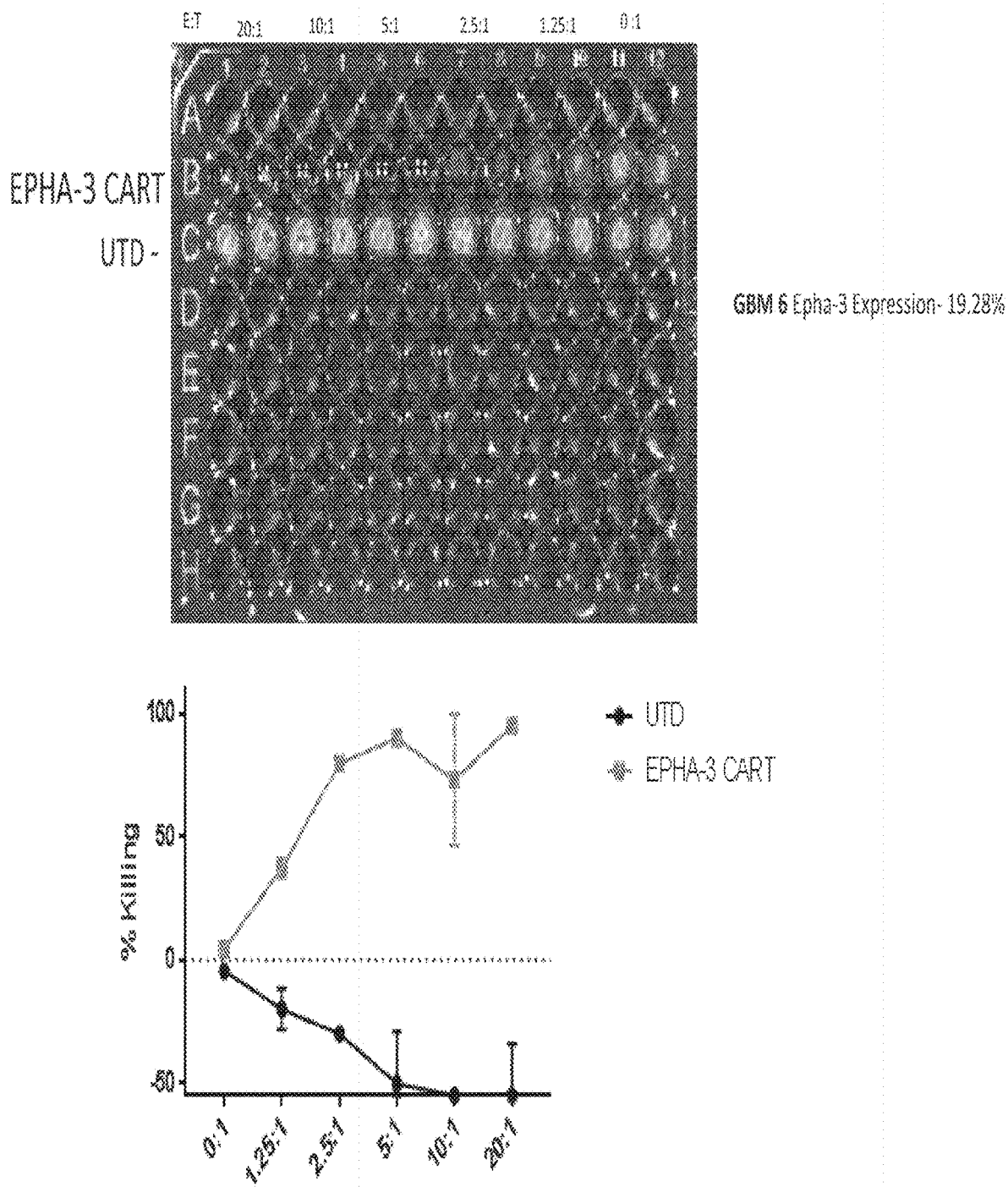
FIGS. 2A-2B show GBM6 killing by the EphA-3 targeting CAR (termed K84) in a 24 hour TdT killing assay compared to un-transduced (UTD) cells from the same donor apheresis cone. The GBM6 EphA-3 expression was 19.28%. The CAR 84 demonstrated significant killing of GBM6 over 24 hours compared to UTD.
Figures 3A, 3B:
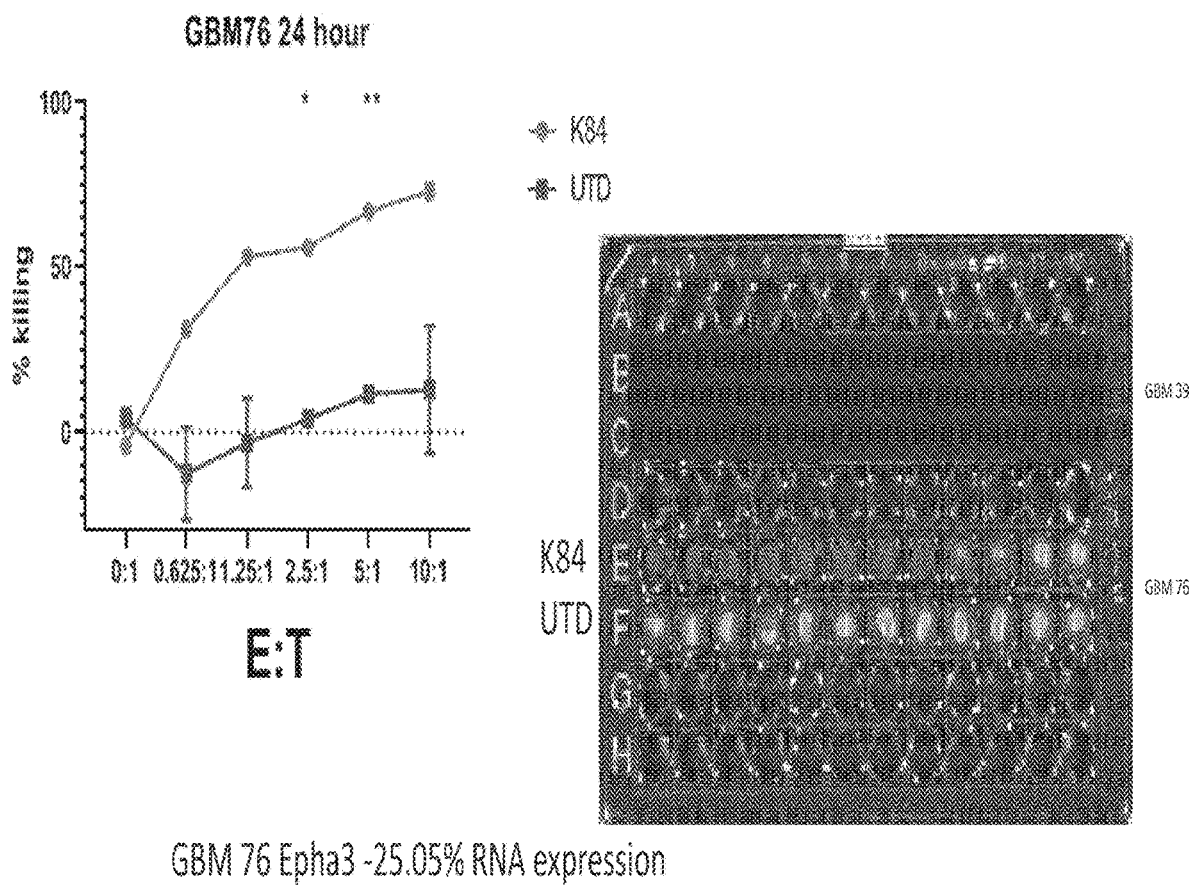
FIGS. 3A-3B show the killing of GBM PDX line 76 ("GBM 76") by EphA-3 targeting CAR (termed K84) in a 24 hour killing assay. The GBM 76 Epha-3 expression was 25.05% RNA expression. The CAR 84 demonstrated significant killing of GBM 76 over 24 hours compared to UTD.
Figure 4A:
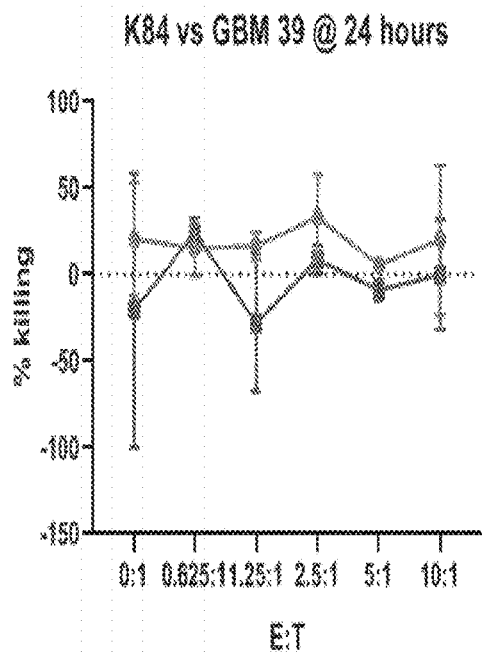
FIGS. 4A-4B show the killing of GBM PDX line 39 ("GBM 39") by EphA-3 targeting CAR (termed K84) in a 24 hour killing assay. There was not a significant difference in killing when co-cultured with cell lines with 6.95% EphA3 expression (FIG. 4A).
Figure 4B:
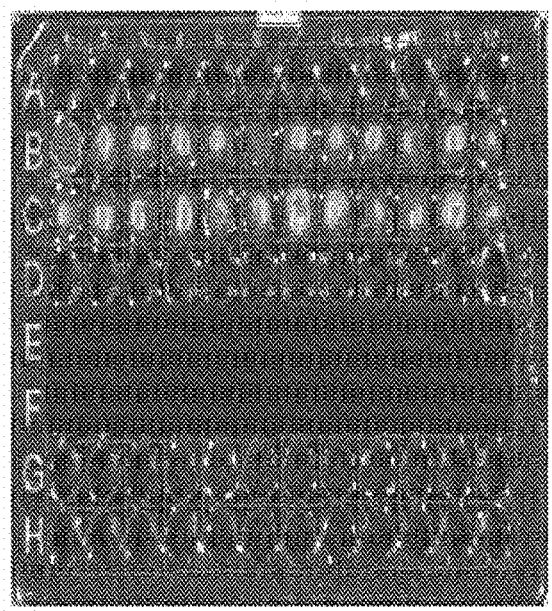
Figures 6A, 6B:
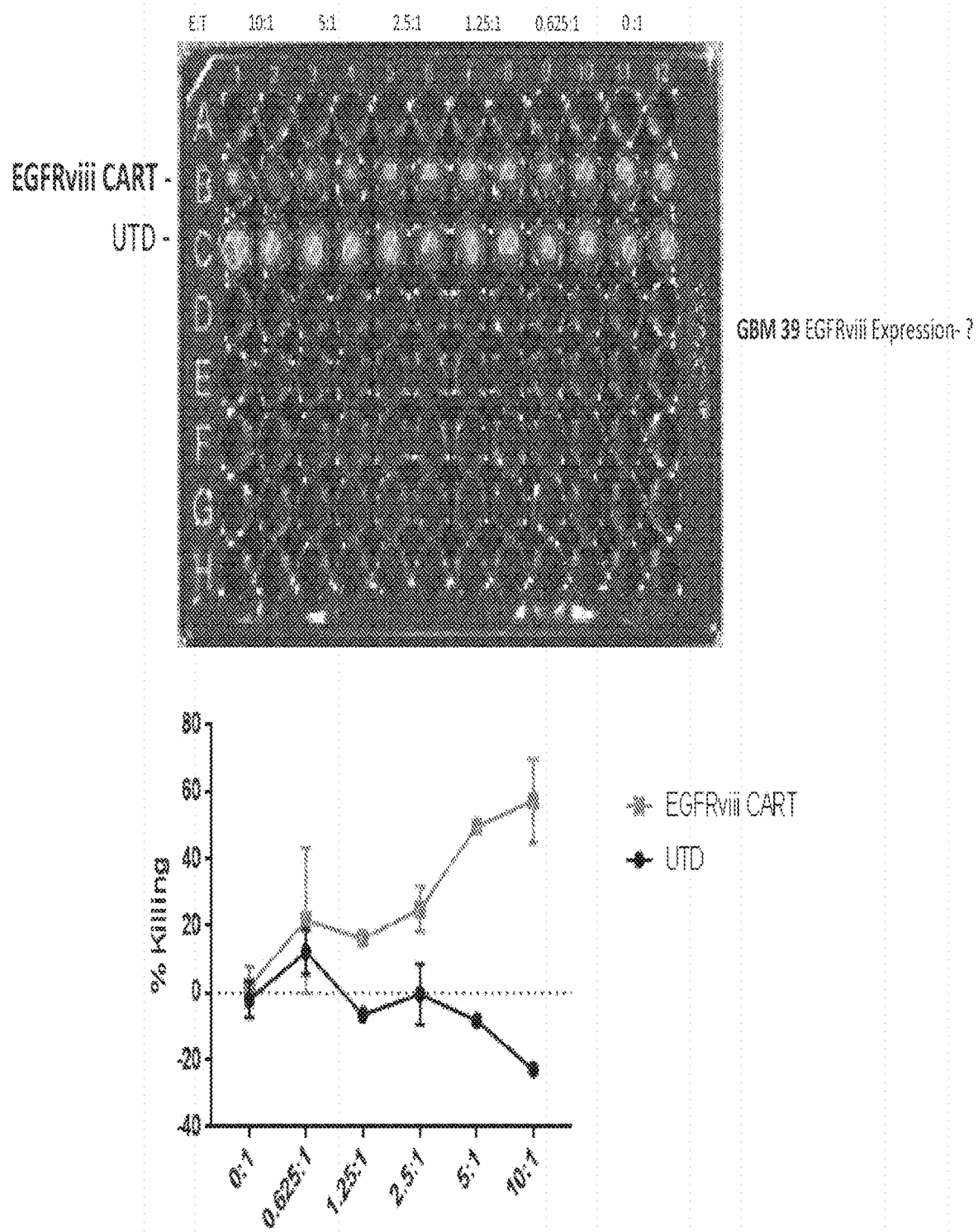
FIGS. 6A-6B show the killing of GBM PDX line 39 ("GBM 39") by EGFRviii targeting CAR (termed K96) in a 24 hour TdT killing assay. The CAR K96 demonstrated significant killing of GBM 39 over 24 hours (from low effector: target ratio of 1.25:1) compared to UTD.
Figures 7A, 7B:
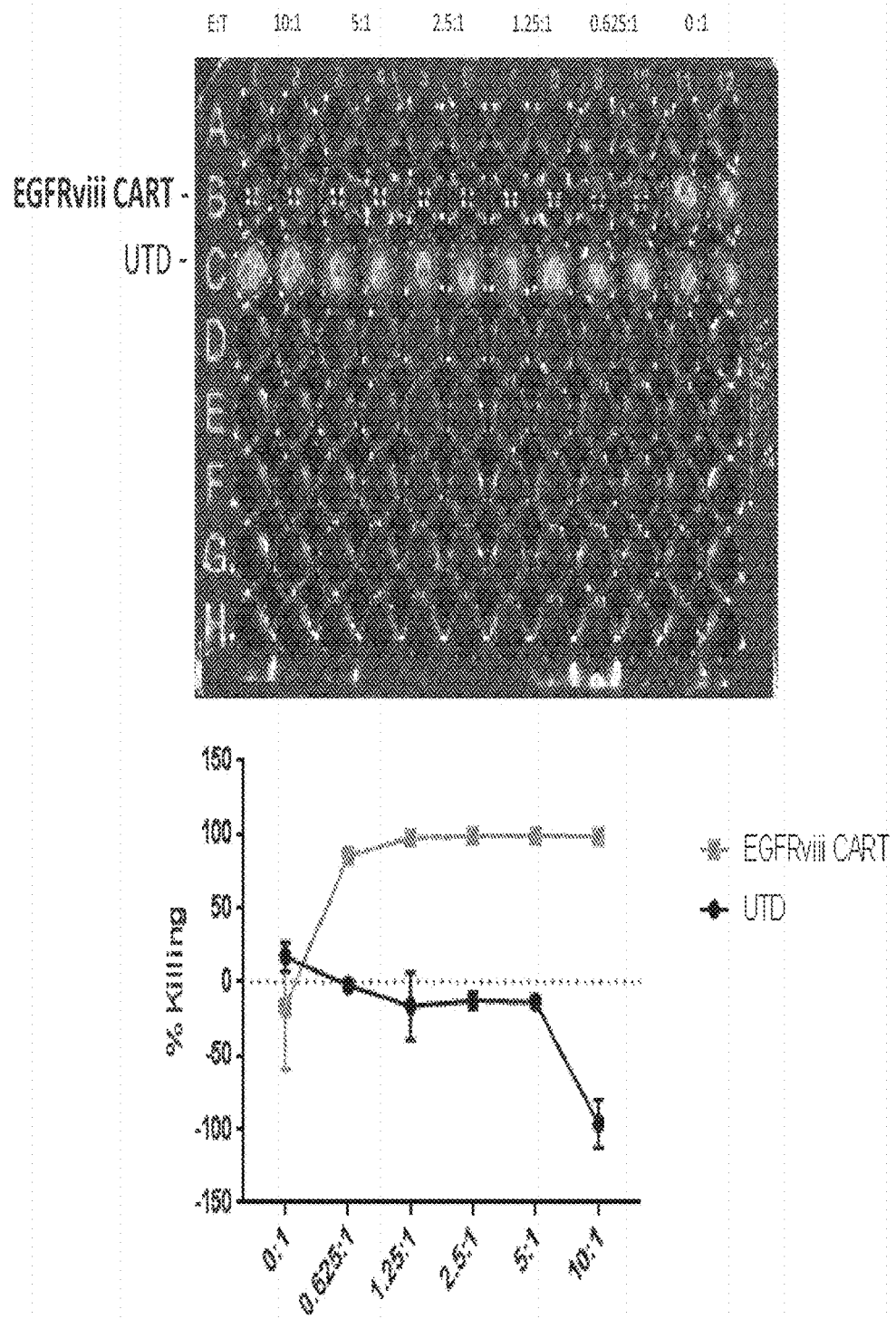
FIGS. 7A-7B show the killing of GBM PDX line 39 ("GBM 39") by EGFRviii targeting CAR (termed K96) in a 48 hour TdT killing assay. The CAR K96 demonstrated significant killing of GBM 39 over 48 hours (from low effector: target ratio of 0.625:1) compared to UTD.
Figures 8A, 8B, 8C:
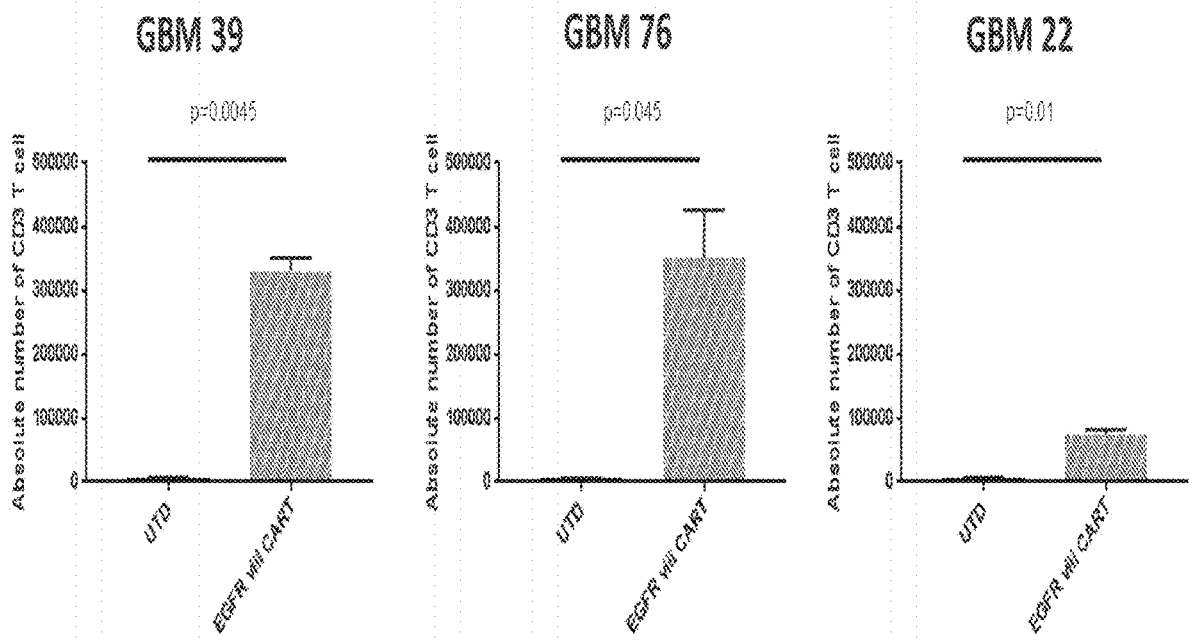
FIGS. 8A-8C show a proliferation assay for K96 EGFRviii targeting CAR-T cells (EGFRviii CART) in a 5 day incubation versus radiated cell lines for GBM 39 (FIG. 8A), GBM 76 (FIG. 8B) and GBM 22 (FIG. 8C) compare to UTD.
Figure 9A:
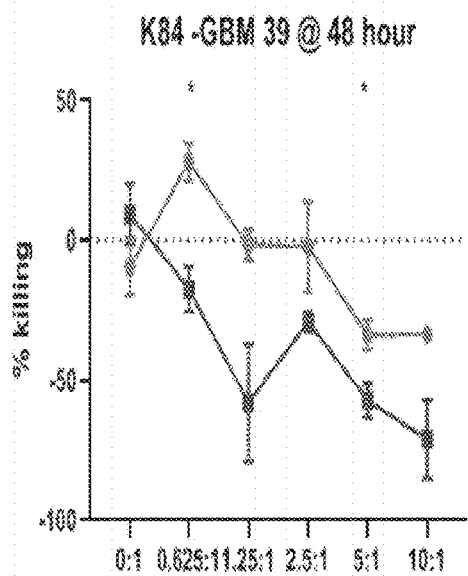
FIGS. 9A-9B show the killing of GBM PDX line 39 ("GBM 39") by Epha-3 targeting CAR (termed K84) in a 48 hour TdT killing assay. The GBM 39 EphA-3 expression was 6.95% RNA expression.
Figure 9B:
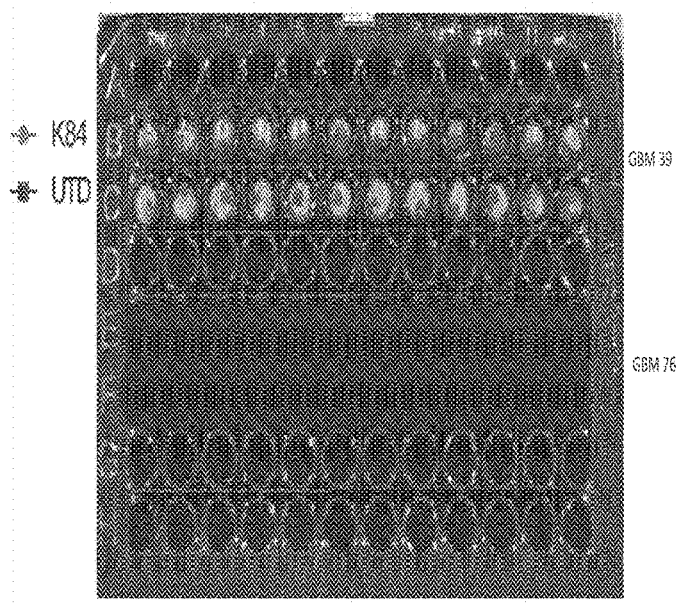
Figures 10A, 10B:
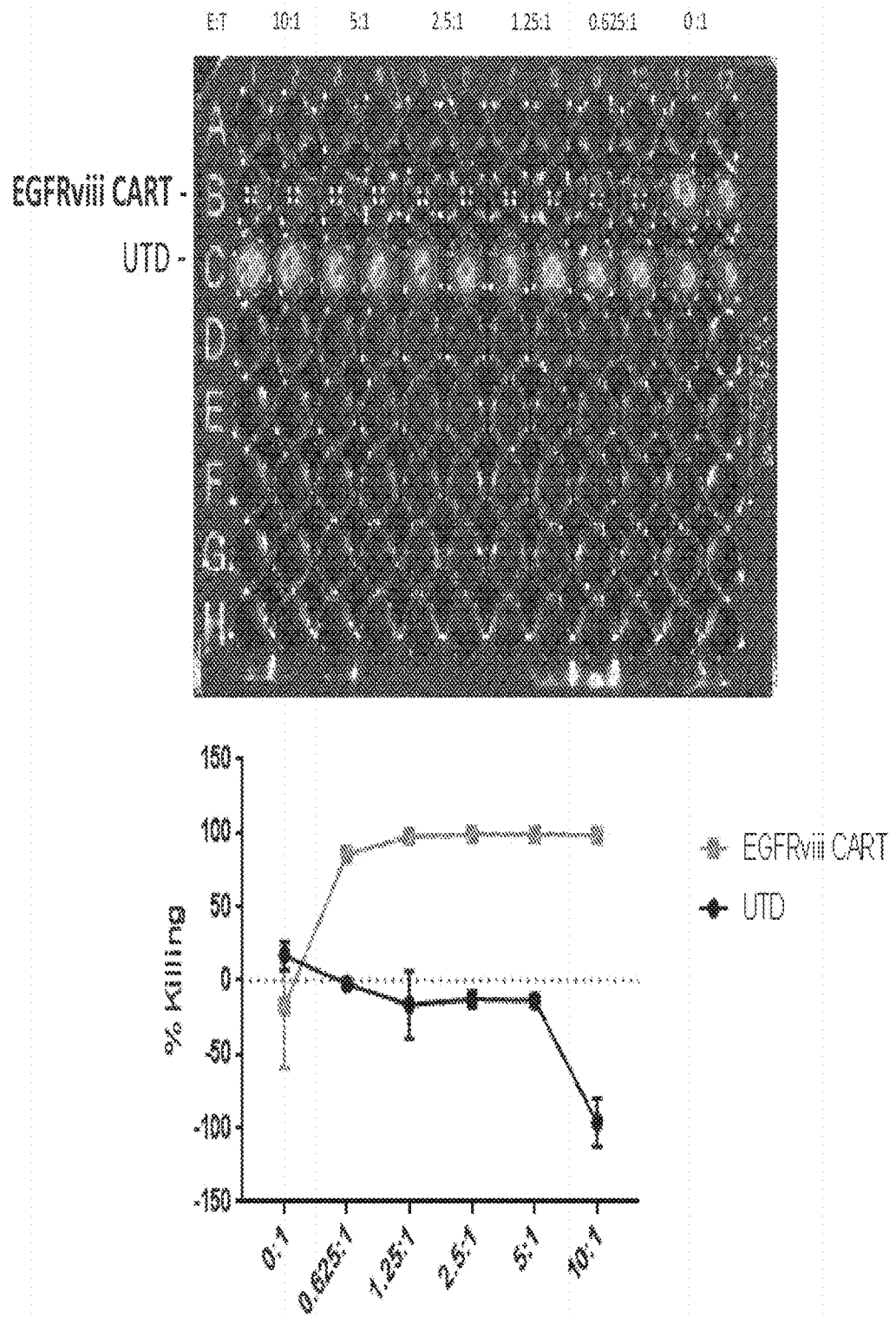
FIGS. 10A-10B show the killing of GBM PDX line 39 ("GBM 39") by EGFRviii targeting CAR (termed K96) in a 48 hour TdT killing assay. The CAR K96 demonstrated significant killing of GBM 39 over 48 hours (from low effector: target ratio of 0.625:1) compared to UTD.
Figure 11:
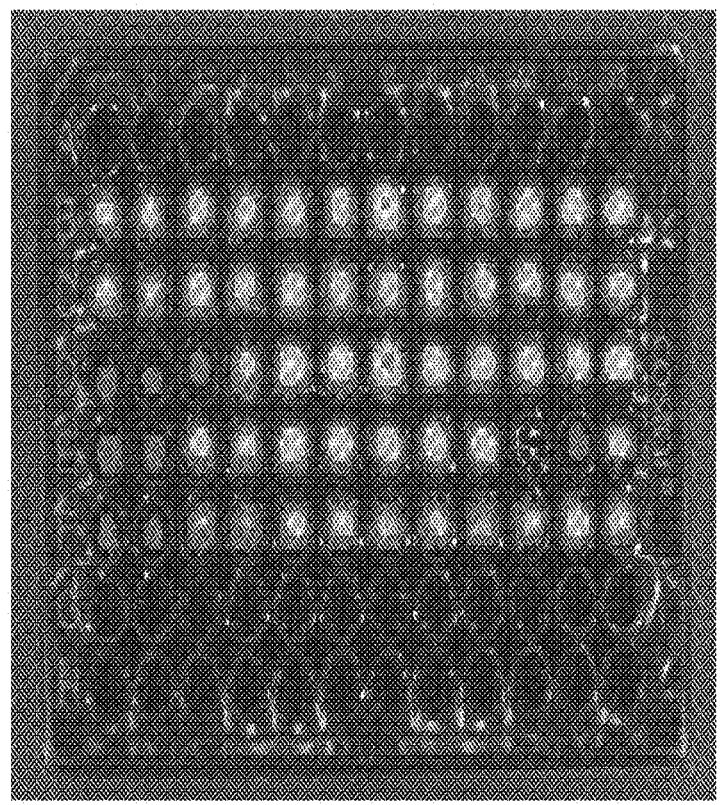
FIG. 11 shows the killing over 24 hours of GBM 76 by K84 (comprising EphA3 targeting CAR cloned into lentivirus), K96 (comprising EGFRviii targeting CAR cloned into lentivirus), "both"=K84+K96" (i.e., CAR T cells were exposed to and cultured with one lentivirus, e.g., K84, and then mixed with CAR T cells exposed to and cultured with the other lentivirus, e.g., K96) and "combinatorial CAR T cells" exposed to and cultured with both lentiviruses K84 and K96 compared to UTD. EGFRviii expression was present in this GBM line and Epha-3 RNA expression was 25.05%. The terms "both"="K84+K96" and "combinatorial CAR T cells" (also called "combi") are used herein throughout as described for FIG. 11.
Figure 12:
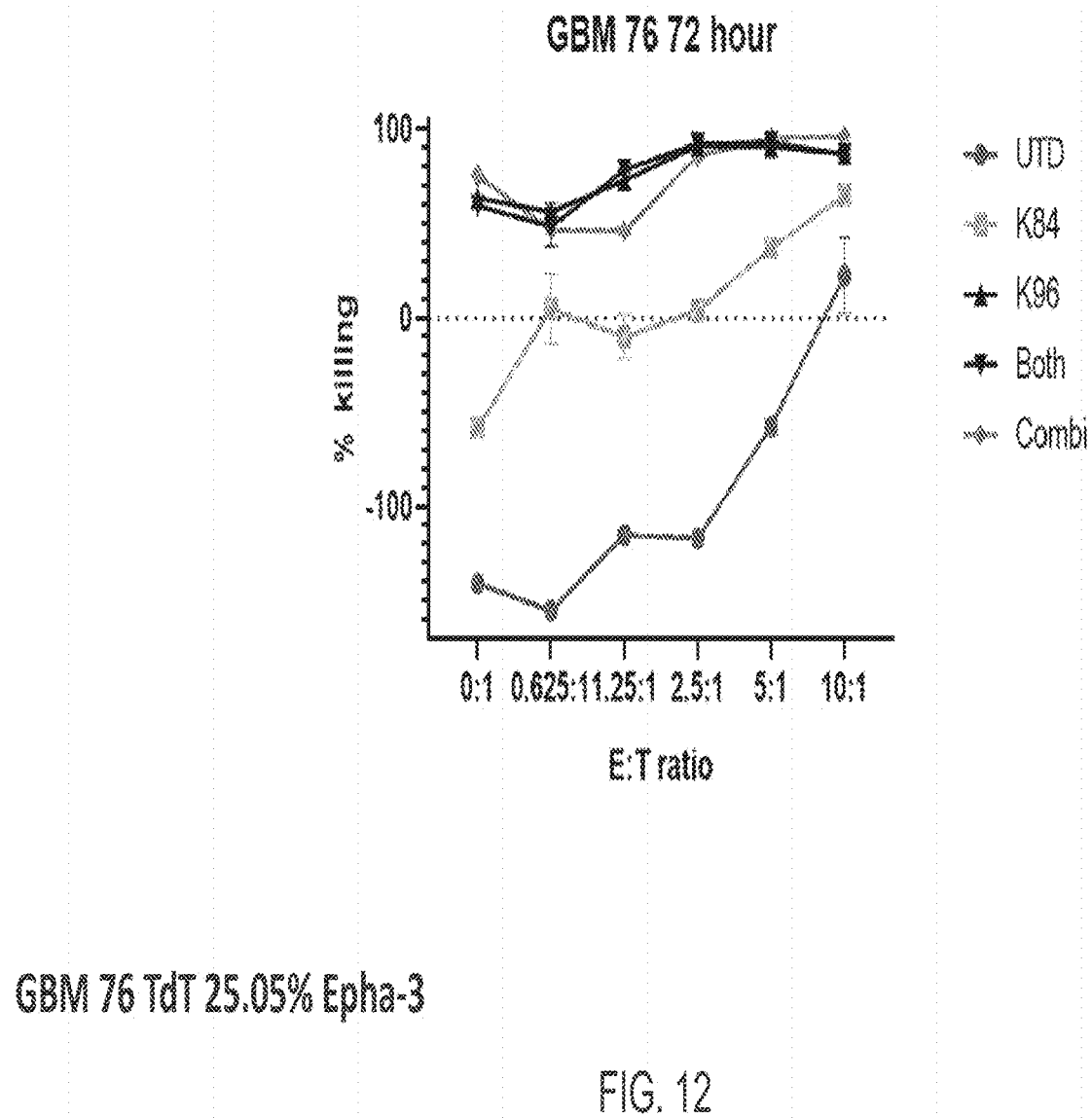
FIG. 12 shows the killing (in a TdT assay) over 72 hours of GBM 76 by K84, K96, "both K84+K96" and "combinatorial CAR T cells" compared to UTD. GBM 76 EphA3 expression was 25.02%.
Figure 13:
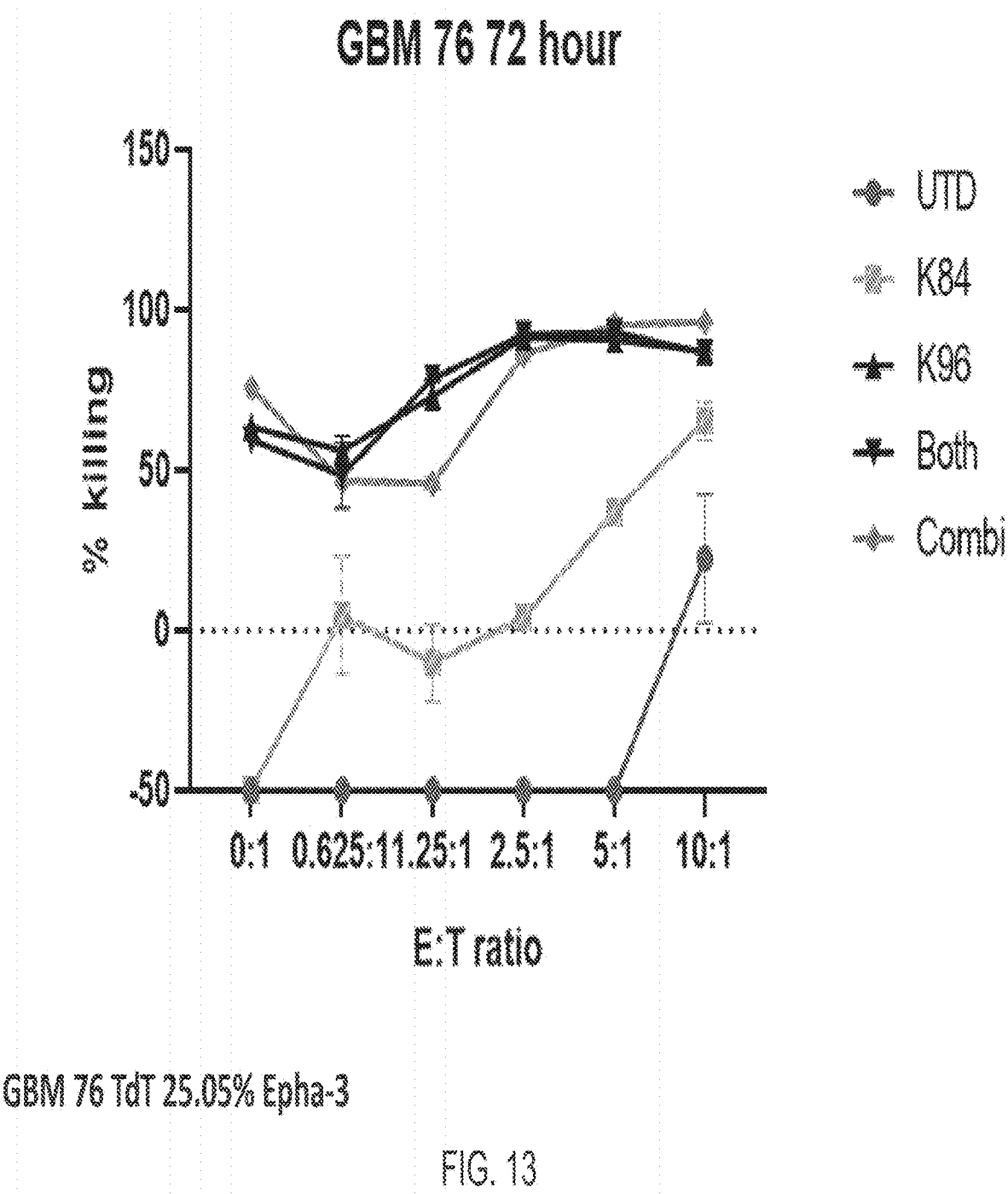
FIG. 13 shows the killing (in a TdT assay) over 72 hours of GBM 76 by K84, K96, "both K84+K96" and "combinatorial CAR T cells" compared to UTD. GBM 76 EphA3 expression was 25.02%.
Figure 14:
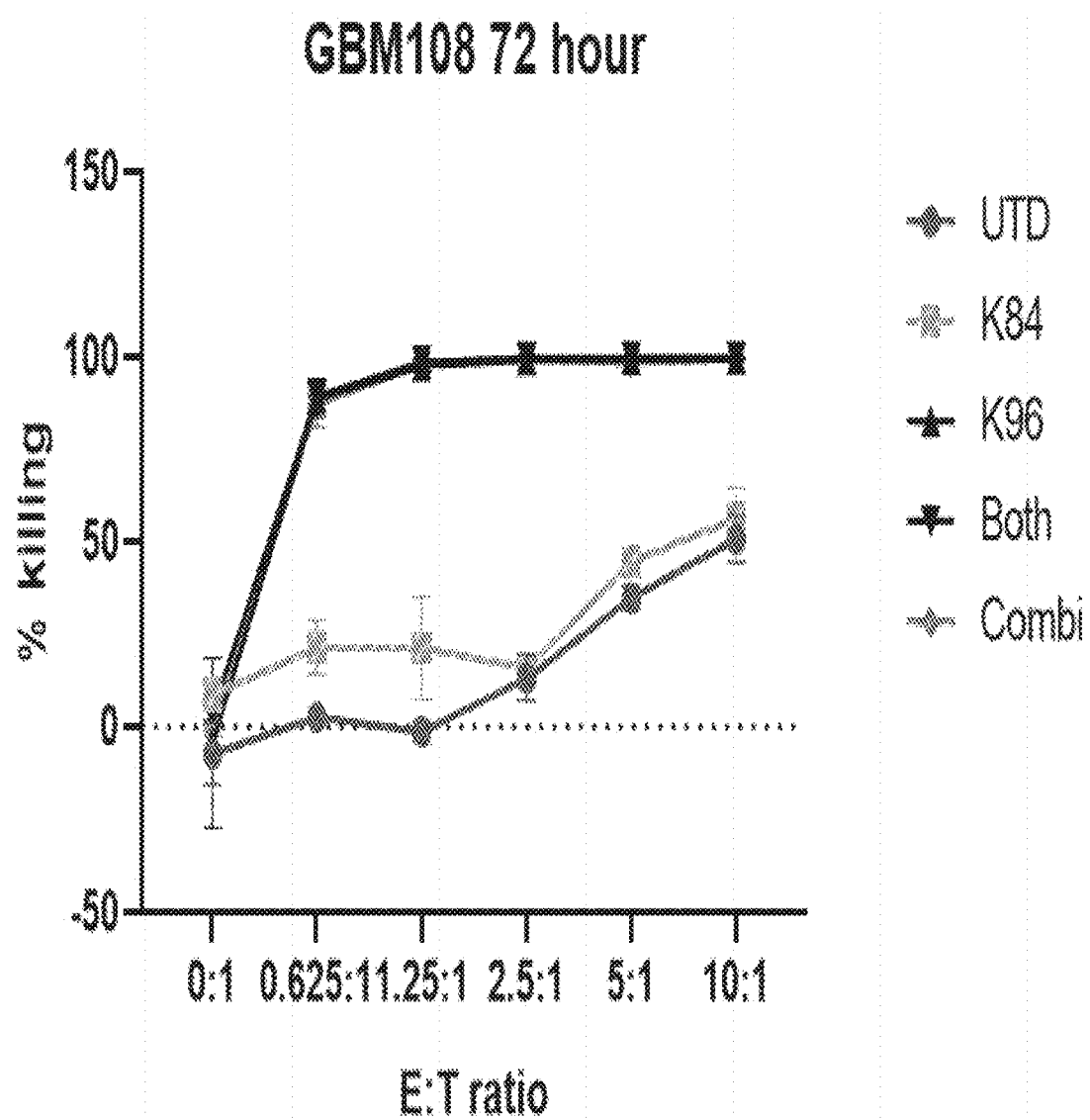
FIG. 14 shows the killing over 72 hours of GBM 108 by K84, K96, "both K84+K96" and "combinatorial CAR T cells" compared to UTD. GBM 76 EphA3 expression was 25.02% compared to UTD. EGFRviii expression was present in this GBM line.
Figure 15A:
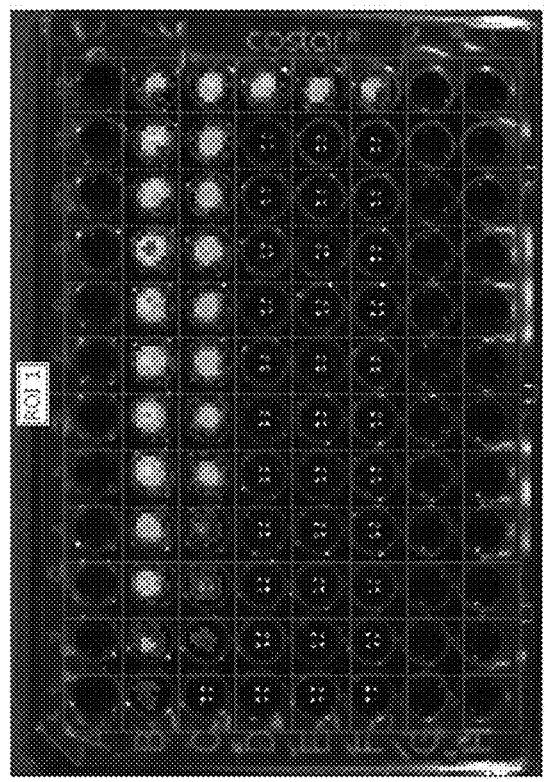
FIGS. 15A-15B show the killing over 7 days incubation of GBM 76 by K84, K96, "both K84+K96" and "combinatorial CAR T cells" compared to UTD. GBM 76 EphA3 expression was 25.02% RNA expression.
Figure 15B:
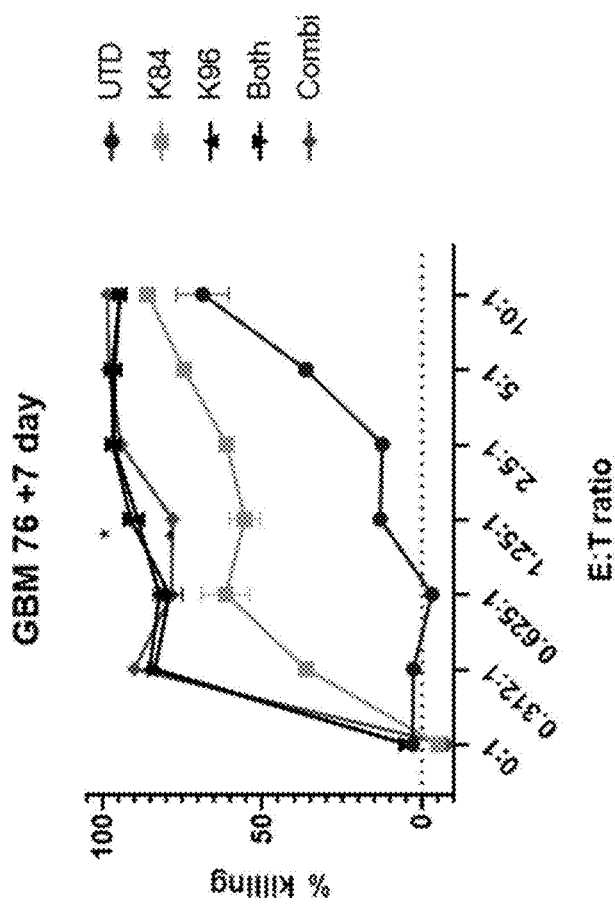
Figure 16A:
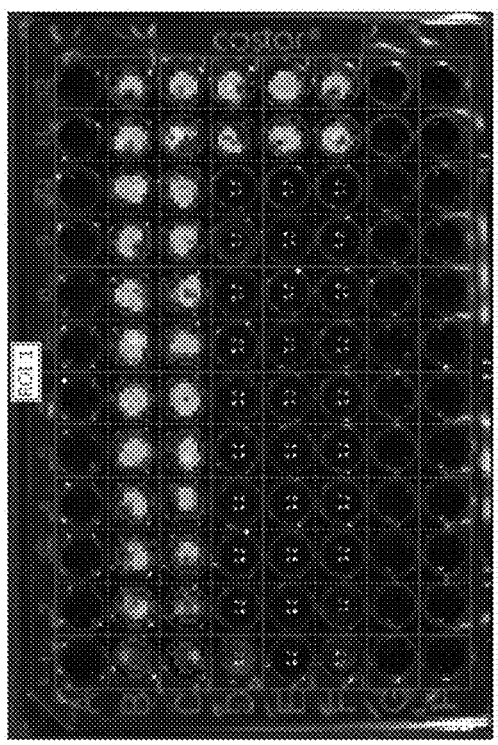
FIGS. 16A-16B show the killing over 7 days incubation of GBM 108 by K84, K96, "both K84+K96" and "combinatorial CAR T cells" compared to UTD. This GBM line showed EphA3 expression of 1.52% RNA expression and EGFRviii expression was present.
Figure 16B:
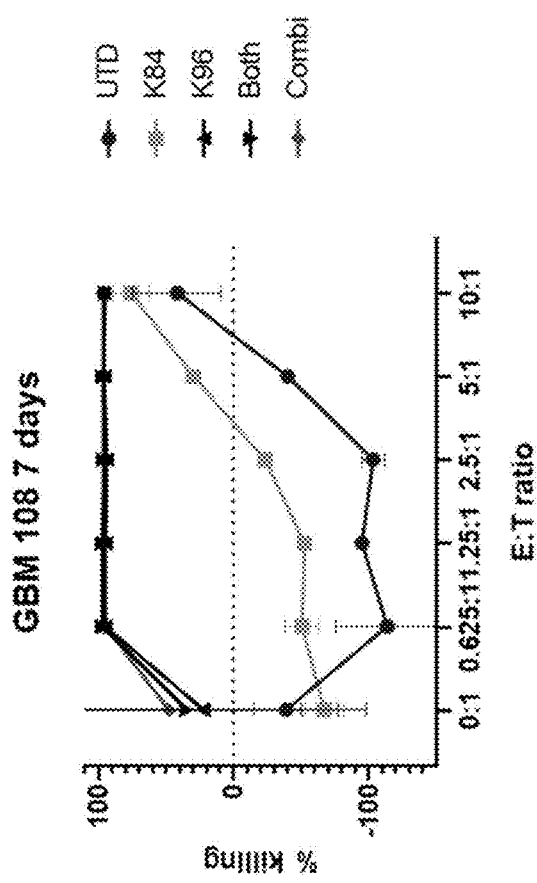
Figure 17:
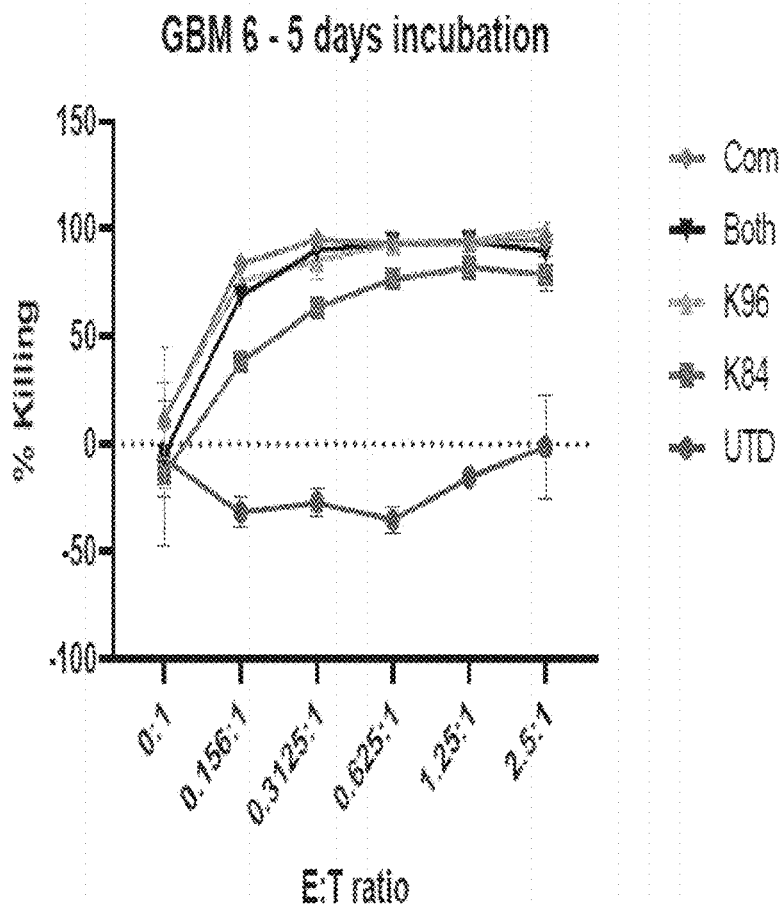
FIG. 17 shows GBM 6 killing assays over 5 days incubation by CAR T cells: K84, K96, "both K84+K96" and "combinatorial CAR T cells" compared to UTD. GBM 6 EphA3 showed 19.28% expression per RNA seq; this GBM does have (expresses) EGFR and EGFRviii.
Figure 18:
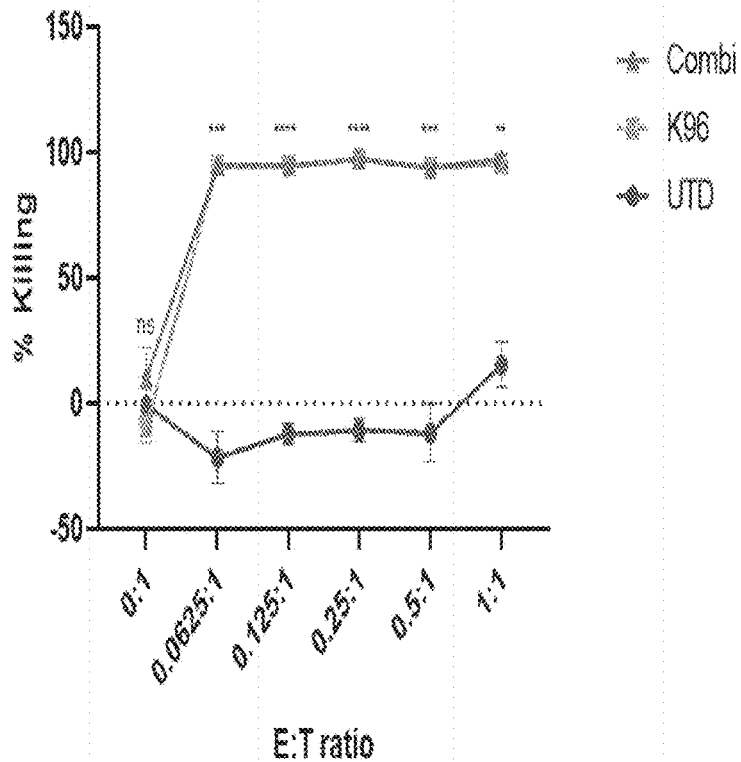
FIG. 18 shows a duplicate killing assay of GBM 6 over 5 days incubation by CAR T cells: K96 and "combinatorial CAR T cells" compared to UTD. Killing assays with K84 or both K84+K96 were not performed.
Figure 19:
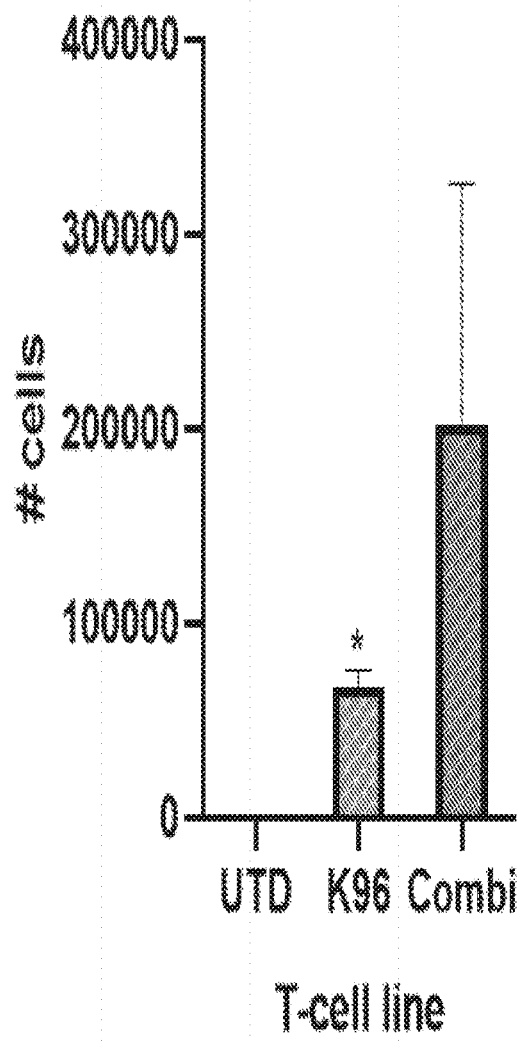
FIG. 19 shows a proliferation assay for K96 (EGFRviii targeting CAR-T cells) and "combinatorial CAR T cells" for GBM 6 line compared to UTD.
Figure 20:
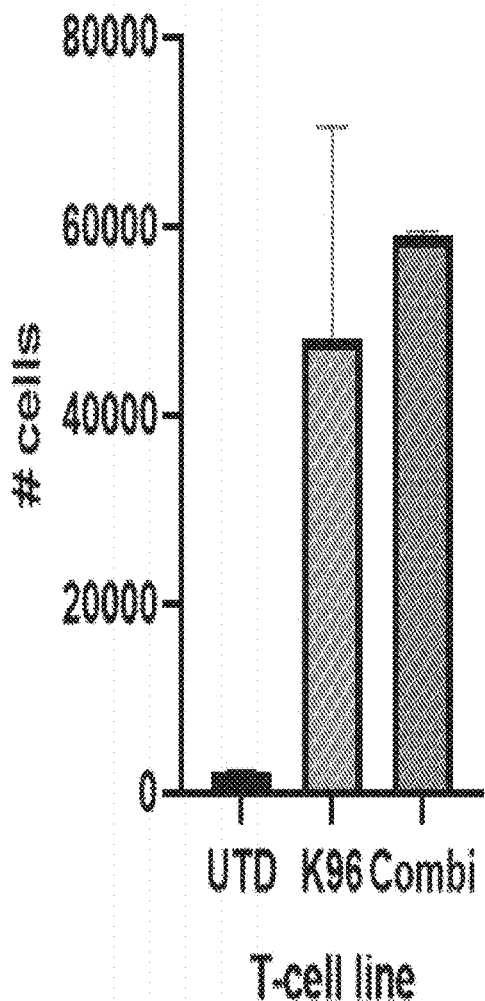
FIG. 20 shows a proliferation assay for K96 (EGFRviii targeting CAR-T cells) and "combinatorial CAR T cells" for GBM 150 line compared to UTD. GBM 150 is not supposed to have any EGFRviii expression, but it does have three copies of EGFR (chromosome 7). GBM 150 has 96.33% EphA3 expression per RNA seq.
Figure 21:
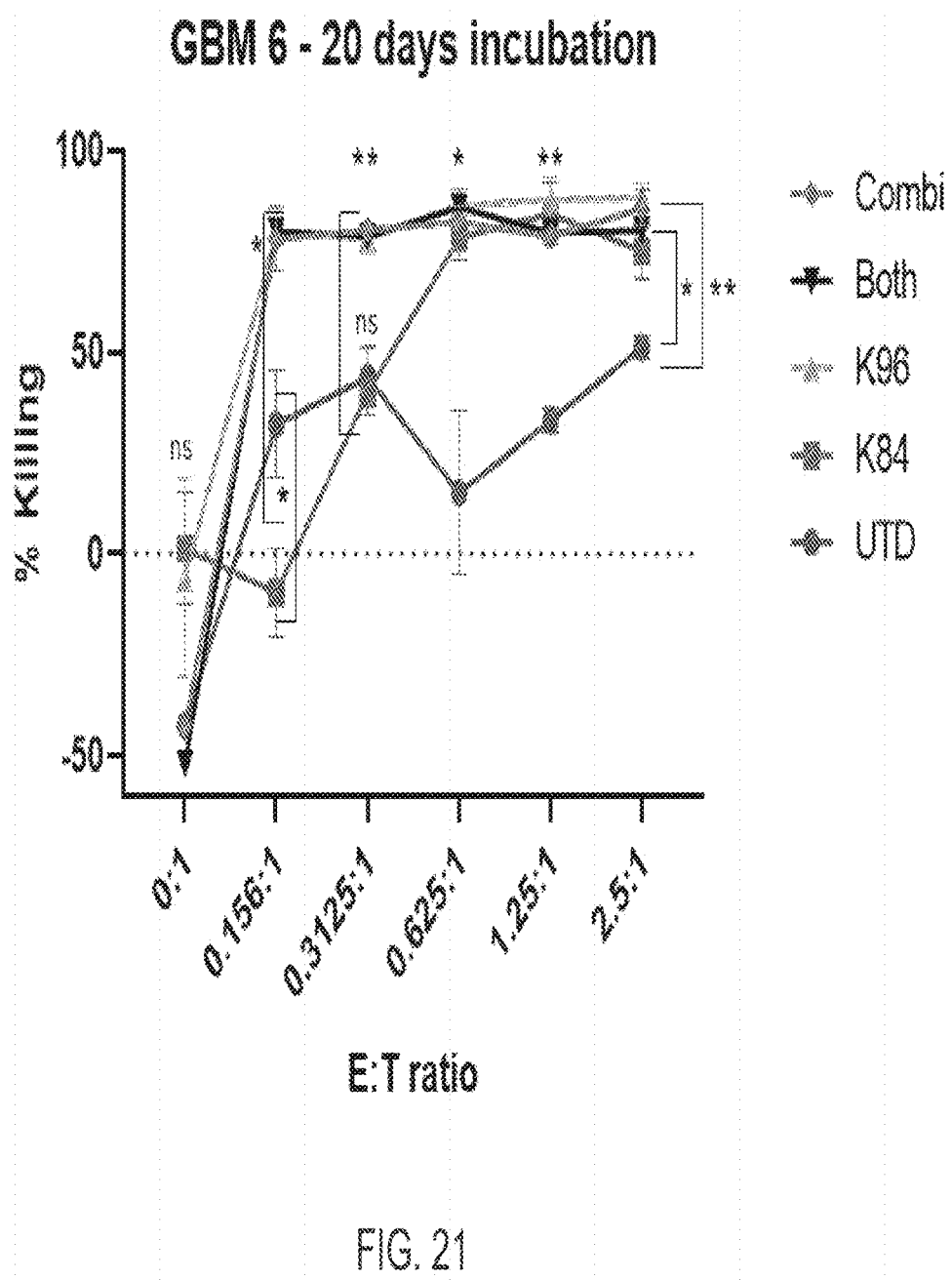
FIG. 21 shows a killing assay of GBM 6 over 20 days incubation by K84, K96, "both K84+K96" and "combinatorial CAR T cells" compared to UTD.
Figure 22:
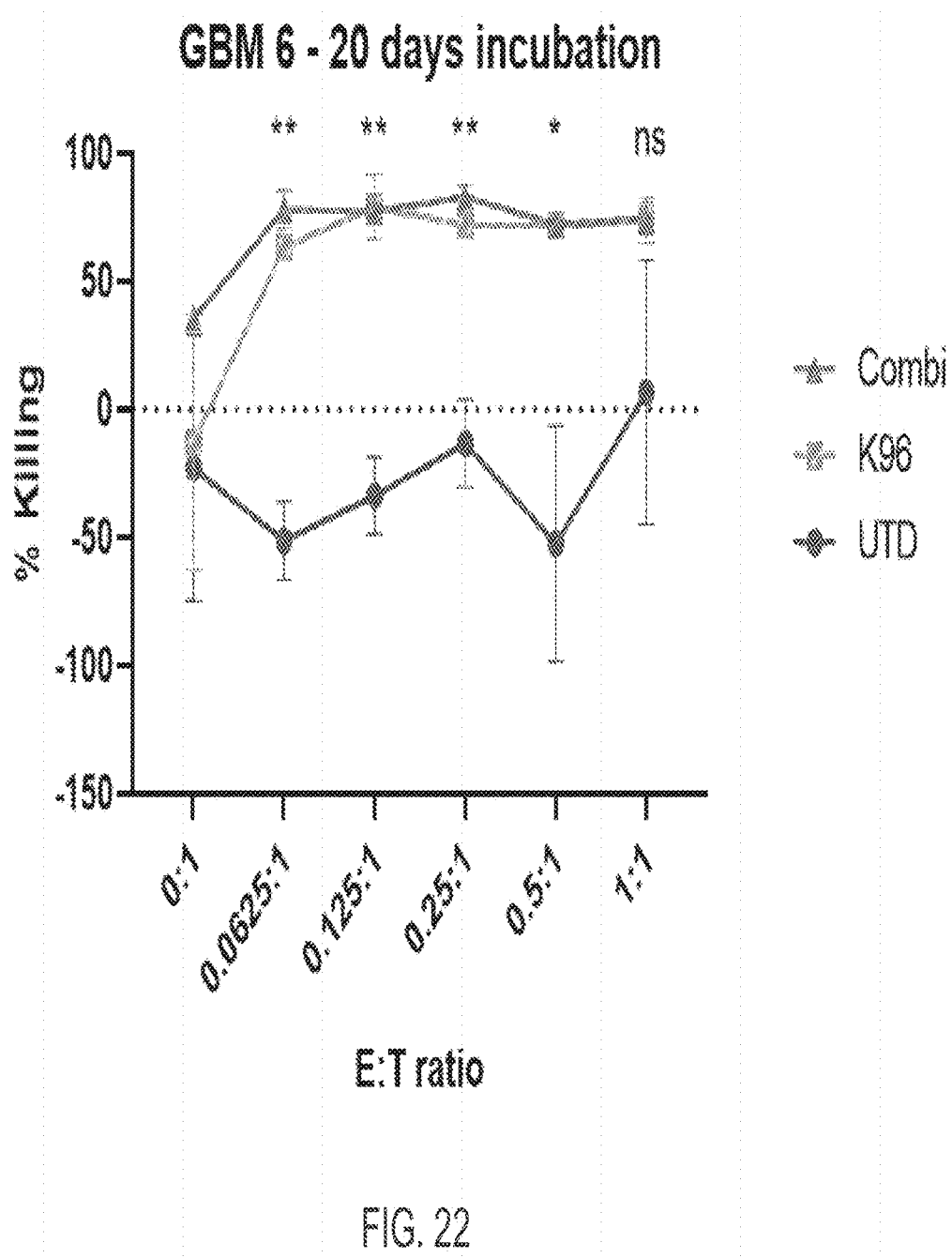
FIG. 22 shows a killing assay of GBM 6 over 20 days incubation by K96 and "combinatorial CAR T cells" compared to UTD. A one way ANOVA was performed comparing UTD versus K96 and UTD versus combinatorial (p value is for both tests).

Results:

We demonstrated CAR-T cell production of the EphA3 targeting CAR (termed CAR K084 (or "K84") (L2H-28z) (SEQ ID NO: 18)) on the surface of donor T-cells (FIGS. 1A-1B) by flow cytometry. A map of the CAR construct is shown (FIG. 1C). EphA3 directed CART cells exhibited specific and potent antitumor activity against EphA3+ GBM cell lines with variable transcriptome EphA3 expression indicating its broader applicability in patients with GBM (FIGS. 2B, 3A). Killing over 24-hour incubation was significant at low effector: target ratio: 52.5% killing at 1.25:1 against cell lines with 25.05% EphA3 expression and 37.1% killing at 1.25:1 and 90% killing at 5:1 ratio against a cell line with 19.28% expression. Conversely, when co-cultured with UTD controls there was significantly lower killing, or growth of tumor cells. Cell killing is demonstrated by decreased bioluminescence-a surrogate for viable tumor cells that express luciferase-when exposed to higher ratios of effector (CAR-T cell) to target (tumor cell) ratios when compared to un-transduced (UTD) from the same donor apheresis cone. There was not a significant difference in killing when co-cultured with cell lines with 6.95% EphA3 expression (FIG. 4A).

Example 2B

Methods:

We developed a second generation CD28 co-stimulated CAR construct in a third generation lentivirus backbone to generate EphA3 CART cells using the single chain variable fragment of ifabotuzumab, a monoclonal antibody directed against EphA3. Patient derived GBM xenograft cell lines were used in these experiments. The EphA-3 CART construct was designed and then synthesized de novo using a commercially available protein synthesis vendor using the following DNA sequence comprising a CD8 leader, a single chain variable fragment (scFv) of anti-human EphA3 monoclonal antibody ifabotuzumab (Ifab scFv) and a CD8 hinge:

```
                                                        (SEQ ID NO: 55)
GCTAGCTCTAGAATGGCCTTACCAGTGACCGCCTTGCTCCTGCCGCTGGCCTTGC

TGCTCCACGCCGCCAGGCCGGACATCCAGATGACCCAGTCTCCATCCTTCCTGTC

TGCATCTGTAGGAGACAGAGTCACCATCACTTGCCGGGCCAGTCAGGGCATTATC

AGTTATTTAGCCTGGTATCAGCAAAAACCAGAGAAAGCCCCTAAGCGCCTGATC

TATGCTGCATCCAGTTTGCAAAGTGGGGTCCCATCAAGGTTCAGCGGCAGTGGAT

CTGGGACAGAATTCACTCTCACAATCAGCAGCCTGCAGCCTGAAGATTTTGCAAC

TTACTACTGCGGGCAGTATGCCAATTATCCGTACACCTTTGGCCAAGGTACGAAA

CTGGAAATTAAAGGTGGAGGTGGTTCGGGAGGTGGAGGTAGCGGAGGTGGTGGA
```

-continued

```
TCTCAGGTGCAGCTGGTGCAGTCTGGGGCTGAGGTGAAGAAGCCTGGGGCCTCA

GTGAAGGTTTCCTGCAAGGCTTCTGGATACACCTTCACAGGCTACTGGATGAATT

GGGTGCGCCAGGCCCCCGGGCAAGGCCTGGAGTGGATGGGGGACATCTACCCGG

GCAGTGGTAACACAAACTACGATGAGAAGTTCCAGGGTAGAGTCACGATGACCA

GGGACACGTCCATCAGCACAGCCTACATGGAGCTGAGCAGGCTGAGATCTGACG

ACACAGCCGTGTACTACTGCGCAAGAGGTGGATATTATGAAGATTTTGATAGCTG

GGGCCAAGGTACCACTGTGACCGTGAGCTCCCTCGAGCCCAAATCTTGTGACAA

AACTCACACATGCCCACCGTGCCCGGATCCCAAATTTTGGGTGCTGGTGGTGGTT

GGTGGAGTCCTGGCTTGCTATAGCTTGCTAGTAACAGTGGCCTTTATTATTTTCTG

GGTGAGGAGTAAGAGGAGCAGGCTCCTGCACAGTGACTACATGAACATGACTCC

CCGCCGCCCCGGGCCCACCCGCAAGCATTACCAGCCCTATGCCCCACCACGCGA

CTTCGCAGCCTATCGCTCCAGAGTGAAGTTCAGCAGGAGCGCAGACGCCCCCGC

GTACAAGCAGGGCCAGAACCAGCTCTATAACGAGCTCAATCTAGGACGAAGAGA

GGAGTACGATGTTTTGGACAAGAGACGTGGCCGGGACCCTGAGATGGGGGGAAA

GCCGAGAAGGAAGAACCCTCAGGAAGGCCTGTACAATGAACTGCAGAAAGATA

AGATGGCGGAGGCCTACAGTGAGATTGGGATGAAAGGCGAGCGCCGGAGGGGC

AAGGGGCACGATGGCCTTTACCAGGGTCTCAGTACAGCCACCAAGGACACCTAC

GACGCCCTTCACATGCAGGCCCTGCCCCCTCGCTAAGTCGAC.
```

The EphA-3 CAR construct was subsequently cloned into a third generation lentivirus under control of an EF-la promoter. The single chain variable region fragment is a proprietary sequence produced by Humanigen. The EphA-3 construct possesses a second generation CD28 costimulatory domain and CD35 stimulation.

We performed lentiviral production using 293T cells at 70-90% confluency after allowing for incubation for 30 min at room temperature of transfection reagents including 15 µg of the Epha-3 lentiviral plasmid, 18 µg of a gag/pol/tat/rev packaging vector, 7 µg of a VSV-G envelope vector, 111 µL of the pre-complexing reagent, 129 µL of the transfection reagent, and 9.0 mL of the transfection medium before adding to the 293T cells. Then culture the transfected cells at 37° C., 5% CO2. We then harvested the cell media supernatant and concentrated by ultracentrifugation at 112,700×g for 2 h.

Human T-cells were isolated via a negative selection magnetic bead kit from peripheral blood mononuclear cells (PBMCs) from de-identified normal donor blood cones collected during apheresis. The isolated T cells were then stimulated with magnetic CD3/CD28 beads at a ratio of 3:1 beads:T cells and incubated for 24 hours.

We transduced stimulated T cells with harvested virus at a multiplicity of infection (MOI) of 3.0. CAR-T cells were then expanded by incubation at 37° C., 5% CO2, counted and fed at days 3 and 5 post lentiviral transduction and maintained at a CAR-T cell concentration of 1×10^6/mL. Six days after transduction cell surface expression of the CAR was assessed by flow cytometry. 100,000 T cells from the culture were washed with flow buffer prepared with Dulbecco's phosphate-buffered saline, 2% fetal bovine serum, and 1% sodium azide and subsequently stained with anti-CAR antibody (goat anti-mouse was used) and washed twice. The cells were stained with live/dead stain and CD3 monoclonal antibody. The cells were washed and resuspend in flow buffer and subsequently analyzed by flow cytometry to determine transduction efficiency. For killing assays, patient derived GBM xenograft cell lines (gift from Jann Sarkaria's lab) with varying expression of the target antigen by RNA-seq analysis were incubated at the indicated ratios with effector T cells for 24 hours. Killing was calculated by bioluminescence imaging on a Xenogen IVIS-200 Spectrum camera as a measure of residual live cells. Samples were treated with 1 ul D-luciferin (30 µg/mL) per 100 ul sample volume for 10 minutes prior to imaging.

Results:

We demonstrated CAR-T cell production of the Epha-3 targeting CAR (termed K84) on the surface of donor T-cells (FIG. 1) by flow cytometry. A map of the CAR construct is shown (FIG. 1). EphA3 directed CART cells exhibited specific and potent antitumor activity against EphA3+ GBM cell lines with variable transcriptome EphA3 expression indicating its broader applicability in patients with GBM (FIG. 2). Killing over 24-hour incubation was significant at low effector: target ratio: 52.5% killing at 1.25:1 against cell lines with 25.05% EphA3 expression and 37.1% killing at 1.25:1 and 90% killing at 5:1 ratio against a cell line with 19.28% expression. Conversely, when co-cultured with UTD controls there was significantly lower killing, or growth of tumor cells. Cell killing is demonstrated by decreased bioluminescence—a surrogate for viable tumor cells that express luciferase-when exposed to higher ratios of effector (CAR-T cell) to target (tumor cell) ratios when compared to un-transduced (UTD) from the same donor apheresis cone. There was not a significant difference in killing when co-cultured with cell lines. FIG. 25 shows EphA3 CAR expression on transduced T-cells (right) compared to untransduced T-cells (Left); a construct map is shown at the bottom. FIGS. 26A-26C show EphA3 CAR bioluminescence killing assay at 24 hour incubation versus GBM 76, GBM 6 and GBM 39. FIGS. 27A-27B show dual EPHA3/EGFRvIII targeting CART cells exhibit potent anti-tumor killing against patient derived GBM. In FIG. 28, combinatorial EGFRvIII and EphA3 CARs demonstrate increased proliferation when exposed to target antigen.

Conclusion: We demonstrate for the first time that targeting EphA3 with CART cells is feasible, specific, and efficacious and represents a novel therapeutic strategy to target GBM.

Example 3

Generation of CAR Binding to Human EphA3 and CART Cells Comprising the CAR

A CAR construct in lentivirus backbone is designed and synthesized as described in Example 1 to generate EphA3 CART cells comprising a chimeric antigen receptor (CAR) construct that binds to human Eph receptor A3 (EphA3) using a human EphA3 single chain variable fragment (scFv) of anti-EphA3 monoclonal antibody, wherein the human EphA3 scFv comprises CDR3 of the $V_H$ region comprises GGYYEDFDS (SEQ ID NO:44) and the CDR3 of the $V_L$ region comprises GQYANYPYT (SEQ ID NO:45).

Example 4

Generation of CAR Binding to Human EphA3 and CART Cells Comprising the CAR

A CAR construct in lentivirus backbone is designed and synthesized as described in Example 1 to generate EphA3 CART cells comprising a chimeric antigen receptor (CAR) construct that binds to human Eph receptor A3 (EphA3) using an extracellular anti-human EphA3 binding domain comprising:

a $V_H$ region comprising amino acid sequence:

(SEQ ID NO: 46)
QVQLVQSGAEVKKPGASVKVSCKASGYTFTGYWMNWVRQAPGQGLEWMG

DIYPGSGNTNYDEKFQGRVTMTRDTSISTAYMELSRLRSDDTAVYYCAR

GGYYEDFDSWGQGTTVTVSS and a $V_L$ region comprising amino acid sequence:

(SEQ ID NO: 47)
DIQMTQSPSFLSASVGDRVTITCRASQGIISYLAWYQQKPEKAPKRLIY

AASSLQSGVPSRFSGSGSGTEFTLTISSLQPEDFATYYCGQYANYPYTF

GQGTKLEIK.

Example 5

Generation of CAR Binding to Human EphA3 and CART Cells Comprising the CAR

A CAR construct in lentivirus backbone is designed and synthesized as described in Example 1 to generate EphA3 CART cells comprising a chimeric antigen receptor (CAR) construct that binds to human Eph receptor A3 (EphA3) using an extracellular anti-human EphA3 binding domain comprising:

a $V_H$ region CDR1 having a sequence SYWIN (SEQ ID NO:48), a $V_H$ region CDR2 having a sequence DIYPGSGNTNYDEKFKR (SEQ ID NO:49), a $V_H$ region CDR3 having a sequence SGYYEDFDS (SEQ ID NO:50), and a $V_L$ region CDR1 having a sequence RASQEISGYLG (SEQ ID NO:51), a $V_L$ region CDR2 having a sequence AASTLDS (SEQ ID NO:52), and a $V_L$ region CDR3 having a sequence VQYANYPYT (SEQ ID NO:53).

Example 6

Combination Therapy

A subject having a tumor that expresses EphA3 on its cell surface, or on the surface of tumor associated cells, is treated with human EphA3-targeting CAR T-cells, as described herein, and at least one immune checkpoint inhibitor, such as an anti-CTLA-4 antibody and/or an anti-PD-1 antibody to enhance the anti-tumor activity of the human EphA3-targeting CAR T-cells. The human EphA3-targeting CAR T-cells and the anti-CTLA-4 antibody and/or the anti-PD-1 antibody are administered sequentially in any order. CART cells (108-109) are dosed every 2-3 days for 16-20 days. Anti-CTLA-4 antibody and/or anti-PD-1 antibody are dosed monthly.

A tumor expressing EphA3 on its cell surface or the surface of tumor associated cells may be reduced in size by >50% within 3 months. After 12 months (4 cycles) of administration of this combination therapy, the subject's tumor may not be detectable by an imaging technique, such as a radiograms, a CT scan, an MRI, a PET scan and/or an ultrasound.

Example 7

Combination Therapy

A subject having a tumor that expresses EphA3 on its cell surface, or on the surface of tumor associated cells, is treated with human EphA3-targeting CAR T-cells, as described herein, and at least one immune checkpoint inhibitor, such as an anti-CTLA-4 antibody and/or an anti-PD-1 antibody to enhance the anti-tumor activity of the human EphA3-targeting CAR T-cells. The human EphA3-targeting CAR T-cells and the anti-CTLA-4 antibody and/or the anti-PD-1 antibody are administered sequentially in any order. If split dosing is required due to toxicity issues, the dosages of CART cells are split into two separate doses between day 0 and day 5 or 7. The anti-CTLA-4 antibody and/or anti-PD-1 antibody are dosed Q3 weeks.

Example 8

EphA3-Targeting CAR T-Cell and Immune Checkpoint Inhibitor Combination Therapy

In solid tumor patients receiving CAR-T therapy better clinical outcomes have been observed in those in which the CAR-T cells persist in the blood beyond 6 weeks. This suggests that clinical efficacy of CAR-T cells depends on their persistence. Suppression or exhaustion of CAR-T cells can lead to reduced expansion and persistence and hence reduced effect. This can be caused by PD-1/PD-L1 signaling which attenuates T-cell activities after antigen binding. PD-1 can be up-regulated on CART-cells in vivo leading to a loss in efficacy. It has been shown by others that the activity of tumor infiltrating T-cells can be inhibited by the up-regulation of both CTLA-4 and PD-1 co-inhibitory signals. Antibody blockade of CTLA-4 and/or PD-1 can enhance anti-tumor activity.

Ifabotuzumab is a humaneered monoclonal antibody that binds to human and mouse EphA3 receptor. A second generation CD28 co-stimulated and CD3ζ stimulated, anti-EphA3 CAR-T construct using the single chain variable region fragment of ifabotuzumab was constructed in a third generation lentivirus vector backbone (as described in this application).

Figures 23A, 23B, 23C:
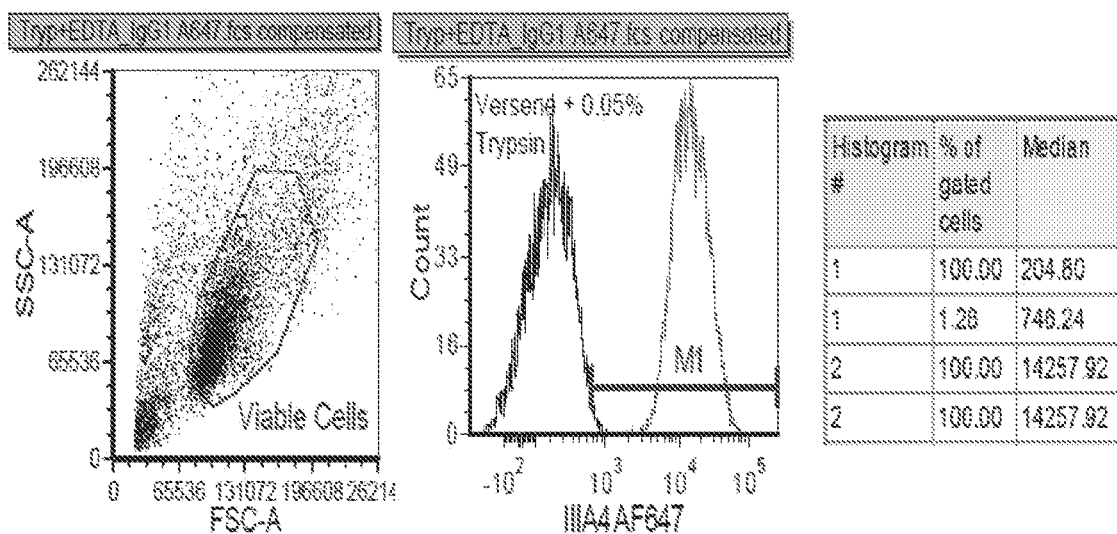
FIGS. 23A-23C show binding of IIIA4 antibody to NCI-H446 Cell line (Human SCLC).

Human small cell lung cancer cell line NCI-H446 expresses EphA3 on its cell surface as demonstrated by Flow cytometry studies using mouse anti-EphA3 antibody IIIA4 conjugated to Alexa Fluor 647 dye (FIGS. 23A-23C).

NCI-H446 cells are cultured in complete DMEM medium in flasks until they cover 70% of the bottom. Cells are then digested with 0.25% trypsin and passaged for expansion. Finally, the cancer cells are harvested, and then $1 \times 10^6$ cells injected subcutaneously into the left front dorsum of immune-deficient, NSG mice. Mice are monitored and subcutaneous (sc) tumors growth assessed. When tumors measure approximately 100 mm$^2$ dosing begins. Mice receive $1-1.5 \times 10^6$ CART cells (either transduced and expressing anti-EphA3 TCR or untransduced) intravenously. One group of mice also receives anti-PD1 monoclonal antibody (10 mg/kg) IP on day 0 and then every third day. Another group received anti-CTLA4 antibody (10 mg/kg) dosed every third day. Dosing continues for 25 days or until mice are terminated due to tumors reaching 1500 mm$^2$. Anti-tumor effects of EphA3-CART alone and in combination with anti-PD1 and/or anti-CTLA4 are assessed by measuring tumor size and overall survival.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A chimeric antigen receptor (CAR) that binds to human Eph receptor A3 (EphA3), the CAR comprising an extracellular anti-human EphA3 binding domain comprising a single chain variable fragment (scFv) of an anti-human EphA3 monoclonal antibody, wherein the anti-human EphA3 scFv comprises a heavy chain immunoglobulin variable region ($V_H$) comprising an amino acid sequence of SEQ ID NO: 1 and a light chain immunoglobulin variable region ($V_L$) comprising an amino acid sequence of SEQ ID NO: 2 wherein the extracellular anti-human EphA3 binding domain is connected to a CD28 transmembrane domain by a CD28 hinge region, wherein the CAR further comprises an intracellular signaling domain, wherein the intracellular signaling domain comprises a costimulatory domain and an activation domain, wherein the costimulatory domain comprises a CD28 costimulatory domain, wherein the activation domain is a CD3 zeta (CD3z) or CD3ζ activation domain, and wherein the CAR is expressed in a T cell.

2. The CAR of claim 1, wherein the $V_H$ and the $V_L$ are attached by a linker peptide.

3. The CAR of claim 2, wherein the linker peptide comprises an amino acid sequence of SEQ ID NO: 4.

4. The CAR of claim 1, wherein the CD28 hinge region comprises an amino acid sequence of SEQ ID NO: 6.

5. The CAR of claim 1, wherein the CD28 transmembrane domain comprises an amino acid sequence of SEQ ID NO: 8.

6. The CAR of claim 1, further comprising a leader sequence.

7. The CAR of claim 6, wherein the leader sequence comprises an amino acid sequence of SEQ ID NO: 3.

8. The CAR of claim 1, wherein the CD28 costimulatory domain comprises an amino acid sequence of SEQ ID NO: 10.

9. The CAR of claim 1, wherein the CD3z activation domain comprises an amino acid sequence of SEQ ID NO: 11.

10. The CAR of claim 1, wherein the VH and VL are attached by a linker peptide comprising an amino acid sequence of SEQ ID NO: 4 and the CD28 hinge region comprises the amino acid sequence of SEQ ID NO:6.

11. The CAR of claim 10, wherein the CD28 transmembrane domain comprises
an amino acid sequence of SEQ ID NO: 8.

12. The CAR of claim 10, wherein the CD28 costimulatory domain comprises an amino acid sequence of SEQ ID NO: 10.

13. The CAR of claim 10, wherein the CD3z activation domain comprises an amino acid sequence of SEQ ID NO: 11.

14. The CAR construct of claim 10, wherein the scFv of a monoclonal antibody that binds to human EphA3, the hinge region, the transmembrane domain, and the intracellular signaling domain are fused in tandem.

15. A human EphA3-targeting CAR expression cassette comprising the CAR of claim 1 cloned into a lentivirus backbone under control of a promoter.

16. The human EphA3-targeting CAR expression cassette of claim 15, wherein the promoter is human elongation factor-1 alpha (EF-1α).

17. The human EphA3-targeting CAR expression cassette of claim 15, wherein the lentivirus backbone is a third generation lentivirus backbone.

18. The human EphA3-targeting CAR T cell comprising the EphA3-CAR expression cassette of claim 15, wherein the CAR is expressed on the surface of the T cell.

19. A pharmaceutical composition comprising the human EphA3-targeting CAR T-cell of claim 18 and a pharmaceutically acceptable carrier, wherein the EphA3-targeting CAR T-cell is an autologous EphA3-targeting CAR T-cell.

20. A method for producing a human EphA3-targeting CAR T-cell, the method comprising transducing a T-cell with the EphA3 CAR expression cassette of claim 15.

21. The CAR of claim 1 comprising amino acid sequence:

```
                                                  (SEQ ID NO: 13)
MALPVTALLLPLALLLHAARPQVQLVQSGAEVKKPGASVKVSCKASGYT

FTGYWMNWVRQAPGQGLEWMGDIYPGSGNTNYDEKFQGRVTMTRDTSIS

TAYMELSRLRSDDTAVYYCARGGYYEDFDSWGQGTTVTVSSGGGGSGGG

GSGGGGSDIQMTQSPSFLSASVGDRVTITCRASQGIISYLAWYQQKPEK

APKRLIYAASSLQSGVPSRFSGSGSGTEFTLTISSLQPEDFATYYCGQY

ANYPYTFGQGTKLEIKLEPKSCDKTHTCPPCPDPKFWVLVVVGGVLACY

SLLVTVAFIIFWVRSKRSRLLHSDYMNMTPRRPGPTRKHYQPYAPPRDF

AAYRSRVKFSRSADAPAYKQGQNQLYNELNLGRREEYDVLDKRRGRDPE

MGGKPRRKNPQEGLYNELQKDKMAEAYSEIGMKGERRRGKGHDGLYQGL

STATKDTYDALHMQALPPR.
```

\* \* \* \* \*